(12) United States Patent
Wang et al.

(10) Patent No.: US 11,795,207 B2
(45) Date of Patent: Oct. 24, 2023

(54) MODIFIED PLASMA CLOTTING FACTOR VIII AND METHOD OF USE THEREOF

(71) Applicant: AAVnerGene Inc., Rockville, MD (US)

(72) Inventors: Qizhao Wang, Rockville, MD (US); Daozhan Yu, Ellicott City, MD (US)

(73) Assignee: AAVNERGENE INC., North Bethesda, MD (US)

( * ) Notice: Subject to any disclaimer, the term of this patent is extended or adjusted under 35 U.S.C. 154(b) by 91 days.

(21) Appl. No.: 17/217,285

(22) Filed: Mar. 30, 2021

(65) Prior Publication Data

US 2022/0315643 A1 Oct. 6, 2022

(51) Int. Cl.
*C07K 14/755* (2006.01)
*C12N 15/86* (2006.01)
*A61K 38/00* (2006.01)

(52) U.S. Cl.
CPC ............ *C07K 14/755* (2013.01); *C12N 15/86* (2013.01); *A61K 38/00* (2013.01)

(58) Field of Classification Search
None
See application file for complete search history.

(56) References Cited

U.S. PATENT DOCUMENTS

| 4,501,729 | A  | 2/1985  | Boucher et al.       |
|-----------|----|---------|----------------------|
| 5,478,745 | A  | 12/1995 | Samulski et al.      |
| 5,859,204 | A  | 1/1999  | Lollar               |
| 6,114,148 | A  | 9/2000  | Seed et al.          |
| 6,491,907 | B1 | 12/2002 | Rabinowitz et al.    |
| 6,770,744 | B2 | 8/2004  | Lollar               |
| 6,780,614 | B2 | 8/2004  | Negrier et al.       |
| 6,800,461 | B2 | 10/2004 | Negrier et al.       |
| 2003/0166536 | A1 | 9/2003 | Lollar             |
| 2004/0029106 | A1 | 2/2004 | Samulski et al.    |
| 2004/0197875 | A1 | 10/2004 | Hauser et al.     |
| 2008/0194511 | A1 | 8/2008 | Draghia-Akli et al. |
| 2016/0102133 | A1 | 4/2016 | Xiao et al.        |
| 2020/0289672 | A1 | 9/2020 | Rottensteiner et al. |

FOREIGN PATENT DOCUMENTS

WO        2019197524        10/2019
WO        WO-2019197524 A1 * 10/2019 ........... C07K 14/755

OTHER PUBLICATIONS

International Search Report and Written Opinion, issued in International Patent Application No. PCT/US2021/024916, dated Mar. 25, 2022.

* cited by examiner

*Primary Examiner* — Melissa L Fisher
*Assistant Examiner* — Joseph Fischer
(74) *Attorney, Agent, or Firm* — Michael Ye; Rimon Law

(57) ABSTRACT

Modified hum1.an factor VIII polypeptides with enhanced factor VIII activity are described. In some embodiments, the modified human factor VIII polypeptides comprise one or more amino acid substitutions at positions A20, T21, P57, L69, I80, L178, R199, H212, I215, R269, I310, L318, S332, R378, I610 and/or I661. Such polypeptides and viral vectors encoding such polypeptides may be used for treatment of FVIII deficiencies, such as hemophilia A.

26 Claims, 13 Drawing Sheets

Figure 1:
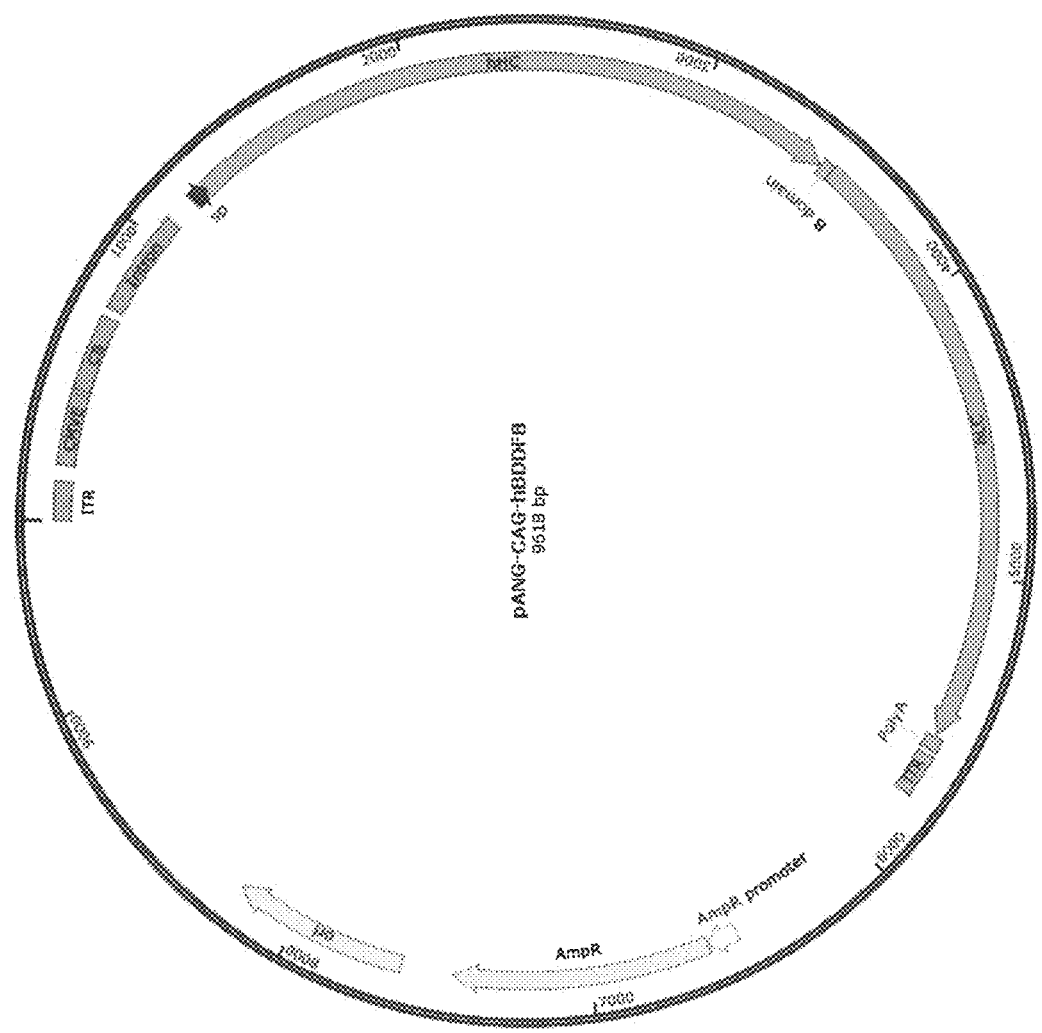

Specification includes a Sequence Listing.

Identification of amino acids mutated in hFVIII HC

```
                      1                   2                   3                   4                   5
hBDDF8    1  ---Signal peptide---12
hBDDF8    1  MQIELSTCFFLCLLRFCFSATRRYYLGAVELSWDYMQSDLGELPVDARFPPRVPKSFPFNTSVVYKKTLFVEFTDHLFNIAKPRPPWMGLLGPTIQAEVY 100
qwBDDF8   1  MQIELSTCFFLCLLRFCFSKVRRYYLGAVELSWDYMQSDLGELPVDARFPPRVPKSLPFNTSVVYKKTVFVEFTDHLFNVAKPRPPWMGLLGPTIQAEVY 100
                                   1                                   6                                   7 hBDDF8  101  DTVVITLKNMASHPVSLHAVGVSYWKASEGAEYDDQTSQREKEDDKVFPGGSHTYVWQVLKENGPMASDPLCLTYSYLSHVDLVKDLNSGLIGALLVCRE 200
qwBDDF8 101  DTVVITLKNMASHPVSLHAVGVSYWKASEGAEYDDQTSQREKEDDKVFPGGSHTYVWQVLKENGPMASDPLCLTYSYFSHVDLVKDLNSGLIGALLVCKE 200
                                                                       8   9                              10 hBDDF8  201  GSLAKEKTQTLHKFILLFAVFDEGKSWHSETKNSLMQDRDAASARAWPKMHTVNGYVNRSLPGLIGCHRKSVYWHVIGMGTTPEVHSIFLEGHTPLVRNH 300
qwBDDF8 201  GSLAKEKTQTLQKFVLLFAVFDEGKSWNHSETKNSLMQDRDAASARAWPKMHTVNGYVNRSLPGLIGCHKKSVYWHVIGMGTTPEVHSIFLEGHTPLVRNH 300
                           11 12                 13                                                      14 hBDDF8  301  RQASLEISPITFLTAQTLLMDLGQFLLFCHISSHQHDGMEAYVKVDSCPEEPQLRMKNNEEAEDYDDLTDSEMDVVRFDDDNSPSFIQIRSVAKKHPKT 400
qwBDDF8 301  RQASLEISPVTFLTAQTLMDLGQFLLFCHIPSHQHDGMEAYVKVDSCPEEPQLRMKNNEEAEDYDDLTDSEMDVSFDDNSPSFIQIRSVAKKHPKT 400 hBDDF8  401  WVHYIAAEEEDWDYAPLVLAPDDRSYKSQYLNNGPQRIGRKYKKVRFMAYTDETFKTREAIQHESGILGPLLYGEVGDTLLIIFKNQASKPYNIYPHGIT 500
qwBDDF8 401  WVHYIAAEEEDWDYAPLVLAPDDRSYKSQYLNNGPQRIGRKYKKVRFMAYTDETFKTREAIQHESGILGPLLYGEVGDTLLIIFKNQASKPYNIYPHGIT 500 hBDDF8  501  DVRPLYSRRLPKGVKHLKDFPILPGEIFKYKWTVTVEDGPTKSDPRCLTRYYSSFVNMERDLASGLIGPLLICYKESVDQRGNQIMSDKRNVILFSVFDE 600
qwBDDF8 501  DVRPLYSRRLPKGVKHLKDFPILPGEIFKYKWTVTVEDGPTKSDPRCLTRYYSSFVNMERDLASGLIGPLLICYKESVDQRGNQIMSDKRNVILFSVFDE 600
                                          15                                                        16 hBDDF8  601  NRSWYLTENIQRFLPNPAGVQLEDPEFQASNIMHSINGYVFDSLQLSVCLHEVAYWYILSIGAQTDFLSVFFSGYTFKHKMVYEDTLTLFPFSGETVFMS 700
qwBDDF8 601  NRSWYLTENMQRFLPNPAGVQLEDPEFQASNIMHSINGYVFDSLQLSVCLHEVAYWYILSVGAQTDFLSVFFSGYTFKHKMVYEDTLTLFPFSGETVFMS 700
                                                                                    Light Chain hBDDF8  701  MENPGLWILGCHNSDFRNRGMTALLKVSSCDKNTGDYYEDSYEDISAYLLSKNNAIEPRSFSQNPPVLKRHQREITRTTLQSDQEEIDYDD--(SEQ ID NO:16)
qwBDDF8 701  MENPGLWILGCHNSDFRNRGMTALLKVSSCDKNTGDYYEDSYEDISAYLLSKNNAIEPRSFSQNPPVLKRHQREITRTTLQSDQEEIDYDD--(SEQ ID NO:17)
                                      B domain
```

*FIG. 2*

SEQUENCE LISTING

```
<160> NUMBER OF SEQ ID NOS: 18

<210> SEQ ID NO 1
<211> LENGTH: 7056
<212> TYPE: DNA
<213> ORGANISM: Homo sapiens
<220> FEATURE:
<221> NAME/KEY: misc_feature
<223> OTHER INFORMATION: Human Factor VIII

<400> SEQUENCE: 1
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaagttgg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca aagtagacag ctgtccagag gaaccccaac tacgaatgaa aaataatgaa    1080
gaagcggaag actatgatga tgatcttact gattctgaaa tggatgtggt caggtttgat    1140
```

```
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg ccctcagcg gattggtagg    1320 aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaggtg taaaacattt gaaggatttt    1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccctt caaacacaaa   2040 atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga attcaagaca ccctagcact aggcaaaagc aatttaatgc caccacaatt   2340
ccagaaaatg acatagagaa gactgaccct tggtttgcac acagaacacc tatgcctaaa   2400
atacaaaatg tctcctctag tgatttgttg atgctcttgc gacagagtcc tactccacat   2460
gggctatcct tatctgatct ccaagaagcc aaatatgaga cttttcctga tgatccatca   2520
cctggagcaa tagacagtaa taacagcctg tctgaaatga cacacttcag gcccacagctc  2580 catcacagtg gggacatggt atttaccccct gagtcaggcc tccaattaag attaaatgag  2640
aaactgggga caactgcagc aacagagttg aagaaacttg atttcaaagt ttctagtaca   2700
tcaaataatc tgatttcaac aattccatca gacaatttgg cagcaggtac tgataataca   2760
agttccttag gaccccccaag tatgccagtt cattatgata gtcaattaga taccactcta   2820
tttggcaaaa agtcatctcc ccttactgag tctggtggac ctctgagctt gagtgaagaa   2880
aataatgatt caaagttgtt agaatcaggt ttaatgaata gccaagaaag ttcatgggga   2940
aaaaatgtat cgtcaacaga gagtggtagg ttatttaaag ggaaaagagc tcatggacct   3000
gctttgttga ctaaagataa tgccttattc aaagttagca tctctttgtt aaagacaaac   3060
aaaacttcca ataattcagc aactaataga aagactcaca ttgatggccc atcattatta   3120
attgagaata gtccatcagt ctggcaaaat atattagaaa gtgacactga gtttaaaaaa   3180
gtgacacctt tgattcatga cagaatgctt atggacaaaa atgctacagc tttgaggcta   3240
aatcatatgt caaataaaac tacttcatca aaaaacatgg aaatggtcca acagaaaaaa   3300
gagggcccca ttccaccaga tgcacaaaat ccagatatgt cgttctttaa gatgctattc   3360
ttgccagaat cagcaaggtg gatacaaagg actcatggaa agaactctct gaactctggg   3420
caaggcccca gtccaaagca attagtatcc ttaggaccag aaaaatctgt ggaaggtcag   3480
```

```
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaagaag     3660
gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca caaggatatc tcctaataca    3960
agccagcaga attttgtcac gcaacgtagt aagagagctt tgaaacaatt cagactccca    4020
ctagaagaaa cagaacttga aaaaggata attgtggatg cacctcaac ccagtggtcc      4080
aaaaacatga acatttgac cccgagcacc ctcacacaga tagactacaa tgagaaggag     4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct tacaaggagc caaaaaaaat    4380
aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac atttgggact cctgggccca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc ctgctcatgg gagacaagtg acagtacagg aatttgctct gttttttcacc   5700
atctttgatg agaccaaaag ctggtacttc actgaaaata tggaaagaaa ctgcagggct    5760
ccctgcaata tccagatgga agatcccact ttttaaagaga attatcgctt ccatgcaatc    5820
aatggctaca taatggatac actacctggc ttagtaatgg ctcaggatca aaggattcga    5880
```

```
tggtatctgc tcagcatggg cagcaatgaa acatccatt  ctattcattt cagtggacat    5940
gtgttcactg tacgaaaaaa agaggagtat aaaatggcac tgtacaatct ctatccaggt    6000
gtttttgaga cagtggaaat gttaccatcc aaagctggaa tttggcgggt ggaatgcctt    6060
attggcgagc atctacatgc tgggatgagc acacttttc  tggtgtacag caataagtgt    6120
cagactcccc tgggaatggc ttctggacac attagagatt ttcagattac agcttcagga    6180
caatatggac agtgggcccc aaagctggcc agacttcatt attccggatc aatcaatgcc    6240
tggagcacca aggagccctt tcttggatc  aaggtggatc tgttggcacc aatgattatt    6300
cacggcatca gacccaggg  tgcccgtcag aagttctcca gcctctacat ctctcagttt    6360
atcatcatgt atagtcttga tgggaagaag tggcagactt atcgaggaaa ttccactgga    6420
accttaatgg tcttctttgg caatgtggat tcatctggga taaacacaa  tatttttaac    6480 cctccaatta ttgctcgata catccgtttg cacccaactc attatagcat tcgcagcact    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900 gttttcagg  gaaatcaaga ctccttcaca cctgtggtga actctctaga cccaccgtta    6960
ctgactcgct accttcgaat tcacccccag agttgggtgc accagattgc cctgaggatg    7020
gaggttctgg gctgcgaggc acaggacctc tactga                              7056
```

<210> SEQ ID NO 2
<211> LENGTH: 19
<212> TYPE: PRT
<213> ORGANISM: Homo sapiens
<220> FEATURE:
<221> NAME/KEY: misc_feature
<223> OTHER INFORMATION: Human factor VIII signal peptide

<400> SEQUENCE: 2

Met Gln Ile Glu Leu Ser Thr Cys Phe Phe Leu Cys Leu Leu Arg Phe
1               5                   10                  15

Cys Phe Ser

<210> SEQ ID NO 3
<211> LENGTH: 2351
<212> TYPE: PRT
<213> ORGANISM: Homo sapiens
<220> FEATURE:
<221> NAME/KEY: misc_feature
<223> OTHER INFORMATION: Human Factor VIII with signal peptide

<400> SEQUENCE: 3

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

```
Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480
```

```
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
        755                 760                 765
Ser Thr Arg Gln Lys Gln Phe Asn Ala Thr Thr Ile Pro Glu Asn Asp
    770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
            820                 825                 830
Glu Thr Phe Ser Asp Asp Pro Ser Pro Gly Ala Ile Asp Ser Asn Asn
        835                 840                 845
Ser Leu Ser Glu Met Thr His Phe Arg Pro Gln Leu His His Ser Gly
    850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
```

```
                  900                 905                 910
Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
            995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305
```

```
Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695
```

```
Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Pro Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
```

-continued

```
                2090                2095                2100
Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 4
<211> LENGTH: 2332
<212> TYPE: PRT
<213> ORGANISM: Homo sapiens
<220> FEATURE:
<221> NAME/KEY: misc_feature
<223> OTHER INFORMATION: Human Factor VIII without signal peptide

<400> SEQUENCE: 4

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80
```

```
Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
        130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
```

```
                500             505                 510
Trp Thr Val Thr Val Glu Asp Gly Pro Thr Lys Ser Asp Pro Arg Cys
            515                 520             525

Leu Thr Arg Tyr Tyr Ser Ser Phe Val Asn Met Glu Arg Asp Leu Ala
            530                 535             540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570             575

Ser Val Phe Asp Glu Asn Arg Ser Trp Tyr Leu Thr Glu Asn Ile Gln
            580                 585             590

Arg Phe Leu Pro Asn Pro Ala Gly Val Gln Leu Glu Asp Pro Glu Phe
        595                 600             605

Gln Ala Ser Asn Ile Met His Ser Ile Asn Gly Tyr Val Phe Asp Ser
            610                 615             620

Leu Gln Leu Ser Val Cys Leu His Glu Val Ala Tyr Trp Tyr Ile Leu
625                 630             635                 640

Ser Ile Gly Ala Gln Thr Asp Phe Leu Ser Val Phe Phe Ser Gly Tyr
                645             650                 655

Thr Phe Lys His Lys Met Val Tyr Glu Asp Thr Leu Thr Leu Phe Pro
            660                 665             670

Phe Ser Gly Glu Thr Val Phe Met Ser Met Glu Asn Pro Gly Leu Trp
            675                 680             685

Ile Leu Gly Cys His Asn Ser Asp Phe Arg Asn Arg Gly Met Thr Ala
        690                 695             700

Leu Leu Lys Val Ser Ser Cys Asp Lys Asn Thr Gly Asp Tyr Tyr Glu
705                 710             715                 720

Asp Ser Tyr Glu Asp Ile Ser Ala Tyr Leu Leu Ser Lys Asn Asn Ala
                725             730                 735

Ile Glu Pro Arg Ser Phe Ser Gln Asn Ser Arg His Pro Ser Thr Arg
            740                 745             750

Gln Lys Gln Phe Asn Ala Thr Thr Ile Pro Glu Asn Asp Ile Glu Lys
            755                 760             765

Thr Asp Pro Trp Phe Ala His Arg Thr Pro Met Pro Lys Ile Gln Asn
            770                 775             780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810             815

Ser Asp Asp Pro Ser Pro Gly Ala Ile Asp Ser Asn Asn Ser Leu Ser
            820                 825             830

Glu Met Thr His Phe Arg Pro Gln Leu His His Ser Gly Asp Met Val
            835                 840             845

Phe Thr Pro Glu Ser Gly Leu Gln Leu Arg Leu Asn Glu Lys Leu Gly
        850                 855             860

Thr Thr Ala Ala Thr Glu Leu Lys Lys Leu Asp Phe Lys Val Ser Ser
865                 870             875                 880

Thr Ser Asn Asn Leu Ile Ser Thr Ile Pro Ser Asp Asn Leu Ala Ala
                885                 890             895

Gly Thr Asp Asn Thr Ser Ser Leu Gly Pro Pro Ser Met Pro Val His
        900                 905             910

Tyr Asp Ser Gln Leu Asp Thr Thr Leu Phe Gly Lys Lys Ser Ser Pro
            915                 920             925
```

```
Leu Thr Glu Ser Gly Gly Pro Leu Ser Leu Ser Glu Glu Asn Asn Asp
    930             935             940

Ser Lys Leu Leu Glu Ser Gly Leu Met Asn Ser Gln Glu Ser Ser Trp
945             950             955             960

Gly Lys Asn Val Ser Ser Thr Glu Ser Gly Arg Leu Phe Lys Gly Lys
                965             970             975

Arg Ala His Gly Pro Ala Leu Leu Thr Lys Asp Asn Ala Leu Phe Lys
            980             985             990

Val Ser Ile Ser Leu Leu Lys Thr Asn Lys Thr Ser Asn Asn Ser Ala
        995             1000            1005

Thr Asn Arg Lys Thr His Ile Asp Gly Pro Ser Leu Leu Ile Glu
    1010            1015            1020

Asn Ser Pro Ser Val Trp Gln Asn Ile Leu Glu Ser Asp Thr Glu
    1025            1030            1035

Phe Lys Lys Val Thr Pro Leu Ile His Asp Arg Met Leu Met Asp
    1040            1045            1050

Lys Asn Ala Thr Ala Leu Arg Leu Asn His Met Ser Asn Lys Thr
    1055            1060            1065

Thr Ser Ser Lys Asn Met Glu Met Val Gln Gln Lys Lys Glu Gly
    1070            1075            1080

Pro Ile Pro Pro Asp Ala Gln Asn Pro Asp Met Ser Phe Phe Lys
    1085            1090            1095

Met Leu Phe Leu Pro Glu Ser Ala Arg Trp Ile Gln Arg Thr His
    1100            1105            1110

Gly Lys Asn Ser Leu Asn Ser Gly Gln Gly Pro Ser Pro Lys Gln
    1115            1120            1125

Leu Val Ser Leu Gly Pro Glu Lys Ser Val Glu Gly Gln Asn Phe
    1130            1135            1140

Leu Ser Glu Lys Asn Lys Val Val Val Gly Lys Gly Glu Phe Thr
    1145            1150            1155

Lys Asp Val Gly Leu Lys Glu Met Val Phe Pro Ser Ser Arg Asn
    1160            1165            1170

Leu Phe Leu Thr Asn Leu Asp Asn Leu His Glu Asn Asn Thr His
    1175            1180            1185

Asn Gln Glu Lys Lys Ile Gln Glu Glu Ile Glu Lys Lys Glu Thr
    1190            1195            1200

Leu Ile Gln Glu Asn Val Val Leu Pro Gln Ile His Thr Val Thr
    1205            1210            1215

Gly Thr Lys Asn Phe Met Lys Asn Leu Phe Leu Leu Ser Thr Arg
    1220            1225            1230

Gln Asn Val Glu Gly Ser Tyr Asp Gly Ala Tyr Ala Pro Val Leu
    1235            1240            1245

Gln Asp Phe Arg Ser Leu Asn Asp Ser Thr Asn Arg Thr Lys Lys
    1250            1255            1260

His Thr Ala His Phe Ser Lys Lys Gly Glu Glu Glu Asn Leu Glu
    1265            1270            1275

Gly Leu Gly Asn Gln Thr Lys Gln Ile Val Glu Lys Tyr Ala Cys
    1280            1285            1290

Thr Thr Arg Ile Ser Pro Asn Thr Ser Gln Gln Asn Phe Val Thr
    1295            1300            1305

Gln Arg Ser Lys Arg Ala Leu Lys Gln Phe Arg Leu Pro Leu Glu
    1310            1315            1320
```

-continued

| | | | | | | | | | | | |
|---|---|---|---|---|---|---|---|---|---|---|---|
| Glu<br>1325 | Thr | Glu | Leu | Glu | Lys<br>1330 | Arg | Ile | Ile | Val | Asp<br>1335 | Asp | Thr | Ser | Thr |

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro

```
                1715                1720                1725

Gln Phe Lys Lys Val Val Phe Gln Glu Phe Thr Asp Gly Ser Phe
            1730                1735                1740

Thr Gln Pro Leu Tyr Arg Gly Glu Leu Asn Glu His Leu Gly Leu
            1745                1750                1755

Leu Gly Pro Tyr Ile Arg Ala Glu Val Glu Asp Asn Ile Met Val
            1760                1765                1770

Thr Phe Arg Asn Gln Ala Ser Arg Pro Tyr Ser Phe Tyr Ser Ser
            1775                1780                1785

Leu Ile Ser Tyr Glu Glu Asp Gln Arg Gln Gly Ala Glu Pro Arg
            1790                1795                1800

Lys Asn Phe Val Lys Pro Asn Glu Thr Lys Thr Tyr Phe Trp Lys
            1805                1810                1815

Val Gln His His Met Ala Pro Thr Lys Asp Glu Phe Asp Cys Lys
            1820                1825                1830

Ala Trp Ala Tyr Phe Ser Asp Val Asp Leu Glu Lys Asp Val His
            1835                1840                1845

Ser Gly Leu Ile Gly Pro Leu Leu Val Cys His Thr Asn Thr Leu
            1850                1855                1860

Asn Pro Ala His Gly Arg Gln Val Thr Val Gln Glu Phe Ala Leu
            1865                1870                1875

Phe Phe Thr Ile Phe Asp Glu Thr Lys Ser Trp Tyr Phe Thr Glu
            1880                1885                1890

Asn Met Glu Arg Asn Cys Arg Ala Pro Cys Asn Ile Gln Met Glu
            1895                1900                1905

Asp Pro Thr Phe Lys Glu Asn Tyr Arg Phe His Ala Ile Asn Gly
            1910                1915                1920

Tyr Ile Met Asp Thr Leu Pro Gly Leu Val Met Ala Gln Asp Gln
            1925                1930                1935

Arg Ile Arg Trp Tyr Leu Leu Ser Met Gly Ser Asn Glu Asn Ile
            1940                1945                1950

His Ser Ile His Phe Ser Gly His Val Phe Thr Val Arg Lys Lys
            1955                1960                1965

Glu Glu Tyr Lys Met Ala Leu Tyr Asn Leu Tyr Pro Gly Val Phe
            1970                1975                1980

Glu Thr Val Glu Met Leu Pro Ser Lys Ala Gly Ile Trp Arg Val
            1985                1990                1995

Glu Cys Leu Ile Gly Glu His Leu His Ala Gly Met Ser Thr Leu
            2000                2005                2010

Phe Leu Val Tyr Ser Asn Lys Cys Gln Thr Pro Leu Gly Met Ala
            2015                2020                2025

Ser Gly His Ile Arg Asp Phe Gln Ile Thr Ala Ser Gly Gln Tyr
            2030                2035                2040

Gly Gln Trp Ala Pro Lys Leu Ala Arg Leu His Tyr Ser Gly Ser
            2045                2050                2055

Ile Asn Ala Trp Ser Thr Lys Glu Pro Phe Ser Trp Ile Lys Val
            2060                2065                2070

Asp Leu Leu Ala Pro Met Ile Ile His Gly Ile Lys Thr Gln Gly
            2075                2080                2085

Ala Arg Gln Lys Phe Ser Ser Leu Tyr Ile Ser Gln Phe Ile Ile
            2090                2095                2100

Met Tyr Ser Leu Asp Gly Lys Lys Trp Gln Thr Tyr Arg Gly Asn
            2105                2110                2115
```

Ser Thr Gly Thr Leu Met Val Phe Phe Gly Asn Val Asp Ser Ser
         2120                2125                2130

Gly Ile Lys His Asn Ile Phe Asn Pro Pro Ile Ile Ala Arg Tyr
         2135                2140                2145

Ile Arg Leu His Pro Thr His Tyr Ser Ile Arg Ser Thr Leu Arg
         2150                2155                2160

Met Glu Leu Met Gly Cys Asp Leu Asn Ser Cys Ser Met Pro Leu
         2165                2170                2175

Gly Met Glu Ser Lys Ala Ile Ser Asp Ala Gln Ile Thr Ala Ser
         2180                2185                2190

Ser Tyr Phe Thr Asn Met Phe Ala Thr Trp Ser Pro Ser Lys Ala
         2195                2200                2205

Arg Leu His Leu Gln Gly Arg Ser Asn Ala Trp Arg Pro Gln Val
         2210                2215                2220

Asn Asn Pro Lys Glu Trp Leu Gln Val Asp Phe Gln Lys Thr Met
         2225                2230                2235

Lys Val Thr Gly Val Thr Thr Gln Gly Val Lys Ser Leu Leu Thr
         2240                2245                2250

Ser Met Tyr Val Lys Glu Phe Leu Ile Ser Ser Ser Gln Asp Gly
         2255                2260                2265

His Gln Trp Thr Leu Phe Phe Gln Asn Gly Lys Val Lys Val Phe
         2270                2275                2280

Gln Gly Asn Gln Asp Ser Phe Thr Pro Val Val Asn Ser Leu Asp
         2285                2290                2295

Pro Pro Leu Leu Thr Arg Tyr Leu Arg Ile His Pro Gln Ser Trp
         2300                2305                2310

Val His Gln Ile Ala Leu Arg Met Glu Val Leu Gly Cys Glu Ala
         2315                2320                2325

Gln Asp Leu Tyr
         2330

<210> SEQ ID NO 5
<211> LENGTH: 1457
<212> TYPE: PRT
<213> ORGANISM: Artificial Sequence
<220> FEATURE:
<223> OTHER INFORMATION: B-domainless human Factor VIII (hBDDF8) with
      signal peptide

<400> SEQUENCE: 5

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser

-continued

```
            115                 120                 125
Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540
```

```
Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960
```

```
Ala Tyr Phe Ser Asp Val Asp Leu Glu Lys Asp Val His Ser Gly Leu
            965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
```

```
                1355                1360                1365
Thr Thr Gln Gly Val Lys Ser Leu Leu Thr Ser Met Tyr Val Lys
        1370                1375                1380

Glu Phe Leu Ile Ser Ser Ser Gln Asp Gly His Gln Trp Thr Leu
        1385                1390                1395

Phe Phe Gln Asn Gly Lys Val Lys Val Phe Gln Gly Asn Gln Asp
        1400                1405                1410

Ser Phe Thr Pro Val Val Asn Ser Leu Asp Pro Pro Leu Leu Thr
        1415                1420                1425

Arg Tyr Leu Arg Ile His Pro Gln Ser Trp Val His Gln Ile Ala
        1430                1435                1440

Leu Arg Met Glu Val Leu Gly Cys Glu Ala Gln Asp Leu Tyr
        1445                1450                1455

<210> SEQ ID NO 6
<211> LENGTH: 1438
<212> TYPE: PRT
<213> ORGANISM: Artificial Sequence
<220> FEATURE:
<223> OTHER INFORMATION: B-domainless human Factor VIII (hBDDF8)
      without native signal peptide

<400> SEQUENCE: 6

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255
```

```
Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
```

```
                    675                 680                 685
Ile Leu Gly Cys His Asn Ser Asp Phe Arg Asn Arg Gly Met Thr Ala
    690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Ser Lys Asn Asn Ala
                725                 730                 735
Ile Glu Pro Arg Ser Phe Ser Gln Asn Pro Val Leu Lys Arg His
                740                 745                 750
Gln Arg Glu Ile Thr Arg Thr Thr Leu Gln Ser Asp Gln Glu Glu Ile
                755                 760                 765
Asp Tyr Asp Asp Thr Ile Ser Val Glu Met Lys Lys Glu Asp Phe Asp
                770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Ser Pro His Val Leu Arg Asn Arg Ala Gln Ser Gly Ser
                820                 825                 830
Val Pro Gln Phe Lys Lys Val Val Phe Gln Glu Phe Thr Asp Gly Ser
                835                 840                 845
Phe Thr Gln Pro Leu Tyr Arg Gly Glu Leu Asn Glu His Leu Gly Leu
                850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
Ser Tyr Glu Glu Asp Gln Arg Gln Gly Ala Glu Pro Arg Lys Asn Phe
                900                 905                 910
Val Lys Pro Asn Glu Thr Lys Thr Tyr Phe Trp Lys Val Gln His His
                915                 920                 925
Met Ala Pro Thr Lys Asp Glu Phe Asp Cys Lys Ala Trp Ala Tyr Phe
                930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                965                 970                 975
Val Thr Val Gln Glu Phe Ala Leu Phe Phe Thr Ile Phe Asp Glu Thr
                980                 985                 990
Lys Ser Trp Tyr Phe Thr Glu Asn Met Glu Arg Asn Cys Arg Ala Pro
                995                 1000                1005
Cys Asn Ile Gln Met Glu Asp Pro Thr Phe Lys Glu Asn Tyr Arg
                1010                1015                1020
Phe His Ala Ile Asn Gly Tyr Ile Met Asp Thr Leu Pro Gly Leu
                1025                1030                1035
Val Met Ala Gln Asp Gln Arg Ile Arg Trp Tyr Leu Leu Ser Met
                1040                1045                1050
Gly Ser Asn Glu Asn Ile His Ser Ile His Phe Ser Gly His Val
                1055                1060                1065
Phe Thr Val Arg Lys Lys Glu Glu Tyr Lys Met Ala Leu Tyr Asn
                1070                1075                1080
Leu Tyr Pro Gly Val Phe Glu Thr Val Glu Met Leu Pro Ser Lys
                1085                1090                1095
```

Ala Gly Ile Trp Arg Val Glu Cys Leu Ile Gly Glu His Leu His
1100                1105                1110

Ala Gly Met Ser Thr Leu Phe Leu Val Tyr Ser Asn Lys Cys Gln
1115                1120                1125

Thr Pro Leu Gly Met Ala Ser Gly His Ile Arg Asp Phe Gln Ile
1130                1135                1140

Thr Ala Ser Gly Gln Tyr Gly Gln Trp Ala Pro Lys Leu Ala Arg
1145                1150                1155

Leu His Tyr Ser Gly Ser Ile Asn Ala Trp Ser Thr Lys Glu Pro
1160                1165                1170

Phe Ser Trp Ile Lys Val Asp Leu Leu Ala Pro Met Ile Ile His
1175                1180                1185

Gly Ile Lys Thr Gln Gly Ala Arg Gln Lys Phe Ser Ser Leu Tyr
1190                1195                1200

Ile Ser Gln Phe Ile Ile Met Tyr Ser Leu Asp Gly Lys Lys Trp
1205                1210                1215

Gln Thr Tyr Arg Gly Asn Ser Thr Gly Thr Leu Met Val Phe Phe
1220                1225                1230

Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser
1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
1280                1285                1290

Ala Gln Ile Thr Ala Ser Ser Tyr Phe Thr Asn Met Phe Ala Thr
1295                1300                1305

Trp Ser Pro Ser Lys Ala Arg Leu His Leu Gln Gly Arg Ser Asn
1310                1315                1320

Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
1400                1405                1410

Ile His Pro Gln Ser Trp Val His Gln Ile Ala Leu Arg Met Glu
1415                1420                1425

Val Leu Gly Cys Glu Ala Gln Asp Leu Tyr
1430                1435

<210> SEQ ID NO 7
<211> LENGTH: 745
<212> TYPE: PRT
<213> ORGANISM: Artificial Sequence
<220> FEATURE:
<223> OTHER INFORMATION: human factor VIII heavy chain (without signal
     peptide) in hBDDF8

```
<400> SEQUENCE: 7

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415
```

```
Gln Arg Ile Gly Arg Lys Tyr Lys Val Arg Phe Met Ala Tyr Thr
        420             425             430

Asp Glu Thr Phe Lys Thr Arg Glu Ala Ile Gln His Glu Ser Gly Ile
        435             440             445

Leu Gly Pro Leu Leu Tyr Gly Glu Val Gly Asp Thr Leu Leu Ile Ile
    450             455             460

Phe Lys Asn Gln Ala Ser Arg Pro Tyr Asn Ile Tyr Pro His Gly Ile
465             470             475             480

Thr Asp Val Arg Pro Leu Tyr Ser Arg Arg Leu Pro Lys Gly Val Lys
                485             490             495

His Leu Lys Asp Phe Pro Ile Leu Pro Gly Glu Ile Phe Lys Tyr Lys
            500             505             510

Trp Thr Val Thr Val Glu Asp Gly Pro Thr Lys Ser Asp Pro Arg Cys
        515             520             525

Leu Thr Arg Tyr Tyr Ser Ser Phe Val Asn Met Glu Arg Asp Leu Ala
    530             535             540

Ser Gly Leu Ile Gly Pro Leu Leu Ile Cys Tyr Lys Glu Ser Val Asp
545             550             555             560

Gln Arg Gly Asn Gln Ile Met Ser Asp Lys Arg Asn Val Ile Leu Phe
                565             570             575

Ser Val Phe Asp Glu Asn Arg Ser Trp Tyr Leu Thr Glu Asn Ile Gln
            580             585             590

Arg Phe Leu Pro Asn Pro Ala Gly Val Gln Leu Glu Asp Pro Glu Phe
        595             600             605

Gln Ala Ser Asn Ile Met His Ser Ile Asn Gly Tyr Val Phe Asp Ser
    610             615             620

Leu Gln Leu Ser Val Cys Leu His Glu Val Ala Tyr Trp Tyr Ile Leu
625             630             635             640

Ser Ile Gly Ala Gln Thr Asp Phe Leu Ser Val Phe Phe Ser Gly Tyr
                645             650             655

Thr Phe Lys His Lys Met Val Tyr Glu Asp Thr Leu Thr Leu Phe Pro
            660             665             670

Phe Ser Gly Glu Thr Val Phe Met Ser Met Glu Asn Pro Gly Leu Trp
        675             680             685

Ile Leu Gly Cys His Asn Ser Asp Phe Arg Asn Arg Gly Met Thr Ala
    690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
                725             730             735

Ile Glu Pro Arg Ser Phe Ser Gln Asn
            740             745

<210> SEQ ID NO 8
<211> LENGTH: 13
<212> TYPE: PRT
<213> ORGANISM: Artificial Sequence
<220> FEATURE:
<223> OTHER INFORMATION: truncated B-domain in hBDDF8

<400> SEQUENCE: 8

Ser Phe Ser Gln Asn Pro Pro Val Leu Lys Arg His Gln
1               5                   10

<210> SEQ ID NO 9
```

<211> LENGTH: 693
<212> TYPE: PRT
<213> ORGANISM: Artificial Sequence
<220> FEATURE:
<223> OTHER INFORMATION: human FVIII light chain in hBDDF8

<400> SEQUENCE: 9

```
Pro Pro Val Leu Lys Arg His Gln Arg Glu Ile Thr Arg Thr Thr Leu
1               5                   10                  15

Gln Ser Asp Gln Glu Glu Ile Asp Tyr Asp Asp Thr Ile Ser Val Glu
            20                  25                  30

Met Lys Lys Glu Asp Phe Asp Ile Tyr Asp Glu Asp Glu Asn Gln Ser
        35                  40                  45

Pro Arg Ser Phe Gln Lys Lys Thr Arg His Tyr Phe Ile Ala Ala Val
    50                  55                  60

Glu Arg Leu Trp Asp Tyr Gly Met Ser Ser Ser Pro His Val Leu Arg
65                  70                  75                  80

Asn Arg Ala Gln Ser Gly Ser Val Pro Gln Phe Lys Lys Val Val Phe
                85                  90                  95

Gln Glu Phe Thr Asp Gly Ser Phe Thr Gln Pro Leu Tyr Arg Gly Glu
            100                 105                 110

Leu Asn Glu His Leu Gly Leu Leu Gly Pro Tyr Ile Arg Ala Glu Val
        115                 120                 125

Glu Asp Asn Ile Met Val Thr Phe Arg Asn Gln Ala Ser Arg Pro Tyr
    130                 135                 140

Ser Phe Tyr Ser Ser Leu Ile Ser Tyr Glu Glu Asp Gln Arg Gln Gly
145                 150                 155                 160

Ala Glu Pro Arg Lys Asn Phe Val Lys Pro Asn Glu Thr Lys Thr Tyr
                165                 170                 175

Phe Trp Lys Val Gln His His Met Ala Pro Thr Lys Asp Glu Phe Asp
            180                 185                 190

Cys Lys Ala Trp Ala Tyr Phe Ser Asp Val Asp Leu Glu Lys Asp Val
        195                 200                 205

His Ser Gly Leu Ile Gly Pro Leu Leu Val Cys His Thr Asn Thr Leu
    210                 215                 220

Asn Pro Ala His Gly Arg Gln Val Thr Val Gln Glu Phe Ala Leu Phe
225                 230                 235                 240

Phe Thr Ile Phe Asp Glu Thr Lys Ser Trp Tyr Phe Thr Glu Asn Met
                245                 250                 255

Glu Arg Asn Cys Arg Ala Pro Cys Asn Ile Gln Met Glu Asp Pro Thr
            260                 265                 270

Phe Lys Glu Asn Tyr Arg Phe His Ala Ile Asn Gly Tyr Ile Met Asp
        275                 280                 285

Thr Leu Pro Gly Leu Val Met Ala Gln Asp Gln Arg Ile Arg Trp Tyr
    290                 295                 300

Leu Leu Ser Met Gly Ser Asn Glu Asn Ile His Ser Ile His Phe Ser
305                 310                 315                 320

Gly His Val Phe Thr Val Arg Lys Lys Glu Glu Tyr Lys Met Ala Leu
                325                 330                 335

Tyr Asn Leu Tyr Pro Gly Val Phe Glu Thr Val Glu Met Leu Pro Ser
            340                 345                 350

Lys Ala Gly Ile Trp Arg Val Glu Cys Leu Ile Gly Glu His Leu His
        355                 360                 365

Ala Gly Met Ser Thr Leu Phe Leu Val Tyr Ser Asn Lys Cys Gln Thr
    370                 375                 380
```

```
Pro Leu Gly Met Ala Ser Gly His Ile Arg Asp Phe Gln Ile Thr Ala
385                 390                 395                 400

Ser Gly Gln Tyr Gly Gln Trp Ala Pro Lys Leu Ala Arg Leu His Tyr
            405                 410                 415

Ser Gly Ser Ile Asn Ala Trp Ser Thr Lys Glu Pro Phe Ser Trp Ile
            420                 425                 430

Lys Val Asp Leu Leu Ala Pro Met Ile Ile His Gly Ile Lys Thr Gln
            435                 440                 445

Gly Ala Arg Gln Lys Phe Ser Ser Leu Tyr Ile Ser Gln Phe Ile Ile
    450                 455                 460

Met Tyr Ser Leu Asp Gly Lys Lys Trp Gln Thr Tyr Arg Gly Asn Ser
465                 470                 475                 480

Thr Gly Thr Leu Met Val Phe Phe Gly Asn Val Asp Ser Ser Gly Ile
            485                 490                 495

Lys His Asn Ile Phe Asn Pro Pro Ile Ile Ala Arg Tyr Ile Arg Leu
            500                 505                 510

His Pro Thr His Tyr Ser Ile Arg Ser Thr Leu Arg Met Glu Leu Met
            515                 520                 525

Gly Cys Asp Leu Asn Ser Cys Ser Met Pro Leu Gly Met Glu Ser Lys
530                 535                 540

Ala Ile Ser Asp Ala Gln Ile Thr Ala Ser Ser Tyr Phe Thr Asn Met
545                 550                 555                 560

Phe Ala Thr Trp Ser Pro Ser Lys Ala Arg Leu His Leu Gln Gly Arg
            565                 570                 575

Ser Asn Ala Trp Arg Pro Gln Val Asn Asn Pro Lys Glu Trp Leu Gln
            580                 585                 590

Val Asp Phe Gln Lys Thr Met Lys Val Thr Gly Val Thr Thr Gln Gly
            595                 600                 605

Val Lys Ser Leu Leu Thr Ser Met Tyr Val Lys Glu Phe Leu Ile Ser
            610                 615                 620

Ser Ser Gln Asp Gly His Gln Trp Thr Leu Phe Phe Gln Asn Gly Lys
625                 630                 635                 640

Val Lys Val Phe Gln Gly Asn Gln Asp Ser Phe Thr Pro Val Val Asn
            645                 650                 655

Ser Leu Asp Pro Pro Leu Leu Thr Arg Tyr Leu Arg Ile His Pro Gln
            660                 665                 670

Ser Trp Val His Gln Ile Ala Leu Arg Met Glu Val Leu Gly Cys Glu
            675                 680                 685

Ala Gln Asp Leu Tyr
    690

<210> SEQ ID NO 10
<211> LENGTH: 1457
<212> TYPE: PRT
<213> ORGANISM: Artificial Sequence
<220> FEATURE:
<223> OTHER INFORMATION: hHC-cLC with signal peptide

<400> SEQUENCE: 10

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45
```

```
Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
    450                 455                 460
```

```
Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Ser
        755                 760                 765

Lys His His Gln Arg Glu Ile Thr Val Thr Thr Leu Gln Pro Glu Glu
770                 775                 780

Asp Lys Phe Glu Tyr Asp Asp Thr Phe Ser Ile Glu Met Lys Arg Glu
785                 790                 795                 800

Asp Phe Asp Ile Tyr Gly Asp Tyr Glu Asn Gln Gly Leu Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Arg Ser Pro His Ile Leu Arg Asn Arg Ala Gln
        835                 840                 845

Ser Gly Asp Val Gln Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
```

-continued

```
                885                 890                 895
Val Val Thr Phe Lys Asn Gln Ala Ser Arg Pro Tyr Ser Phe Tyr Ser
                900                 905                 910

Ser Leu Ile Ser Tyr Asp Glu Asp Glu Gly Gln Gly Ala Glu Pro Arg
                915                 920                 925

Arg Lys Phe Val Asn Pro Asn Glu Thr Lys Ile Tyr Phe Trp Lys Val
        930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Ile Cys Arg Ser Asn Thr Leu Asn Pro Ala His
                980                 985                 990

Gly Arg Gln Val Thr Val Gln Glu Phe Ala Leu Val Phe Thr Ile Phe
        995                 1000                1005

Asp Glu Thr Lys Ser Trp Tyr Phe Thr Glu Asn Leu Glu Arg Asn
        1010                1015                1020

Cys Arg Ala Pro Cys Asn Val Gln Lys Glu Asp Pro Thr Leu Lys
        1025                1030                1035

Glu Asn Phe Arg Phe His Ala Ile Asn Gly Tyr Val Lys Asp Thr
        1040                1045                1050

Leu Pro Gly Leu Val Met Ala Gln Asp Gln Lys Val Arg Trp Tyr
        1055                1060                1065

Leu Leu Ser Met Gly Ser Asn Glu Asn Ile His Ser Ile His Phe
        1070                1075                1080

Ser Gly His Val Phe Thr Val Arg Lys Lys Glu Glu Tyr Lys Met
        1085                1090                1095

Ala Val Tyr Asn Leu Tyr Pro Gly Val Phe Glu Thr Val Glu Met
        1100                1105                1110

Leu Pro Ser Gln Val Gly Ile Trp Arg Ile Glu Cys Leu Ile Gly
        1115                1120                1125

Glu His Leu Gln Ala Gly Met Ser Thr Leu Phe Leu Val Tyr Ser
        1130                1135                1140

Lys Lys Cys Gln Thr Pro Leu Gly Met Ala Ser Gly His Ile Arg
        1145                1150                1155

Asp Phe Gln Ile Thr Ala Ser Gly Gln Tyr Gly Gln Trp Ala Pro
        1160                1165                1170

Lys Leu Ala Arg Leu His Tyr Ser Gly Ser Ile Asn Ala Trp Ser
        1175                1180                1185

Thr Lys Asp Pro Phe Ser Trp Ile Lys Val Asp Leu Leu Ala Pro
        1190                1195                1200

Met Ile Ile His Gly Ile Met Thr Gln Gly Ala Arg Gln Lys Phe
        1205                1210                1215

Ser Ser Leu Tyr Val Ser Gln Phe Ile Ile Met Tyr Ser Leu Asp
        1220                1225                1230

Gly Asn Lys Trp His Ser Tyr Arg Gly Asn Ser Thr Gly Thr Leu
        1235                1240                1245

Met Val Phe Phe Gly Asn Val Asp Ser Ser Gly Ile Lys His Asn
        1250                1255                1260

Ile Phe Asn Pro Pro Ile Ile Ala Gln Tyr Ile Arg Leu His Pro
        1265                1270                1275

Thr His Tyr Ser Ile Arg Ser Thr Leu Arg Met Glu Leu Leu Gly
        1280                1285                1290
```

```
Cys Asp Phe Asn Ser Cys Ser Met Pro Leu Gly Met Glu Ser Lys
            1295                1300                1305

Ala Ile Ser Asp Ala Gln Ile Thr Ala Ser Ser Tyr Leu Ser Ser
    1310                1315                1320

Met Leu Ala Thr Trp Ser Pro Ser Gln Ala Arg Leu His Leu Gln
1325                1330                1335

Gly Arg Thr Asn Ala Trp Arg Pro Gln Ala Asn Asn Pro Lys Glu
    1340                1345                1350

Trp Leu Gln Val Asp Phe Arg Lys Thr Met Lys Val Thr Gly Ile
1355                1360                1365

Thr Thr Gln Gly Val Lys Ser Leu Leu Ile Ser Met Tyr Val Lys
    1370                1375                1380

Glu Phe Leu Ile Ser Ser Ser Gln Asp Gly His Asn Trp Thr Leu
1385                1390                1395

Phe Leu Gln Asn Gly Lys Val Lys Val Phe Gln Gly Asn Arg Asp
    1400                1405                1410

Ser Ser Thr Pro Val Arg Asn Ala Leu Glu Pro Pro Leu Val Ala
1415                1420                1425

Arg Tyr Val Arg Leu His Pro Gln Ser Trp Ala His His Ile Ala
    1430                1435                1440

Leu Arg Leu Glu Val Leu Gly Cys Asp Thr Gln Gln Pro Ala
1445                1450                1455
```

```
<210> SEQ ID NO 11
<211> LENGTH: 4374
<212> TYPE: DNA
<213> ORGANISM: Artificial Sequence
<220> FEATURE:
<223> OTHER INFORMATION: cDNA of hHC-cLC

<400> SEQUENCE: 11
```

| | | | |
|---|---|---|---|
| atgcaaatag agctctccac ctgcttcttt ctgtgccttt tgcgattctg ctttagtgcc | 60 |
| accagaagat actacctggg tgcagtggaa ctgtcatggg actatatgca agtgatctc | 120 |
| ggtgagctgc ctgtggacgc aagatttcct cctagagtgc caaaatcttt tccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaaagactt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggatagggat | 720 |
| gctgcatctg ctcgtgccct gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca catttcttgt gaggaaccat | 900 |
| cgccaggcgt cctggaaat ctcgccaata actttcctta ctgctcaaac actcttgatg | 960 |
| gaccttggac agtttctact gttttgtcat atctcttccc accaacatga tggcatggaa | 1020 |
| gcttatgtca agtagacag ctgtccagag gaaccccaac tacgaatgaa aaataatgaa | 1080 |

```
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat ggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga atccaccagt ctcaaaacac catcaaaggg aaataaccgt tactactctt    2340
cagccagagg aagacaaatt tgagtatgat gacaccttct caattgaaat gaagagagaa    2400
gattttgaca tctacggcga ctatgaaaat cagggcctcc gcagctttca aaagaaaaca    2460
cgacactatt tcattgctgc agtggagcgt ctctgggatt atgggatgag tagatctccc    2520
catatactaa gaaacagggc tcaaagtggg gatgtccagc agttcaagaa ggtggttttc    2580
caggaattta ctgatggatc ctttactcag cccttatacc gtggagaact gaatgaacac    2640
ttgggactct gggggccata tataagagca gaagttgaag acaatatcgt ggtaactttc    2700
aaaaaccagg cctctcgtcc ctactccttc tattctagtc ttatttctta tgacgaagat    2760
gagggacaag gagcagaacc tagaagaaag tttgtcaacc taatgaaac caaaatttac    2820 ttttggaaag tgcagcatca tatggcaccc actaaagatg agtttgactg caaagcctgg    2880
gcttattttt ctgatgttga tttggagaaa gatgtgcact caggcttgat tggacccctt    2940
ctgatctgcc gcagtaacac actgaaccct gctcatggga gacaagtgac agtgcaggag    3000
tttgccctgg ttttcactat attcgatgag actaagagct ggtacttcac tgaaaacctg    3060
gaaaggaact gtagagctcc ctgcaatgtc cagaaggagg accctactct aaaagaaaac    3120
ttccgcttcc atgcaatcaa cggctatgtg aaggatacac tccctggctt agtaatggct    3180
caggatcaaa aggttcgatg gtatctgctc agcatgggca gcaacgaaaa cattcattcc    3240
attcacttca gtggacatgt gttcactgta cggaaaaaag aggaatataa aatggcagtc    3300
tacaacctct atccaggtgt ttttgagact gtggaaatgc taccatccca agttggaatc    3360
tggcggatag aatgccttat cggcgagcac ctgcaagccg ggatgagcac tctgtttctg    3420
```

-continued

```
gtgtacagca agaagtgtca gactccactg gggatggctt ccggacacat tagagatttt    3480
cagattacag cttcaggaca atatggacag tgggccccaa agctggccag acttcattat    3540
tccggatcaa tcaatgcctg gagcaccaag gatccctttt cctggatcaa ggtggatctc    3600
ttggcaccga tgattattca cggcatcatg acccaggggg cccgccagaa gttctccagc    3660
ctctacgtgt ctcagtttat catcatgtac agtctggatg caacaagtg gcacagttac     3720
cgagggaatt ccacggggac cttaatggtc ttctttggca acgtggattc atctgggatc    3780
aaacacaata ttttaaccc tccgattatt gctcagtaca tccgtttgca cccaacccat     3840
tacagcatcc gcagcactct tcgcatggag ctcttgggct gtgacttcaa cagttgcagc    3900
atgccgctgg ggatggagag taaagcaata tcagatgctc agatcactgc ctcgtcctac    3960
ctaagcagta tgcttgccac ttggtctcct tcccaagccc ggctgcacct gcagggcagg    4020
actaatgcct ggagacctca ggcaaataac ccaaaagagt ggctgcaagt ggacttccgg    4080
aagaccatga agtcacagg aataaccacc caggggtga aatctctcct catcagcatg      4140
tatgtgaagg agttcctcat ctccagtagt caagatggcc ataactggac tctgtttctt    4200
cagaatggca aagtcaaggt cttccaggga accgggact cctccacgcc tgtgcggaac     4260
gctctcgaac ccccgctggt ggctcgctac gtgcgcctgc acccgcagag ctgggcgcac    4320
cacatcgccc tgaggctgga ggtcctgggc tgcgacaccc agcagcccgc ctga          4374
```

<210> SEQ ID NO 12
<211> LENGTH: 1438
<212> TYPE: PRT
<213> ORGANISM: Artificial Sequence
<220> FEATURE:
<223> OTHER INFORMATION: hHC-cLC without signal peptide

<400> SEQUENCE: 12

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
```

```
            195                 200                 205
His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
                275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
                355                 360                 365

Ile Gln Ile Arg Ser Val Ala Lys Lys His Pro Lys Thr Trp Val His
370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
                610                 615                 620
```

```
Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Ser Lys His His
            740                 745                 750

Gln Arg Glu Ile Thr Val Thr Thr Leu Gln Pro Glu Glu Asp Lys Phe
                755                 760                 765

Glu Tyr Asp Asp Thr Phe Ser Ile Glu Met Lys Arg Glu Asp Phe Asp
770                 775                 780

Ile Tyr Gly Asp Tyr Glu Asn Gln Gly Leu Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Arg Ser Pro His Ile Leu Arg Asn Arg Ala Gln Ser Gly Asp
            820                 825                 830

Val Gln Gln Phe Lys Lys Val Val Phe Gln Glu Phe Thr Asp Gly Ser
                835                 840                 845

Phe Thr Gln Pro Leu Tyr Arg Gly Glu Leu Asn Glu His Leu Gly Leu
850                 855                 860

Leu Gly Pro Tyr Ile Arg Ala Glu Val Glu Asp Asn Ile Val Val Thr
865                 870                 875                 880

Phe Lys Asn Gln Ala Ser Arg Pro Tyr Ser Phe Tyr Ser Ser Leu Ile
                885                 890                 895

Ser Tyr Asp Glu Asp Glu Gly Gln Gly Ala Glu Pro Arg Arg Lys Phe
            900                 905                 910

Val Asn Pro Asn Glu Thr Lys Ile Tyr Phe Trp Lys Val Gln His His
                915                 920                 925

Met Ala Pro Thr Lys Asp Glu Phe Asp Cys Lys Ala Trp Ala Tyr Phe
            930                 935                 940

Ser Asp Val Asp Leu Glu Lys Asp Val His Ser Gly Leu Ile Gly Pro
945                 950                 955                 960

Leu Leu Ile Cys Arg Ser Asn Thr Leu Asn Pro Ala His Gly Arg Gln
                965                 970                 975

Val Thr Val Gln Glu Phe Ala Leu Val Phe Thr Ile Phe Asp Glu Thr
                980                 985                 990

Lys Ser Trp Tyr Phe Thr Glu Asn Leu Glu Arg Asn Cys Arg Ala Pro
            995                 1000                1005

Cys Asn Val Gln Lys Glu Asp Pro Thr Leu Lys Glu Asn Phe Arg
    1010                1015                1020

Phe His Ala Ile Asn Gly Tyr Val Lys Asp Thr Leu Pro Gly Leu
    1025                1030                1035
```

```
Val Met Ala Gln Asp Gln Lys Val Arg Trp Tyr Leu Leu Ser Met
    1040            1045                1050
Gly Ser Asn Glu Asn Ile His Ser Ile His Phe Ser Gly His Val
    1055            1060                1065
Phe Thr Val Arg Lys Lys Glu Glu Tyr Lys Met Ala Val Tyr Asn
    1070            1075                1080
Leu Tyr Pro Gly Val Phe Glu Thr Val Glu Met Leu Pro Ser Gln
    1085            1090                1095
Val Gly Ile Trp Arg Ile Glu Cys Leu Ile Gly Glu His Leu Gln
    1100            1105                1110
Ala Gly Met Ser Thr Leu Phe Leu Val Tyr Ser Lys Lys Cys Gln
    1115            1120                1125
Thr Pro Leu Gly Met Ala Ser Gly His Ile Arg Asp Phe Gln Ile
    1130            1135                1140
Thr Ala Ser Gly Gln Tyr Gly Gln Trp Ala Pro Lys Leu Ala Arg
    1145            1150                1155
Leu His Tyr Ser Gly Ser Ile Asn Ala Trp Ser Thr Lys Asp Pro
    1160            1165                1170
Phe Ser Trp Ile Lys Val Asp Leu Leu Ala Pro Met Ile Ile His
    1175            1180                1185
Gly Ile Met Thr Gln Gly Ala Arg Gln Lys Phe Ser Ser Leu Tyr
    1190            1195                1200
Val Ser Gln Phe Ile Ile Met Tyr Ser Leu Asp Gly Asn Lys Trp
    1205            1210                1215
His Ser Tyr Arg Gly Asn Ser Thr Gly Thr Leu Met Val Phe Phe
    1220            1225                1230
Gly Asn Val Asp Ser Ser Gly Ile Lys His Asn Ile Phe Asn Pro
    1235            1240                1245
Pro Ile Ile Ala Gln Tyr Ile Arg Leu His Pro Thr His Tyr Ser
    1250            1255                1260
Ile Arg Ser Thr Leu Arg Met Glu Leu Leu Gly Cys Asp Phe Asn
    1265            1270                1275
Ser Cys Ser Met Pro Leu Gly Met Glu Ser Lys Ala Ile Ser Asp
    1280            1285                1290
Ala Gln Ile Thr Ala Ser Ser Tyr Leu Ser Ser Met Leu Ala Thr
    1295            1300                1305
Trp Ser Pro Ser Gln Ala Arg Leu His Leu Gln Gly Arg Thr Asn
    1310            1315                1320
Ala Trp Arg Pro Gln Ala Asn Asn Pro Lys Glu Trp Leu Gln Val
    1325            1330                1335
Asp Phe Arg Lys Thr Met Lys Val Thr Gly Ile Thr Thr Gln Gly
    1340            1345                1350
Val Lys Ser Leu Leu Ile Ser Met Tyr Val Lys Glu Phe Leu Ile
    1355            1360                1365
Ser Ser Ser Gln Asp Gly His Asn Trp Thr Leu Phe Leu Gln Asn
    1370            1375                1380
Gly Lys Val Lys Val Phe Gln Gly Asn Arg Asp Ser Ser Thr Pro
    1385            1390                1395
Val Arg Asn Ala Leu Glu Pro Pro Leu Val Ala Arg Tyr Val Arg
    1400            1405                1410
Leu His Pro Gln Ser Trp Ala His His Ile Ala Leu Arg Leu Glu
    1415            1420                1425
Val Leu Gly Cys Asp Thr Gln Gln Pro Ala
```

```
                 1430            1435
```

<210> SEQ ID NO 13
<211> LENGTH: 13
<212> TYPE: PRT
<213> ORGANISM: Artificial Sequence
<220> FEATURE:
<223> OTHER INFORMATION: truncated B-domain in hHC-cLC

<400> SEQUENCE: 13

Ser Phe Ser Gln Asn Pro Pro Val Ser Lys His His Gln
1               5                   10

<210> SEQ ID NO 14
<211> LENGTH: 693
<212> TYPE: PRT
<213> ORGANISM: Artificial Sequence
<220> FEATURE:
<223> OTHER INFORMATION: canine FVIII light chain in hHC-cLC

<400> SEQUENCE: 14

Pro Pro Val Ser Lys His His Gln Arg Glu Ile Thr Val Thr Thr Leu
1               5                   10                  15

Gln Pro Glu Glu Asp Lys Phe Glu Tyr Asp Asp Thr Phe Ser Ile Glu
            20                  25                  30

Met Lys Arg Glu Asp Phe Asp Ile Tyr Gly Asp Tyr Glu Asn Gln Gly
        35                  40                  45

Leu Arg Ser Phe Gln Lys Lys Thr Arg His Tyr Phe Ile Ala Ala Val
    50                  55                  60

Glu Arg Leu Trp Asp Tyr Gly Met Ser Arg Ser Pro His Ile Leu Arg
65                  70                  75                  80

Asn Arg Ala Gln Ser Gly Asp Val Gln Gln Phe Lys Lys Val Val Phe
                85                  90                  95

Gln Glu Phe Thr Asp Gly Ser Phe Thr Gln Pro Leu Tyr Arg Gly Glu
            100                 105                 110

Leu Asn Glu His Leu Gly Leu Leu Gly Pro Tyr Ile Arg Ala Glu Val
        115                 120                 125

Glu Asp Asn Ile Val Val Thr Phe Lys Asn Gln Ala Ser Arg Pro Tyr
    130                 135                 140

Ser Phe Tyr Ser Ser Leu Ile Ser Tyr Asp Glu Asp Glu Gly Gln Gly
145                 150                 155                 160

Ala Glu Pro Arg Arg Lys Phe Val Asn Pro Asn Glu Thr Lys Ile Tyr
                165                 170                 175

Phe Trp Lys Val Gln His His Met Ala Pro Thr Lys Asp Glu Phe Asp
            180                 185                 190

Cys Lys Ala Trp Ala Tyr Phe Ser Asp Val Asp Leu Glu Lys Asp Val
        195                 200                 205

His Ser Gly Leu Ile Gly Pro Leu Leu Ile Cys Arg Ser Asn Thr Leu
    210                 215                 220

Asn Pro Ala His Gly Arg Gln Val Thr Val Gln Glu Phe Ala Leu Val
225                 230                 235                 240

Phe Thr Ile Phe Asp Glu Thr Lys Ser Trp Tyr Phe Thr Glu Asn Leu
                245                 250                 255

Glu Arg Asn Cys Arg Ala Pro Cys Asn Val Gln Lys Glu Asp Pro Thr
            260                 265                 270

Leu Lys Glu Asn Phe Arg Phe His Ala Ile Asn Gly Tyr Val Lys Asp
        275                 280                 285

```
Thr Leu Pro Gly Leu Val Met Ala Gln Asp Gln Lys Val Arg Trp Tyr
290                 295                 300
Leu Leu Ser Met Gly Ser Asn Glu Asn Ile His Ser Ile His Phe Ser
305                 310                 315                 320
Gly His Val Phe Thr Val Arg Lys Lys Glu Glu Tyr Lys Met Ala Val
                325                 330                 335
Tyr Asn Leu Tyr Pro Gly Val Phe Glu Thr Val Glu Met Leu Pro Ser
                340                 345                 350
Gln Val Gly Ile Trp Arg Ile Glu Cys Leu Ile Gly Glu His Leu Gln
                355                 360                 365
Ala Gly Met Ser Thr Leu Phe Leu Val Tyr Ser Lys Lys Cys Gln Thr
370                 375                 380
Pro Leu Gly Met Ala Ser Gly His Ile Arg Asp Phe Gln Ile Thr Ala
385                 390                 395                 400
Ser Gly Gln Tyr Gly Gln Trp Ala Pro Lys Leu Ala Arg Leu His Tyr
                405                 410                 415
Ser Gly Ser Ile Asn Ala Trp Ser Thr Lys Asp Pro Phe Ser Trp Ile
                420                 425                 430
Lys Val Asp Leu Leu Ala Pro Met Ile Ile His Gly Ile Met Thr Gln
                435                 440                 445
Gly Ala Arg Gln Lys Phe Ser Ser Leu Tyr Val Ser Gln Phe Ile Ile
450                 455                 460
Met Tyr Ser Leu Asp Gly Asn Lys Trp His Ser Tyr Arg Gly Asn Ser
465                 470                 475                 480
Thr Gly Thr Leu Met Val Phe Phe Gly Asn Val Asp Ser Ser Gly Ile
                485                 490                 495
Lys His Asn Ile Phe Asn Pro Pro Ile Ile Ala Gln Tyr Ile Arg Leu
                500                 505                 510
His Pro Thr His Tyr Ser Ile Arg Ser Thr Leu Arg Met Glu Leu Leu
                515                 520                 525
Gly Cys Asp Phe Asn Ser Cys Ser Met Pro Leu Gly Met Glu Ser Lys
530                 535                 540
Ala Ile Ser Asp Ala Gln Ile Thr Ala Ser Ser Tyr Leu Ser Ser Met
545                 550                 555                 560
Leu Ala Thr Trp Ser Pro Ser Gln Ala Arg Leu His Leu Gln Gly Arg
                565                 570                 575
Thr Asn Ala Trp Arg Pro Gln Ala Asn Asn Pro Lys Glu Trp Leu Gln
                580                 585                 590
Val Asp Phe Arg Lys Thr Met Lys Val Thr Gly Ile Thr Thr Gln Gly
                595                 600                 605
Val Lys Ser Leu Leu Ile Ser Met Tyr Val Lys Glu Phe Leu Ile Ser
                610                 615                 620
Ser Ser Gln Asp Gly His Asn Trp Thr Leu Phe Leu Gln Asn Gly Lys
625                 630                 635                 640
Val Lys Val Phe Gln Gly Asn Arg Asp Ser Ser Thr Pro Val Arg Asn
                645                 650                 655
Ala Leu Glu Pro Pro Leu Val Ala Arg Tyr Val Arg Leu His Pro Gln
                660                 665                 670
Ser Trp Ala His His Ile Ala Leu Arg Leu Glu Val Leu Gly Cys Asp
                675                 680                 685
Thr Gln Gln Pro Ala
690
```

<210> SEQ ID NO 15
<211> LENGTH: 9618
<212> TYPE: DNA
<213> ORGANISM: Artificial Sequence
<220> FEATURE:
<223> OTHER INFORMATION: pANG-CAG-hBDDF8

<400> SEQUENCE: 15

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtgccaac | tccatcacta | 120 |
| ggggttcctt | gtagttaatg | attaacccgc | catgctactt | atttacgtag | ccatgctcta | 180 |
| ggtaccattg | acgtcaataa | tgacgtatgt | tcccatagta | acgccaatag | ggactttcca | 240 |
| ttgacgtcaa | tgggtggagt | atttacggta | aactgcccac | ttggcagtac | atcaagtgta | 300 |
| tcatatgcca | agtacgcccc | ctattgacgt | caatgacgga | aaatggcccg | cctggcatta | 360 |
| tgcccagtac | atgaccttat | gggactttcc | tacttggcag | tacatctacg | tattagtcat | 420 |
| cgctattacc | atgtcgaggc | cacgttctgc | ttcactctcc | ccatctcccc | ccctccccca | 480 |
| cccccaattt | tgtatttatt | tattttttaa | ttattttgtg | cagcgatggg | ggcggggggg | 540 |
| gggggcgcgc | gccaggcggg | gcggggcggg | gcgaggggcg | gggcggggcg | aggcggagag | 600 |
| gtgcggcggc | agccaatcag | agcggcgcgc | tccgaaagtt | tccttttatg | gcgaggcggc | 660 |
| ggcggcggcg | gccctataaa | aagcgaagcg | cgcggcgggc | gggagcaagc | tctagccgcg | 720 |
| cggcgggcgg | gagtcgctgc | gcgctgcctt | cgccccgtgc | cccgctccgc | cgccgcctcg | 780 |
| cgccgcccgc | cccggctctg | actgaccgcg | ttactcccac | aggtgagcgg | gcgggacggc | 840 |
| ccttctcctc | cgggctgtaa | ttagcgcttg | gtttaatgac | ggcttgtttc | ttttctgtgg | 900 |
| ctgcgtgaaa | gccttgaggg | gctccgggag | ggccctttgt | gcgggggggag | cggctcgggg | 960 |
| ctgtccgcgg | gggacggct | gccttcgggg | gggacggggc | agggcggggt | tcggcttctg | 1020 |
| gcgtgtgacc | ggcggctcta | gagcctctgc | taaccatgtt | catgccttct | tctttttcct | 1080 |
| acagctcctg | ggcaacgtgc | tggttattgt | gctgtctcat | cattttggca | aagaattgat | 1140 |
| ccacactttt | tcttttctc | acaggtatc | gattccacca | tgcaaataga | gctctccacc | 1200 |
| tgcttctttc | tgtgccttt | gcgattctgc | tttagtgcca | ccagaagata | ctacctgggt | 1260 |
| gcagtggaac | tgtcatggga | ctatatgcaa | agtgatctcg | gtgagctgcc | tgtggacgca | 1320 |
| agatttcctc | ctagagtgcc | aaaatctttt | ccattcaaca | cctcagtcgt | gtacaaaaag | 1380 |
| actctgtttg | tagaattcac | ggatcacctt | ttcaacatcg | ctaagccaag | gccaccctgg | 1440 |
| atgggtctgc | taggtcctac | catccaggct | gaggtttatg | atacagtggt | cattacactt | 1500 |
| aagaacatgg | cttcccatcc | tgtcagtctt | catgctgttg | gtgtatccta | ctggaaagct | 1560 |
| tctgagggag | ctgaatatga | tgatcagacc | agtcaaaggg | agaaagaaga | tgataaagtc | 1620 |
| ttccctggtg | gaagccatac | atatgtctgg | caggtcctga | agagaatgg | tccaatggcc | 1680 |
| tctgacccac | tgtgccttac | ctactcatat | ctttctcatg | tggacctggt | aaaagacttg | 1740 |
| aattcaggcc | tcattggagc | cctactagta | tgtagagaag | ggagtctggc | caaggaaaag | 1800 |
| acacagacct | tgcacaaatt | tatactactt | tttgctgtat | ttgatgaagg | gaaaagttgg | 1860 |
| cactcagaaa | caaagaactc | cttgatgcag | ataggggatg | ctgcatctgc | tcgggcctgg | 1920 |
| cctaaaatgc | acacagtcaa | tggttatgta | aacaggtctc | tgccaggtct | gattggatgc | 1980 |
| cacaggaaat | cagtctattg | gcatgtgatt | ggaatgggca | ccactcctga | agtgcactca | 2040 |
| atattcctcg | aaggtcacac | atttcttgtg | aggaaccatc | gccaggcgtc | cttggaaatc | 2100 |

```
tcgccaataa ctttccttac tgctcaaaca ctcttgatgg accttggaca gtttctactg    2160
ttttgtcata tctcttccca ccaacatgat ggcatggaag cttatgtcaa agtagacagc    2220
tgtccagagg aaccccaact acgaatgaaa ataatgaag aagcggaaga ctatgatgat     2280
gatcttactg attctgaaat ggatgtggtc aggtttgatg atgacaactc tccttccttt    2340
atccaaattc gctcagttgc caagaagcat cctaaaactt gggtacatta cattgctgct    2400
gaagaggagg actgggacta tgctccctta gtcctcgccc ccgatgacag aagttataaa    2460
agtcaatatt tgaacaatgg ccctcagcgg attggtagga agtacaaaaa agtccgattt    2520
atggcataca cagatgaaac ctttaagact cgtgaagcta ttcagcatga atcaggaatc    2580
ttgggacctt tactttatgg ggaagttgga gacacactgt tgattatatt taagaatcaa    2640
gcaagcagac catataacat ctaccctcac ggaatcactg atgtccgtcc tttgtattca    2700
aggagattac caaaaggtgt aaaacatttg aaggattttc caattctgcc aggagaaata    2760
ttcaaatata aatggacagt gactgtagaa gatgggccaa ctaaatcaga tcctcggtgc    2820
ctgacccgct attactctag tttcgttaat atggagagag atctagcttc aggactcatt    2880
ggccctctcc tcatctgcta caaagaatct gtagatcaaa gaggaaacca gataatgtca    2940
gacaagagga atgtcatcct gttttctgta tttgatgaga accgaagctg gtacctcaca    3000
gagaatatac aacgctttct ccccaatcca gctggagtgc agcttgagga tccagagttc    3060
caagcctcca acatcatgca cagcatcaat ggctatgttt ttgatagttt gcagttgtca    3120
gtttgtttgc atgaggtggc atactggtac attctaagca ttggagcaca gactgacttc    3180 cttttctgtct tcttctctgg atataccttc aaacacaaaa tggtctatga agacacactc    3240
accctattcc cattctcagg agaaactgtc ttcatgtcga tggaaaaccc aggtctatgg    3300
attctggggt gccacaactc agactttcgg aacagaggca tgaccgcctt actgaaggtt    3360
tctagttgtg acaagaacac tggtgattat tacgaggaca gttatgaaga tatttcagca    3420
tacttgctga gtaaaaacaa tgccattgaa ccaagaagct ctcccagaa tccaccagtc     3480 ttgaaacgcc atcaacgcga ataactcgt actactcttc agtcagatca agaggaaatt    3540
gactatgatg ataccatatc agttgaaatg aagaaggaag attttgacat ttatgatgag    3600
gatgaaaatc agagcccccg cagctttcaa agaaaacac gacactattt tattgctgca    3660
gtggagaggc tctgggatta tgggatgagt agctccccac atgttctaag aaacagggct    3720
cagagtggca gtgtccctca gttcaagaaa gttgttttcc aggaatttac tgatggctcc    3780
tttactcagc cctataccg tggagaacta aatgaacatt tgggactcct ggggccatat    3840
ataagagcag aagttgaaga taatatcatg gtaactttca gaaatcaggc ctctcgtccc    3900
tattccttct attctagcct tatttcttat gaggaagatc agaggcaagg agcagaacct    3960
agaaaaaact ttgtcaagcc taatgaaacc aaaacttact tttggaaagt gcaacatcat    4020
atggcaccca ctaaagatga gtttgactgc aaagcctggg cttatttctc tgatgttgac    4080
ctggaaaaag atgtgcactc aggcctgatt ggacccttc tggtctgcca cactaacaca    4140
ctgaaccctg ctcatgggag acaagtgaca gtacaggaat tgctctgtt tttcaccatc    4200 tttgatgaga ccaaaagctg gtacttcact gaaaatatgg aaagaaactg cagggctccc    4260
tgcaatatcc agatggaaga tcccactttt aaagagaatt atcgcttcca tgcaatcaat    4320
ggctacataa tggatacact acctggctta gtaatggctc aggatcaaag gattcgatgg    4380
tatctgctca gcatgggcag caatgaaaac atccattcta ttcatttcag tggacatgtg    4440
ttcactgtac gaaaaaaga ggagtataaa atggcactgt acaatctcta tccaggtgtt    4500
```

```
tttgagacag tggaaatgtt accatccaaa gctggaattt ggcgggtgga atgccttatt    4560
ggcgagcatc tacatgctgg gatgagcaca cttttctgg tgtacagcaa taagtgtcag    4620
actcccctgg gaatggcttc tggacacatt agagattttc agattacagc ttcaggacaa    4680
tatgacagt gggccccaaa gctggccaga cttcattatt ccggatcaat caatgcctgg    4740
agcaccaagg agccctttc ttggatcaag gtggatctgt tggcaccaat gattattcac    4800
ggcatcaaga cccagggtgc ccgtcagaag ttctccagcc tctacatctc tcagtttatc    4860
atcatgtata gtcttgatgg gaagaagtgg cagacttatc gaggaaattc cactggaacc    4920
ttaatggtct tctttggcaa tgtggattca tctgggataa acacaatat ttttaaccct    4980
ccaattattg ctcgatacat ccgtttgcac ccaactcatt atagcattcg cagcactctt    5040
cgcatggagt tgatgggctg tgattaaat agttgcagca tgccattggg aatgagagt    5100
aaagcaatat cagatgcaca gattactgct tcatcctact ttaccaatat gtttgccacc    5160
tggtctcctt caaaagctcg acttcacctc caagggagga gtaatgcctg gagacctcag    5220
gtgaataatc caaagagtg gctgcaagtg acttccaga agacaatgaa agtcacagga    5280
gtaactactc agggagtaaa atctctgctt accagcatgt atgtgaagga gttcctcatc    5340
tccagcagtc aagatggcca tcagtggact ctctttttc agaatggcaa agtaaaggtt    5400
tttcagggaa atcaagactc cttcacacct gtggtgaact ctctagaccc accgttactg    5460
actcgctacc ttcgaattca ccccagagt tgggtgcacc agattgccct gaggatggag    5520
gttctgggct gcgaggcaca ggacctctac tgactcgaga ataaaagatc agagctctag    5580
agatctgtgt gttggttttt tgtgtgcggc cgggatctga ggaacccta gtgatggagt    5640
tggccactcc ctctctgcgc gctcgctcgc tcactgaggc cgcccgggca agcccgggc    5700
gtcgggcgac ctttggtcgc ccggcctcag tgagcgagcg agcgcgcaga gagggagtgg    5760
ccaaccccc cccccccccc cctgcaggcg attctcttgt ttgctccaga ctctcaggca    5820
atgacctgat agcctttgta gagacctctc aaaaatagct accctctccg gcatgaattt    5880
atcagctaga acggttgaat atcatattga tggtgatttg actgtctccg gcctttctca    5940
cccgtttgaa tctttaccta cacattactc aggcattgca tttaaaatat atgagggttc    6000
taaaaatttt tatccttgcg ttgaaataaa ggcttctccc gcaaaagtat tacagggtca    6060
taatgttttt ggtacaaccg atttagcttt atgctctgag gctttattgc ttaatttgc    6120
taattctttg ccttgcctgt atgatttatt ggatgttgga attcctgatg cggtattttc    6180
tccttacgca tctgtgcggt atttcacacc gcatatggtg cactctcagt acaatctgct    6240
ctgatgccgc atagttaagc cagccccgac acccgccaac acccgctgac gcgccctgac    6300
gggcttgtct gctcccggca tccgcttaca gacaagctgt gaccgtctcc gggagctgca    6360
tgtgtcagag gttttcaccg tcatcaccga aacgcgcgag acgaaagggc ctcgtgatac    6420
gcctatttt ataggttaat gtcatgataa taatggtttc ttagacgtca ggtggcactt    6480
ttcggggaaa tgtgcgcgga accctattt gtttattttt ctaaatacat tcaaatatgt    6540
atccgctcat gagacaataa ccctgataaa tgcttcaata atattgaaaa aggaagagta    6600
tgagtattca acatttccgt gtcgccctta ttccctttt gcggcattt tgccttcctg    6660
ttttgctca cccagaaacg ctggtgaaag taaaagatgc tgaagatcag ttgggtgcac    6720
gagtgggtta catcgaactg gatctcaaca gcggtaagat ccttgagagt tttcgccccg    6780
aagaacgttt tccaatgatg agcactttta aagttctgct atgtgcgcg gtattatccc    6840
```

```
gtattgacgc cgggcaagag caactcggtc gccgcataca ctattctcag aatgacttgg    6900
ttgagtactc accagtcaca gaaaagcatc ttacggatgg catgacagta agagaattat    6960
gcagtgctgc cataaccatg agtgataaca ctgcggccaa cttacttctg acaacgatcg    7020
gaggaccgaa ggagctaacc gcttttttgc acaacatggg ggatcatgta actcgccttg    7080
atcgttggga accggagctg aatgaagcca taccaaacga cgagcgtgac accacgatgc    7140
ctgtagcaat ggcaacaacg ttgcgcaaac tattaactgg cgaactactt actctagctt    7200
cccggcaaca attaatagac tggatggagg cggataaagt tgcaggacca cttctgcgct    7260
cggcccttcc ggctggctgg tttattgctg ataaatctgg agccggtgag cgtgggtctc    7320
gcggtatcat tgcagcactg gggccagatg gtaagccctc ccgtatcgta gttatctaca    7380
cgacggggag tcaggcaact atggatgaac gaaatagaca gatcgctgag ataggtgcct    7440
cactgattaa gcattggtaa ctgtcagacc aagtttactc atatatactt tagattgatt    7500
taaaacttca ttttaattt aaaaggatct aggtgaagat cctttttgat aatctcatga    7560
ccaaaatccc ttaacgtgag ttttcgttcc actgagcgtc agaccccgta gaaaagatca    7620
aaggatcttc ttgagatcct tttttctgc gcgtaatctg ctgcttgcaa acaaaaaaac    7680
caccgctacc agcggtggtt tgtttgccgg atcaagagct accaactctt tttccgaagg    7740
taactggctt cagcagagcg cagataccaa atactgtcct tctagtgtag ccgtagttag    7800
gccaccactt caagaactct gtagcaccgc ctacatacct cgctctgcta atcctgttac    7860
cagtggctgc tgccagtggc gataagtcgt gtcttaccgg gttggactca agacgatagt    7920
taccggataa ggcgcagcgg tcgggctgaa cggggggttc gtgcacacag cccagcttgg    7980
agcgaacgac ctacaccgaa ctgagatacc tacagcgtga gctatgagaa agcgccacgc    8040
ttcccgaagg gagaaaggcg gacaggtatc cggtaagcgg cagggtcgga acaggagagc    8100
gcacgaggga gcttccaggg ggaaacgcct ggtatcttta tagtcctgtc gggtttcgcc    8160
acctctgact tgagcgtcga ttttttgtgat gctcgtcagg gggggcggagc ctatggaaaa    8220 acgccagcaa cgcggccttt ttacggttcc tggccttttg ctggccttt gctcacatgt    8280 tctttcctgc gttatcccct gattctgtgg ataaccgtat taccgccttt gagtgagctg    8340
ataccgctcg ccgcagccga acgaccgagc gcagcgagtc agtgagcgag gaagcggaag    8400
agcgcccaat acgcaaaccg cctctccccg cgcgttggcc gattcattaa tgcagaattc    8460
ccatcatcaa taatatacct tattttggat tgaagccaat atgataatga gggggtggag    8520
tttgtgacgt ggcgcgggc gtgggaacgg ggcgggtgac gtagtagtct ctagaggtcc    8580
ccagcgacct tgacgggcat ctgcccggca tttctgacag cttttgtgaac tgggtggccg    8640 agaaggaatg ggagttgccg ccagattctg acatggatct gaatctgatt gagcaggcac    8700
ccctgaccgt ggccgagaag ctgcatcgct ggcgtaatag cgaagaggcc cgcaccgatc    8760
gcccttccca acagttgcgc agcctgaatg gcgaatggcg attccgttgc aatggctggc    8820
ggtaatattg ttctggatat taccagcaag gccgatagtt tgagttcttc tactcaggca    8880
agtgatgtta ttactaatca agaagtatt gcgacaacgg ttaatttgcg tgatggacag    8940
actcttttac tcggtggcct cactgattat aaaaacactt ctcaggattc tggcgtaccg    9000
ttcctgtcta aaatcccttt aatcggcctc ctgtttagct cccgctctga ttctaacgag    9060
gaaagcacgt tatacgtgct cgtcaaagca accatagtac gcgccctgta gcggcgcatt    9120
aagcgcggcg ggtgtggtgg ttacgcgcag cgtgaccgct acacttgcca gcgccctagc    9180
gcccgctcct ttcgctttct tcccttcctt tctcgccacg ttcgccggcg aacgtggcga    9240
```

-continued

```
gaaaggaagg gaagaaagcg aaaggagcgg gcgctagggc gctggcaagt gtagcggtca   9300
cgctgcgcgt aaccaccaca cccgccgcgc ttaatgcgcc gctacagggc gcgtcccatt   9360
cgccattcag gctgcgcaac tgttgggaag ggcgatcggt gcgggcctct tcgctattac   9420
gccagctggc gaaaggggga tgtgctgcaa ggcgattaag ttgggtaacg ccagggtttt   9480
cccagtcacg acgttgtaaa acgacggcca gtgaattagg ttaattaagg cacacccgcc   9540
gcgcttaatg cgccgctaca gggcgcgtcc cattcgccat tcaggctgcg caactgttgg   9600
gaagggcgat cggtgcgg                                                 9618
```

<210> SEQ ID NO 16
<211> LENGTH: 791
<212> TYPE: PRT
<213> ORGANISM: Artificial Sequence
<220> FEATURE:
<223> OTHER INFORMATION: hBDDF8 sequence in FIG. 2

<400> SEQUENCE: 16

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285
```

-continued

```
Phe Leu Glu Gly His Thr Phe Leu Val Arg Asn His Arg Gln Ala Ser
    290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                    325                 330                 335
Asp Gly Met Glu Ala Tyr Val Lys Val Asp Ser Cys Pro Glu Glu Pro
                340                 345                 350
Gln Leu Arg Met Lys Asn Asn Glu Ala Glu Asp Tyr Asp Asp Asp
            355                 360                 365
Leu Thr Asp Ser Glu Met Asp Val Val Arg Phe Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                    405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
            435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                    485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                    565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
            595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                    645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
```

```
                    705                 710                 715                 720
            Met Thr Ala Leu Leu Lys Val Ser Ser Cys Asp Lys Asn Thr Gly Asp
                            725                 730                 735

Tyr Tyr Glu Asp Ser Tyr Glu Asp Ile Ser Ala Tyr Leu Leu Ser Lys
                            740                 745                 750

Asn Asn Ala Ile Glu Pro Arg Ser Phe Ser Gln Asn Pro Pro Val Leu
                            755                 760                 765

Lys Arg His Gln Arg Glu Ile Thr Arg Thr Thr Leu Gln Ser Asp Gln
                            770                 775                 780

Glu Glu Ile Asp Tyr Asp Asp
            785                 790

<210> SEQ ID NO 17
<211> LENGTH: 791
<212> TYPE: PRT
<213> ORGANISM: Artificial Sequence
<220> FEATURE:
<223> OTHER INFORMATION: hBDDF8 sequence with substitutions in FIG. 2

<400> SEQUENCE: 17

Met Gln Ile Glu Leu Ser Thr Cys Phe Phe Leu Cys Leu Leu Arg Phe
1               5                   10                  15

Cys Phe Ser Lys Val Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Leu Pro Phe Asn Thr Ser Val Val
        50                  55                  60

Tyr Lys Lys Thr Val Phe Val Glu Phe Thr Asp His Leu Phe Asn Val
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Phe Ser His Val Asp Leu Val Lys Asp Leu Asn Ser Gly Leu Ile
                180                 185                 190

Gly Ala Leu Leu Val Cys Lys Glu Gly Ser Leu Ala Lys Glu Lys Thr
            195                 200                 205

Gln Thr Leu Gln Lys Phe Val Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Lys Lys Ser Val
                260                 265                 270

Tyr Trp His Val Ile Gly Met Gly Thr Thr Pro Glu Val His Ser Ile
```

```
             275                 280                 285
Phe Leu Glu Gly His Thr Phe Leu Val Arg Asn His Arg Gln Ala Ser
        290                 295                 300
Leu Glu Ile Ser Pro Val Thr Phe Leu Thr Ala Gln Thr Phe Leu Met
305                 310                 315                 320
Asp Leu Gly Gln Phe Leu Leu Phe Cys His Ile Pro Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Glu Ala Glu Asp Tyr Asp Asp Asp
                355                 360                 365
Leu Thr Asp Ser Glu Met Asp Val Val Ser Phe Asp Asp Asp Asn Ser
        370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
        450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
                515                 520                 525
Lys Tyr Lys Trp Thr Val Thr Val Glu Asp Gly Pro Thr Lys Ser Asp
        530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
                595                 600                 605
Asn Met Gln Arg Phe Leu Pro Asn Pro Ala Gly Val Gln Leu Glu Asp
        610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Val Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
        690                 695                 700
```

```
Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
        740                 745                 750

Asn Asn Ala Ile Glu Pro Arg Ser Phe Ser Gln Asn Pro Pro Val Leu
    755                 760                 765

Lys Arg His Gln Arg Glu Ile Thr Arg Thr Thr Leu Gln Ser Asp Gln
770                 775                 780

Glu Glu Ile Asp Tyr Asp Asp
785                 790
```

<210> SEQ ID NO 18
<211> LENGTH: 8106
<212> TYPE: DNA
<213> ORGANISM: Artificial Sequence
<220> FEATURE:
<223> OTHER INFORMATION: pANG-TTR-hBDDF8

<400> SEQUENCE: 18

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct acgcgtgtct gtctgcacat tcgtagagc gagtgttccg atactctaat   180
ctccctaggc aaggttcata tttgtgtagg ttacttattc tccttttgtt gactaagtca   240
ataatcagaa tcagcaggtt tggagtcagc ttggcaggga tcagcagcct gggttggaag   300
gagggggtat aaaagcccct tcaccaggag aagccgtcac acagatccac aagctcctgc   360
tagcaggtaa gtgccgtgtg tggttcccgc gggcctggcc tctttacggg ttatggccct   420
tgcgtgcctt gaattactga cactgacatc cactttttct ttttctccac aggtatcgat   480
gccaccatgc aaatagagct ctccacctgc ttctttctgt gccttttgcg attctgcttt   540
agtgccacca agatatacta cctgggtgca gtggaactgt catgggacta tatgcaaagt   600
gatctcggtg agctgcctgt ggacgcaaga tttcctccta gagtgccaaa atcttttcca   660
ttcaacacct cagtcgtgta caaaaagact ctgtttgtag aattcacgga tcaccttttc   720
aacatcgcta agccaaggcc accctggatg gtctgctag tcctaccat ccaggctgag   780
gtttatgata cagtggtcat tacacttaag aacatggctt cccatcctgt cagtcttcat   840
gctgttggtg tatcctactg gaaagcttct gagggagctg aatatgatga tcagaccagt   900
caaagggaga agaagatga taaagtcttc cctggtggaa gccatacata tgtctggcag   960
gtcctgaaag agaatggtcc aatggcctct gacccactgt gccttaccta ctcatatctt  1020
tctcatgtgg acctggtaaa agacttgaat tcaggcctca ttggagccct actagtatgt  1080
agagaaggga gtctggccaa ggaaaagaca cagaccttgc acaaatttat actacttttt  1140
gctgtatttg atgaagggaa aagttggcac tcagaaacaa gaactccttt gatgcaggat  1200
agggatgctg catctgctcg ggcctggcct aaaatgcaca cagtcaatgg ttatgtaaac  1260
aggtctctgc caggtctgat tggatgccac aggaaatcag tctattggca tgtgattgga  1320
atgggcacca ctcctgaagt gcactcaata ttcctcgaag gtcacacatt tcttgtgagg  1380
aaccatcgcc aggcgtcctt ggaaatctcg ccaataactt tccttactgc tcaaacactc  1440
ttgatggacc ttggacagtt tctactgttt tgtcatatct cttcccacca acatgatggc  1500
```

```
atggaagctt atgtcaaagt agacagctgt ccagaggaac cccaactacg aatgaaaaat    1560
aatgaagaag cggaagacta tgatgatgat cttactgatt ctgaaatgga tgtggtcagg    1620
tttgatgatg acaactctcc ttcctttatc caaattcgct cagttgccaa gaagcatcct    1680
aaaacttggg tacattacat tgctgctgaa gaggaggact gggactatgc tcccttagtc    1740 ctcgccccg atgacagaag ttataaaagt caatatttga acaatggccc tcagcggatt     1800
ggtaggaagt acaaaaaagt ccgatttatg catacacag atgaaaccctt taagactcgt    1860 gaagctattc agcatgaatc aggaatcttg ggacctttac tttatgggga agttggagac    1920
acactgttga ttatatttaa gaatcaagca agcagaccat ataacatcta ccctcacgga    1980
atcactgatg tccgtccttt gtattcaagg agattaccaa aaggtgtaaa acatttgaag    2040
gattttccaa ttctgccagg agaaatattc aaatataaat ggacagtgac tgtagaagat    2100
gggccaacta aatcagatcc tcggtgcctg acccgctatt actctagttt cgttaatatg    2160
gagagagatc tagcttcagg actcattggc cctctcctca tctgctacaa agaatctgta    2220
gatcaaagag gaaaccagat aatgtcagac aagaggaatg tcatcctgtt ttctgtattt    2280
gatgagaacc gaagctggta cctcacagag aatatacaac gctttctccc caatccagct    2340
ggagtgcagc ttgaggatcc agagttccaa gcctccaaca tcatgcacag catcaatggc    2400
tatgtttttg atagtttgca gttgtcagtt tgtttgcatg aggtggcata ctggtacatt    2460
ctaagcattg gagcacagac tgacttcctt tctgtcttct tctctggata tccttcaaa    2520 cacaaaatgg tctatgaaga cacactcacc ctattcccat tctcaggaga aactgtcttc    2580
atgtcgatgg aaaacccagg tctatggatt ctggggtgcc acaactcaga ctttcggaac    2640
agaggcatga ccgccttact gaaggtttct agttgtgaca gaacactgg tgattattac    2700 gaggacagtt atgaagatat ttcagcatac ttgctgagta aaaacaatgc cattgaacca    2760
agaagcttct cccagaatcc accagtcttg aaacgccatc aacgcgaaat aactcgtact    2820
actcttcagt cagatcaaga ggaaattgac tatgatgata ccatatcagt tgaaatgaag    2880
aaggaagatt ttgacattta tgatgaggat gaaaatcaga gccccccgcag ctttcaaaag    2940 aaaacacgac actatttttat tgctgcagtg gagaggctct gggattatgg gatgagtagc    3000
tccccacatg ttctaagaaa cagggctcag agtggcagtg tccctcagtt caagaaagtt    3060
gttttccagg aatttactga tggctccttt actcagccct ataccgtgg agaactaaat    3120 gaacatttgg gactcctggg gccatatata agagcagaag ttgaagataa tatcatggta    3180
actttcagaa atcaggcctc tcgtccctat tccttctatt ctagccttat ttcttatgag    3240
gaagatcaga ggcaaggagc agaacctaga aaaaactttg tcaagcctaa tgaaaccaaa    3300
acttactttt ggaaagtgca acatcatatg gcacccacta aagatgagtt tgactgcaaa    3360
gcctgggctt atttctctga tgttgacctg gaaaaagatg tgcactcagg cctgattgga    3420
ccccttctgg tctgccacac taacacactg aaccctgctc atgggagaca agtgacagta    3480
caggaatttg ctctgttttt caccatcttt gatgagacca aaagctggta cttcactgaa    3540
aatatggaaa gaaactgcag ggctccctgc aatatccaga tggaagatcc cactttaaa    3600 gagaattatc gcttccatgc aatcaatggc tacataatgg atacactacc tggcttagta    3660
atggctcagg atcaaaggat tcgatggtat ctgctcagca tgggcagcaa tgaaaacatc    3720
cattctattc atttcagtgg acatgtgttc actgtacgaa aaaagagga gtataaaatg    3780 gcactgtaca atctctatcc aggtgttttt gagacagtgg aaatgttacc atccaaagct    3840
ggaatttggc gggtggaatg ccttattggc gagcatctac atgctgggat gagcacactt    3900
```

```
tttctggtgt acagcaataa gtgtcagact cccctgggaa tggcttctgg acacattaga   3960
gattttcaga ttacagcttc aggacaatat ggacagtggg ccccaaagct ggccagactt   4020
cattattccg gatcaatcaa tgcctggagc accaaggagc cctttcttg gatcaaggtg    4080
gatctgttgg caccaatgat tattcacggc atcaagaccc agggtgcccg tcagaagttc   4140
tccagcctct acatctctca gtttatcatc atgtatagtc ttgatgggaa gaagtggcag   4200
acttatcgag gaaattccac tggaacctta atggtcttct ttggcaatgt ggattcatct   4260
gggataaaac acaatatttt taaccctcca attattgctc gatacatccg tttgcaccca   4320
actcattata gcattcgcag cactcttcgc atggagttga tgggctgtga tttaaatagt   4380
tgcagcatgc cattgggaat ggagagtaaa gcaatatcag atgcacagat tactgcttca   4440
tcctacttta ccaatatgtt tgccacctgg tctccttcaa aagctcgact tcacctccaa   4500
gggaggagta atgcctggag acctcaggtg aataatccaa aagagtggct gcaagtggac   4560
ttccagaaga caatgaaagt cacaggagta actactcagg gagtaaaatc tctgcttacc   4620
agcatgtatg tgaaggagtt cctcatctcc agcagtcaag atggccatca gtggactctc   4680
ttttttcaga atggcaaagt aaaggttttt cagggaaatc aagactcctt cacacctgtg   4740
gtgaactctc tagacccacc gttactgact cgctaccttc gaattcaccc ccagagttgg   4800
gtgcaccaga ttgccctgag gatggaggtt ctgggctgcg aggcacagga cctctactga   4860
ctcgagaata aaagatcaga gctctagaga tctgtgtgtt ggttttttgt gtgcggccgg   4920
gatctgagga ccccctagtg atggagttgg ccactccctc tctgcgcgct cgctcgctca   4980
ctgaggccgc ccgggcaaag cccgggcgtc gggcgacctt tggtcgcccg gcctcagtga   5040
gcgagcgagc gcgcagagag ggagtggcca accccccccc ccccccccct gcaggcgatt   5100
ctcttgtttg ctccagactc tcaggcaatg acctgatagc ctttgtagag acctctcaaa   5160
aatagctacc ctctccggca tgaatttatc agctagaacg gttgaatatc atattgatgg   5220
tgatttgact gtctccggcc tttctcaccc gtttgaatct ttacctacac attactcagg   5280
cattgcattt aaaatatatg agggttctaa aaattttat ccttgcgttg aaataaaggc    5340
ttctcccgca aaagtattac agggtcataa tgttttggt acaaccgatt tagctttatg    5400
ctctgaggct ttattgctta attttgctaa ttctttgcct tgcctgtatg atttattgga   5460
tgttggaatt cctgatgcgg tattttctcc ttacgcatct gtgcggtatt tcacaccgca   5520
tatggtgcac tctcagtaca atctgctctg atgccgcata gttaagccag ccccgacacc   5580
cgccaacacc cgctgacgcg ccctgacggg cttgtctgct cccggcatcc gcttacagac   5640
aagctgtgac cgtctccggg agctgcatgt gtcagaggtt ttcaccgtca tcaccgaaac   5700
gcgcgagacg aaagggcctc gtgatacgcc tatttttata ggttaatgtc atgataataa   5760
tggtttctta gacgtcaggt ggcacttttc ggggaaatgt gcgcggaacc cctatttgtt   5820
tattttctaa atacattca aatatgtatc cgctcatgag acaataaccc tgataaatgc     5880
ttcaataata ttgaaaaagg aagagtatga gtattcaaca tttccgtgtc gcccttattc   5940
cctttttgc ggcattttgc cttcctgttt ttgctcaccc agaaacgctg gtgaaagtaa     6000
aagatgctga agatcagttg ggtgcacgag tgggttacat cgaactggat ctcaacagcg   6060
gtaagatcct tgagagtttt cgccccgaag aacgttttcc aatgatgagc acttttaaag   6120
ttctgctatg tggcgcggta ttatcccgta ttgacgccgg gcaagagcaa ctcggtcgcc   6180
gcatacacta ttctcagaat gacttggttg agtactcacc agtcacagaa aagcatctta   6240
```

```
cggatggcat gacagtaaga gaattatgca gtgctgccat aaccatgagt gataacactg    6300
cggccaactt acttctgaca acgatcggag gaccgaagga gctaaccgct tttttgcaca    6360
acatggggga tcatgtaact cgccttgatc gttgggaacc ggagctgaat gaagccatac    6420
caaacgacga gcgtgacacc acgatgcctg tagcaatggc aacaacgttg cgcaaactat    6480
taactggcga actacttact ctagcttccc ggcaacaatt aatagactgg atggaggcgg    6540
ataaagttgc aggaccactt ctgcgctcgg cccttccggc tggctggttt attgctgata    6600
aatctggagc cggtgagcgt gggtctcgcg gtatcattgc agcactgggg ccagatggta    6660
agccctcccg tatcgtagtt atctacacga cggggagtca ggcaactatg gatgaacgaa    6720
atagacagat cgctgagata ggtgcctcac tgattaagca ttggtaactg tcagaccaag    6780
tttactcata tactttag attgatttaa aacttcattt ttaatttaaa aggatctagg    6840
tgaagatcct ttttgataat ctcatgacca aaatccctta acgtgagttt tcgttccact    6900
gagcgtcaga ccccgtagaa aagatcaaag gatcttcttg agatcctttt tttctgcgcg    6960
taatctgctg cttgcaaaca aaaaaaccac cgctaccagc ggtggtttgt ttgccggatc    7020
aagagctacc aactctttt ccgaaggtaa ctggcttcag cagagcgcag ataccaaata    7080
ctgttcttct agtgtagccg tagttaggcc accacttcaa gaactctgta gcaccgccta    7140
catacctcgc tctgctaatc ctgttaccag tggctgctgc cagtggcgat aagtcgtgtc    7200
ttaccgggtt ggactcaaga cgatagttac cggataaggc gcagcggtcg ggctgaacgg    7260
ggggttcgtg cacacagccc agcttggagc gaacgaccta caccgaactg agatacctac    7320
agcgtgagct atgagaaagc gccacgcttc ccgaagggag aaaggcggac aggtatccgg    7380
taagcggcag ggtcggaaca ggagagcgca cgagggagct tccaggggga aacgcctggt    7440
atctttatag tcctgtcggg tttcgccacc tctgacttga gcgtcgattt ttgtgatgct    7500 cgtcagggg gcggagccta tggaaaaacg ccagcaacgc ggccttttta cggttcctgg    7560
ccttttgctg gccttttgct cacatgttct ttcctgcgtt atccctgat tctgtggata    7620 accgtattac cgcctttgag tgagctgata ccgctcgccg cagccgaacg accgagcgca    7680
gcgagtcagt gagcgaggaa gcggaagagc gcccaatacg caaaccgcct ctccccgcgc    7740
gttggccgat tcattaatgc agctgtggaa tgtgtgtcag ttagggtgtg gaaagtcccc    7800
aggctcccca gcaggcagaa gtatgcaaag catgcatctc aattagtcag caaccaggtg    7860
tggaaagtcc ccaggctccc cagcaggcag aagtatgcaa agcatgcatc tcaattagtc    7920
agcaaccata gtcccgcccc taactccgcc catcccgccc ctaactccgc ccagttccgc    7980
ccattctccg ccccatggct gactaatttt ttttatttat gcagaggccg aggccgcctc    8040
ggcctctgag ctattccaga agtagtgagg aggctttttt ggaggcctag gcttttgcaa    8100
aaagct                                                              8106
```

MODIFIED PLASMA CLOTTING FACTOR VIII AND METHOD OF USE THEREOF

FIELD

The present application relates generally to medical treatment and, in particular, to modified plasma clotting factor VIII polypeptides and their use in the treatment of hemophilia A.

BACKGROUND

Hemophilia A is an X-linked, recessive disorder caused by deficiency of functional plasma clotting factor VIII (hFVIII). In patients with Hemophilia A, the blood does not clot properly resulting in excessive bleeding when injured. The bleeding phenotype is generally related to the residual factor activity: people with severe disease (factor activity <1% normal) have frequent spontaneous bleeds; people with moderate disease (factor activity 1%-5% normal) rarely have spontaneous bleeds, but bleed with minor trauma; and people with mild disease (factor activity 5%-40% normal) bleed during invasive procedures or trauma.

Current treatment for severe hemophilia A (<1% factor VIII activity) requires regular intravenous infusion of recombinant factor VIII (rFVIII) or plasma concentrated factor VIII. Individuals with moderate and mild hemophilia A may be treated on an as needed basis without a regular prophylactic schedule. The infusion treatment is expensive and introduces the risk of infectious diseases. rFVIII therapy has proved to be costly due to the expense of production, purification, and formulation. rFVIII therapy still requires intravenous access for delivery due to limited bioavailability from other delivery routes. The cost and limited availability of rFVIII has prevented universal implementation of this treatment strategy.

Gene therapy provides an alternative to infusion treatment. However, current gene therapies require high viral vector doses, which increase the expenses associated with treatment. Difficulties in implementation of gene therapy techniques, however, include vector toxicity and insufficient expression levels of factor VIII.

Therefore, FVIII bioengineered for improved coagulation activity, as reflected in increased secretion, increased specific activity, or both, will significantly improve rFVIII production in cell culture manufacturing or transgenic animal as well as increase potential for success in gene therapy strategies for hemophilia A. Thus, there is a need for improved vectors and constructs that can efficiently express the hFVIII protein in sufficient quantity to increase FVIII production or reduce the required dose of viral vector to tolerable levels.

SUMMARY

One aspect of the present application relates to a modified hFVIII polypeptide (mhFVIII) that contains one or more mutations as compared to a wild-type hFVIII polypeptide a reference polypeptide.

In some embodiments, the mhFVIII comprises one or more amino acid substitutions at positions A20, T21, F57, L69, I80, L178, R199, H212, I215, R269, I310, L318, S332, R378, I610 and/or I661.

In some embodiments, the mhFVIII comprise one or more amino acid substitutions selected from the group consisting of amino acid substitutions listed in Table 1.

In some embodiments, the mhFVIII comprises one or more amino acid substitutions at positions selected from the group consisting of A20K, T21I, T21V, F57L, L69V, I80V, L178F, R199K, H212Q, I215V, R269K, I310V, L318F, S332P, R378S, I610M and I661V. In some embodiments, the mhFVIII contains a single amino acid substitution.

In some embodiments, the mhFVIII comprises amino acid substitutions in each of amino acids A20K and T21I.

In some embodiments, the mhFVIII comprises the amino acid substitutions A20K and T21V.

In some embodiments, the mhFVIII comprises the amino acid substitutions T21I, L69V, and I80V.

In some embodiments, the mhFVIII comprises the amino acid substitutions T21I, L69V, I80, and L178F.

In some embodiments, the mhFVIII comprises the amino acid substitutions T21I, L69V, I80V, and I661V.

In some embodiments, the mhFVIII comprises the amino acid substitutions T21I, L69V, I80, L178F, and I661V.

In some embodiments, the mhFVIII comprises the amino acid substitutions R199K, H212Q, I215V, R269K, I310V, L318F, and S332P.

In some embodiments, the mhFVIII comprises the amino acid substitutions T21I, L69V, I80V, L178F, H212Q, I215V, R269K, L318F and I661V.

In some embodiments, the mhFVIII comprises the amino acid substitutions A20K, T21V, L69V, I80V, L178F, H212Q, I215V, R269K, L318F and I661V.

In some embodiments, the mhFVIII comprises the amino acid substitutions T21I, L69V, I80V, L178F, R199K, H212Q, I215V, R269K, I310V, L318F, S332P and I661V.

In some embodiments, the mhFVIII comprises the amino acid substitutions A20K, T21V, L69V, I80V, L178F, R199K, H212Q, I215V, R269K, I310V, L318F, S332P and I661V.

In some embodiments, the mhFVIII consists of a single polypeptide comprising the A1, A2, A3, C1 and C2 domains of hFVIII.

In some embodiments, the mhFVIII consists of a single polypeptide comprising: (1) the A1, A2, A3, C1 and C2 domains of hFVIII; and (2) a truncated B domain of hFVIII.

In some embodiments, the mhFVIII consists of a heavy chain polypeptide comprising the A1 and A2 domains of hFVIII, and a light chain polypeptide comprising the A3, C1 and C2 domains of hFVIII. In some embodiments, the heavy chain polypeptide further comprises a truncated B domain of hFVIII and a light chain polypeptide comprising the A3, C1 and C2 domains of hFVIII.

In some embodiments, the mhFVIII comprises a heavy chain of human FVIII and a light chain of FVIII from a different species, such as a light chain of canine FVIII.

Another aspect of the present application relates to an isolated polynucleotide encoding the mhFVIII of the present application.

Another aspect of the present application relates to an expression cassette comprising: the polynucleotide of the present application; and a regulatory sequence operably linked to the polynucleotide.

Another aspect of the present application relates to an expression vector comprising the polynucleotide of the present application. In some embodiments, the expression vector is a plasmid. In some embodiments, the expression vector is a viral vector. In some embodiments, the expression vector is an AAV vector.

Another aspect of the present application relates to a host cell comprising the expression vector of the present application.

Another aspect of the present application relates to a pharmaceutical composition comprising the mFVIII of the present application and a pharmaceutically acceptable carrier.

Another aspect of the present application relates to a pharmaceutical composition comprising the expression vector of present application and a pharmaceutically acceptable carrier.

Another aspect of the present application relates to a method for treating a subject with factor VIII deficiency. The method comprises the step of administering to the subject an effective amount of the mhFVIII, the expression vector, or the host cell of the present application.

Another aspect of the present application relates to a recombinant AAV vector comprising a nucleotide encoding an mhFVIII, wherein the mhFVIII comprises one or more amino acid substitutions at positions selected from the group consisting of A20K, T21I, T21V, F57L, L69V, I80V, L178F, R199K, H212Q, I215V, R269K, I310V, L318F, S332P, R378S, I610M, and I661V, and wherein the AAV vector is capable of expressing the mhFVIII in a host cell. In some embodiments, the mhFVIII comprises a truncated B domain of hFVIII.

Another aspect of the present application relates to a method for expressing an mhFVIII. The method comprises the steps of: (a) introducing into host cells an expression vector comprising: a polynucleotide comprising a nucleotide sequence encoding a signal peptide and a nucleotide sequence encoding the mhFVIII, wherein the mhFVIII comprises one or more amino acid substitutions at positions selected from the group consisting of A20K, T21I, T21V, F57L, L69V, I80V, L178F, R199K, H212Q, I215V, R269K, I310V, L318F, S332P, R378S, I610M and I661V; and a regulatory sequence operatively linked to the polynucleotides; (b) growing the host cells under conditions suitable for expression and secretion of the mhFVIII; (c) harvesting culture medium from the host cells, and (d) purifying the mhFVIII from the harvested culture medium.

BRIEF DESCRIPTION OF THE DRAWINGS

FIG. 1 shows an expression plasmid (pANG-CAG-hBDDF8) encoding a wild-type human FVIII with a deletion in the B domain (hBDDF8). The hBDDF8 coding sequence (including the heavy chain and light chain) is under the control of a CAG promoter that was utilized for assaying functional activities of various modified hBDDF8 proteins (also referred to as "mutant hFVIII" or "hFVIII mutant") in accordance with the present application.

FIG. 2 shows an alignment between the hBDDF8 heavy chain (hBDDF8-HC) and a modified hBDDF8 heavy chain (qwBDDF8-HC) containing 17 substitution mutations in 16 amino acid positions for analysis of hFVIII mutant activity. Additional constructs containing various single, double and multiple substitutions thereof are further described in FIG. 3 and Example 1. Further analyses of the relative functional activities of such mutants are shown in FIGS. 4-9, as further described below.

FIG. 3 summarizes exemplary substitution mutants in the hBDDF8-HC for analysis of hFVIII functional activity.

FIG. 4 shows the relative functional activities of single amino acid substitution hFVIII mutants (i.e., modified hBDDF8 proteins) in HuH7 cells, compared to the functional activity of hFVIII (i.e., un-modified hBDDF8 protein).

FIG. 5 shows the relative functional activities of single amino acid substitution hFVIII mutants (i.e., modified hBDDF8 proteins) in HEK 293T cells, compared to the functional activity of hFVIII (i.e., un-modified hBDDF8 protein).

FIG. 6 shows the relative functional activities of specific single amino acid substitution mutations in amino acid 21 of the hFVIII heavy chain (i.e., hBDDF8 proteins modified at amino acid position 21) in HEK 293T cells, compared to the functional activity of (i.e., un-modified hBDDF8 protein).

FIG. 7 shows the relative functional activities of double amino acid substitutions containing T21I in combination with various substitutions in amino acid 20 of the hFVIII heavy chain (i.e., hBDDF8 proteins modified at amino acid position 21) in HEK 293T cells, compared to each other, as well as an un-modified hBDDF8 protein and the single amino acid substitution mutant T21I.

FIG. 8 shows the functional activities of various hFVIII-HC mutants with single or multiple mutations (as indicated) in Huh7 cells compared to the hBDDF8 cDNA in pANG-CAG-hBDDF8 at 24 hr or 48 hr post transfection.

FIG. 9 shows the functional activities of various hFVIII-HC mutants, including those with single and multiple mutations (as indicated) in HEK 293T cells, compared to the functional activity of hFVIII (i.e., un-modified hBDDF8 protein) at 24 hr, 48 hr and 72 hr post-transfection.

FIG. 10 shows the functional activities of various hFVIII-HC mutants, including those with single or multiple mutations (as indicated) in CHO cells, compared to the functional activity of hFVIII (i.e., un-modified hBDDF8 protein) at 24 hr or 48 hr post-transfection.

FIG. 11A shows the structural domains of selected hFVIII mutants (and wild-type) and human/canine hybrid FVIII mutants, FIG. 11B shows the functional activities in HEK 293 T cells of the B-domainless hFVIII mutants (and wild-type) and human/canine hybrid FVIII mutants in FIG. 11A compared to the functional activity of hFVIII (i.e., un-modified hBDDF8 protein) at 48 hr post-transfection.

FIG. 12 shows an expression plasmid (pANG-TTR-hBDDF8) similar to the expression plasmid in FIG. 1 with the exception that the CAG promoter is replaced by a TTR promoter.

FIG. 13 shows the functional activities of hBDDF8 and various mhFVIII constructs expressed in Huh7 cells from rAAV2 vectors at 72 hr post-transfection.

DETAILED DESCRIPTION

Definition

Various terms relating to the biological molecules of the present application are used herein above and also throughout the specification and claims.

The phrase "activity enhanced FVIII (actFVIII or actF8)" refers to a modified hFVIII (hF8) which has been genetically altered such that the encoded protein exhibits at least 10%, 20%, 30%, 40%, 50%, 60%, 70%, 80%, 90% or 100% increase in activity when compared to unmodified wild-type hFVIII. The nucleotide sequence for unmodified wild-type hFVIII is set forth in SEQ ID NO: 1, which contains the nucleotide sequence encoding a signal peptide of 19 amino acids (MQIELSTCFFLCLLRFCFS (SEQ ID NO:2)). The amino acid sequence for unmodified wild-type hFVIII including the signal peptide is set forth in SEQ ID NO: 3. The amino acid sequence for unmodified wild-type hFVIII without the signal peptide is set forth in SEQ ID NO: 4.

The term "hBDDF8 protein," "hBDDF8 polypeptide" or "hBDDF8" refers to a wild-type hFVIII protein with a deletion in the B domain. In some embodiments, the deletion encompasses most of the B domain, including sequences responsive to multiple cleavages within the wild type B-domain. An exemplary hBDDF8 polypeptide has the amino acid sequence shown in SEQ ID NO:5 (with signal peptide), or SEQ ID NO:6 (without signal peptide) which contains the heavy chain (SEQ ID NO:7), a truncated B-domain (SEQ ID NO:8) and the hFVIII light chain (SEQ ID NO:9).

The phrase "one or more" followed by a list of elements or species is intended to encompass any permutation of elements or species in the list. Thus, for example, the phrase "one or more substitution mutations selected from the group consisting of A, B, C, D, E and F" may include any combination of substitution mutations containing A, B, C, D, E and/or F.

As used herein, ranges may be expressed from one particular integer value to another particular integer value. When such a range is expressed, it should understand that any and all integer values within that range define separate embodiments according to the present application and that the full scope of embodiments includes within the range further includes any and all sub-ranges between any pair of integer values in the initial range.

With reference to nucleic acids of the application, the term "isolated nucleic acid", when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA, molecule inserted into a vector, such as a plasmid or virus vector, or integrated into the DNA of a prokaryote or eukaryote. The nucleic acid codons can be optimized for enhanced expression in the mammalian cells.

With respect to RNA molecules of the application, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to proteins, the term "isolated protein" or "isolated and purified protein" is used herein with reference to a protein produced by expression of an isolated nucleic acid molecule of the application. Alternatively, this term may refer to a protein which has been sufficiently separated from other proteins with which it would naturally be associated, so as to exist in a "substantially pure" form.

The terms "hFVIII polypeptide" refers to the full length human FVIII protein, fragments of human FVIII protein, domains and combination of domains of human FVIII protein that that substantially maintain the biological function of hFVIII.

The term "mutant hFVIII polypeptide" or "modified hFVIII polypeptide" refers to a polypeptide that is different from the reference hFVIII polypeptide by one or more amino acids (e.g., one or more amino acid substitutions). The reference polypeptide can be a wild-type hFVIII protein with or without the signal peptide, a wild-type hFVIII protein with modifications, such as a wild-type hFVIII protein with a deletion in B-domain (e.g., hBDDF8) or a B-domainless hFVIII, a fragment of hFVIII, a domain or a combination of domains of hFVIII with or without further modification. In some embodiments, the "reference hFVIII polypeptide" of a "modified hFVIII polypeptide" refers to the hFVIII polypeptide before modification. In some embodiments, the term "mutant hFVIII polypeptide" or "modified hFVIII polypeptide" refers to a hybrid FVIII polypeptide that comprises a human FVIII heavy chain and a FVIII light chain from a difference species, such as a light chain from canine FVIII.

The term "hFVIII variant" as used herein, refers to a "mutant hFVIII protein" or "modified hFVIII protein" that substantially maintains the biological function of hFVIII.

A "conservative amino acid substitution" is a substitution of an amino acid residue with a functionally similar residue. Examples of conservative substitutions include the substitution of a non-polar (hydrophobic) residue, such as isoleucine, valine, leucine or methionine for another; the substitution of a charged or polar (hydrophilic) residue for another, such as between arginine and lysine, between glutamine and asparagine, or between threonine and serine; the substitution of a basic residue, such as lysine or arginine for another; the substitution of an acidic residue, such as aspartic acid or glutamic acid for another; the substitution of an aromatic residue, such as phenylalanine, tyrosine, or tryptophan for another; or the substitution of alanine or glycine. Mutant FVIII proteins of the present application may include one or more conservatively substituted amino acids relative to a reference protein and maintain some or all of the activity of the reference protein as described herein.

The term "expression cassette", as used herein, refers to a nucleic acid construct comprising nucleic acid elements sufficient for the expression of the polynucleotide of interest. Typically, an expression cassette comprises the polynucleotide of interest operatively linked to a regulatory sequence, such as a promoter and an enhancer. In some embodiments, an expression cassette may comprise additional elements, for example, an intron, a polyadenylation site, a woodchuck hepatitis virus post-transcriptional response element (WPRE), a secretory signal sequence and/or other elements known to affect expression levels of the encoding sequence.

The term "regulatory sequence" refers to the transcriptional regulatory sequences of a gene, which may be found at the 5' or 3' side of the coding region, or within the coding region, or within introns. Examples of regulatory sequences include, but are not limited to, promoters and enhancers.

The term "promoter", as used herein, refers to a nucleotide sequence capable of controlling the expression of a coding sequence or functional RNA. In general, the polynucleotide of interest is located 3' of a promoter sequence. In some embodiments, the promoter is derived in its entirety from a native gene. In some embodiments, the promoter is composed of different elements derived from different naturally occurring promoters. In some embodiments, the promoter comprises a synthetic nucleotide sequence. It will be understood by those skilled in the art that different promoters will direct the expression of a gene in different tissues or cell types, or at different stages of development, or in response to different environmental conditions or to the presence or the absence of a drug or transcriptional co-factor. Ubiquitous, cell-type-specific, tissue-specific, developmental stage-specific, and conditional promoters, for example, drug-responsive promoters (e.g., tetracycline-responsive promoters) are well known to those of skill in the art. Examples of promoter include, but are not limited to, the phophoglycerate kinase (PKG) promoter, CAG, NSE (neuronal specific enolase), synapsin or NeuN promoters, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), SFFV promoter, roes sarcoma virus (RSV) promoter, synthetic promoters, hybrid promoters, and the like. The promoters can be of human origin or from other species, including from mice. In addition, sequences derived from nonviral genes, such as the murine metallothionein gene promoter, will also find use herein. In some embodiments, the promoter is a heterologous promoter. In some embodiments, a promoter sequence consists of proximal and more distal upstream elements and can comprise an enhancer element.

The term "heterologous promoter", as used herein, refers to a promoter that does is not found to be operatively linked to a given encoding sequence in nature.

The term "enhancer" refers to a nucleotide sequence that can stimulate promoter activity and may be an innate element of the promoter or a heterologous element inserted to enhance the level or tissue-specificity of a promoter.

The term "operatively linked" or "operably linked" refers to the association of two or more nucleic acid fragments on a single nucleic acid fragment so that the function of one is affected by the other. For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation.

As used herein, the term "secretory signal sequence," "signal peptide" or variations thereof are intended to refer to amino acid sequences that function to enhance (as defined above) secretion of an operably linked polypeptide from the cell as compared with the level of secretion seen with the native polypeptide. As defined above, by "enhanced" secretion, it is meant that the relative proportion of the polypeptide synthesized by the cell that is secreted from the cell is increased; it is not necessary that the absolute amount of secreted protein is also increased. In some embodiments, essentially all (i.e., at least 95%, 97%, 98%, 99% or more) of the polypeptide is secreted. It is not necessary, however, that essentially all or even most of the polypeptide is secreted, as long as the level of secretion is enhanced as compared with the native polypeptide. Generally, secretory signal sequences are cleaved within the endoplasmic reticulum and, in some embodiments, the secretory signal sequence is cleaved prior to secretion. It is not necessary, however, that the secretory signal sequence is cleaved as long as secretion of the polypeptide from the cell is enhanced and the polypeptide is functional. Thus, in some embodiments, the secretory signal sequence is partially or entirely retained. The secretory signal sequence can be derived in whole or in part from the secretory signal of a secreted polypeptide (i.e., from the precursor) and/or can be in whole or in part synthetic. The length of the secretory signal sequence is not critical; generally, known secretory signal sequences are from about 10-15 to 50-60 amino acids in length. Further, known secretory signals from secreted polypeptides can be altered or modified (e.g., by substitution, deletion, truncation or insertion of amino acids) as long as the resulting secretory signal sequence functions to enhance secretion of an operably polypeptide. The secretory signal sequences of the invention can comprise, consist essentially of or consist of a naturally occurring secretory signal sequence or a modification thereof (as described above). Numerous secreted proteins and sequences that direct secretion from the cell are known in the art. The secretory signal sequence of the invention can further be in whole or in part synthetic or artificial. Synthetic or artificial secretory signal peptides are known in the art, see e.g., Barash et al., "Human secretory signal peptide description by hidden Markov model and generation of a strong artificial signal peptide for secreted protein expression," Biochem. Biophys. Res. Comm 294:835-42 (2002); the disclosure of which is incorporated herein in its entirety. The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g., promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g., chromatographic methods, agarose or polyacrylamide gel electrophoresis, HPLC analysis, and the like).

The phrase "consisting essentially of when referring to a particular nucleotide sequence or amino acid sequence means a sequence having the properties of a given SEQ ID NO. For example, when used in reference to an amino acid sequence, the phrase includes the sequence per se and molecular modifications that would not affect the basic and novel characteristics of the sequence.

The term "oligonucleotide," as used herein refers to primers and probes of the present application, and is defined as a nucleic acid molecule comprised of two or more ribo- or deoxyribonucleotides, preferably more than three. The exact size of the oligonucleotide will depend on various factors and on the particular application for which the oligonucleotide is used. The term "probe" as used herein refers to an oligonucleotide, polynucleotide or nucleic acid, either RA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The term "percent identical" is used herein with reference to comparisons among nucleic acid or amino acid sequences. Nucleic acid and amino acid sequences are often compared using computer programs in e.g. the National Library of Medicine BLAST alignment program.

A "corresponding" nucleic acid or amino acid or sequence of either, as used herein, is one present at a site in a FVIII or mutant FVIII molecule or fragment thereof that has the same structure and/or function as a site in the FVIII molecule of another species, although the nucleic acid or amino acid number may not be identical. A sequence "corresponding to" another FVIII sequence substantially corresponds to such a sequence, and hybridizes to the human FVIII DNA sequence designated SEQ ID NO:1 under stringent conditions. A sequence "corresponding to" another FVIII sequence also includes a sequence that results in the expression of a FVIII or claimed procoagulant hybrid FVIII or fragment thereof and would hybridize to a nucleic molecule comprising SEQ ID NO:1 but for the redundancy of the genetic code.

A "unique" amino acid residue or sequence, as used herein, refers to an amino acid sequence or residue in the FVIII molecule of one species that is different from the homologous residue or sequence in the FVIII molecule of another species.

"Specific activity," as used herein, refers to the activity that will correct the coagulation defect of human factor VIII-deficient plasma. Specific activity is measured in units of clotting activity per milligram total FVIII protein in a standard assay in which the clotting time of human FVIII deficient plasma is compared to that of normal human plasma. One unit of FVIII activity is the activity present in one milliliter of normal human plasma. In the assay, the shorter the time for clot formation, the greater the activity of the being assayed. Hybrid human/porcine FVIII has coagulation activity in a human FVIII assay. This activity, as well as that of other hybrid or hybrid equivalent molecules or fragments thereof, may be less than, equal to, or greater than that of either plasma-derived or recombinant human FVIII.

"Subunits" of human or animal FVIII, as used herein, are the heavy and light chains of the protein. The heavy chain of contains three domains, A1, A2, and B. The light chain of FVIII also contains three domains, A3, CI, and C2.

The terms "epitope", "antigenic site", and "antigenic determinant", as used herein, are used synonymously and are defined as a portion of the human, animal, hybrid, or hybrid equivalent FVIII or fragment thereof that is specifically recognized by an antibody. It can consist of any number of amino acid residues, and it can be dependent upon the primary, secondary, or tertiary structure of the protein. In accordance with this disclosure, a hybrid hybrid FVIII equivalent, or fragment of either that includes at least one epitope may be used as a reagent in the diagnostic assays described below. In some embodiments, the hybrid or hybrid equivalent FVIII or fragment thereof is not cross-reactive or is less cross-reactive with all naturally occurring inhibitory FVIII antibodies than human or porcine FVIII.

The term "immunogenic site", as used herein, is defined as a region of the human or animal FVIII, hybrid or hybrid equivalent FVIII, or fragment thereof that specifically elicits the production of antibody to the hybrid, hybrid equivalent, or fragment in a human or animal, as measured by routine protocols, such as immunoassay, e.g., ELISA, or the Bethesda assay, described herein. It can consist of any number of amino acid residues, and it can be dependent upon the primary, secondary, or tertiary structure of the protein. In some embodiments, the hybrid or hybrid equivalent FVIII or fragment thereof is non-immunogenic or less immunogenic in an animal or human than human or porcine FVIII.

"FVIII deficiency," as used herein, refers to a deficiency in clotting activity caused by: (1) production of a defective FVIII; (2) inadequate or no production of FVIII; or (3) partial or total inhibition of FVIII. Hemophilia A is a type of FVIII deficiency resulting from a defect in an X-linked gene and the absence or deficiency of the FVIII protein it encodes.

II. Modified Polypeptides (mhFVIII)

One aspect of the present application relates to modified hFVIII polypeptides (mhFVIII) that contain one or more mutations as compared to a wild-type hFVIII polypeptide or an un-modified reference polypeptide. In some embodiments, the mhFVIIIs, when expressed in a host cell, result in increased hFVIII activity in the host cell, as compared to a wild-type hFVIII or a reference protein (such as hBDDF8) expressed in a host cell of the same type under the same conditions.

Human FVIII encodes a 2351 amino acids protein (with 19 amino acid of signal peptides and 2332 amino acids of mature protein). It is arranged with a series of structural "domains": $NH_2$-SP-A1-a1-A2-a2-B-a3-A3-C1-C2-COOH. As used herein, a FVIII "domain" is defined by a continuous sequence of amino acids characterized by e.g., internal amino acid sequence identity to structurally related domains and by sites of proteolytic cleavage by thrombin. Further, the terms "domainless" or "lacking a domain" should be understood to mean that at least 95% or 100% of the domain has been deleted. Unless otherwise specified, FVIII domains are defined by the following amino acid residues arranged in hFVIII (as set forth in SEQ ID NO:3) from amino terminal to carboxy terminal end as follows: SP, amino acid residues 1.19; A1 domain, amino acid residues 20-354; a1 domain, amino acid residues 355-391, A2 domain, amino acid residues 392-728: a2 domain, amino acid residues 729-760, B domain, amino acid residues 761-667; a3 domain, amino acid residues 1668-1708; A3 domain, amino acid residues 1709-2039; C1 domain, amino acid residues 2040-2192; and C2 domain, amino acid residues 2193-2351.

The A1-$a_1$-A2-$a_2$-B (aa 20-1667) sequence or A1-$a_1$-A2-$a_2$ (aa 1-740) sequence is usually referred to as the hFVIII heavy chain. The $a_3$-A3-C1-C2 sequence (aa1668-2351) is usually referred to as the hFVIII light chain. FVIII is proteolytically activated by thrombin or factor Xa, which dissociates it from von Willebrand factor, forming FVIIIa, which has procoagulant function, The biological function of FVIIIa is to increase the catalytic efficiency of factor IXa toward factor X activation by several orders of magnitude. Thrombin-activated FVIIIa is a 160 kDa A1-$a_1$/A2-$a_2$/$a_3$-A3-C1-C2 heterotrimer that forms a complex with factor IXa and factor X on the surface of platelets or monocytes.

A cDNA sequence encoding the wild-type human FVIII has the nucleotide sequence set forth in SEQ ID NO:1. In SEQ ID NO:1, the first 57 nucleotides of the FVIII open reading frame encodes a signal peptide sequence (SEQ ID NO:2) which is typically cleaved off from the mature FVIII protein.

In some embodiments, the modified hFVIII polypeptides of the present application comprises one or more amino acid substitutions in the region corresponding to amino acid residues 20171 of the wild-type hFVIII amino acid sequence set forth in SEQ ID NO:3. In some embodiments, the modified hFVIII polypeptides of the present application comprises one or more substitutions at position A20, T21, F57, L69, I80, L178, R199, H212, I215, R269, I310, L318, S332, R378, I610, and I661.

With reference to mutants or modifications described herein, the position nomenclature represented by a one letter code of an amino acid followed with a numerical number refers to the amino acid residue and its position in the wild-type hFVIII (SEQ ID NO:3). For example, the nomenclature "A20" refers to the amino acid residue alanine (A) at position 20 of the wild-type hFVIII sequence (SEQ ID NO3). Similarly, the substitution nomenclature represented by a first one letter code of an amino acid, followed with a numerical number, followed with a second one letter code of an amino acid refers to the substitution of the original amino acid residue at the position indicated by the numerical number in the wild-type hFVIII (SEQ ID NO:3) with the second amino acid. For example, the nomenclature "A20K" refers to the substitution of amino acid residue alanine (A)

at position 20 of the wild-type hFVIII (SEQ ID NO:3) with the amino acid residue lysine (K). The amino acid position nomenclature and substitution nomenclature also apply to domains of hFVIII, heavy and light chain of hFVIII, fragments of hFVIII, polypeptides that share a common sequence with hFVIII, and/or other hFVIII derived sequences, such as hBDDF8.

In some embodiments, the present application provides mhFVIIIs comprising amino acid substitution(s) in one or more amino acid residues selected from the group consisting of A20, T21, F57, L69, I80, L178, R199, H212, I215, R269, I310, L318, S332, R378, I610 and I661. The mhFVIIIs may include any permutation of mutations encompassing these 16 amino acid sites. Exemplary mhFVIIIs for use in accordance with the present application are described in FIG. 3, which identifies single and multiple mutations as filled in boxes.

In some embodiments, the mhFVIIIs of the present application include one or more amino acid substitutions selected from the group consisting of A20K, T21I, T21V, F57L, L69V, I80V, L178F, R199K, H212Q, I215V, R269K, I310V, L318F, S332P, R378S, I610M and I661V.

In some embodiments, the mhFVIII of this application comprise an amino acid substitution at position T21. Preferred substitutions include T21I and T21V. In some embodiments, the mhFVIII further comprises one or more amino acid substitutions at positions selected from the group consisting of A20, F57, L69, I80, L178, R199, H212, I215, R269, I310, L318, S332, R378, I610 and I661.

In some embodiments, the mhVIIIs of the present application comprise amino acid substitutions at positions A20 and T21. In some embodiments, the mhFVIIIs of the present application comprise the amino acid substitutions A20K and T21I (the 2M1 mutant), or amino acid substitutions A20K and T21V (the 2M2 mutant).

In some embodiments, the mhFVIIIs of the present application comprise amino acid substitutions at positions T21, L69 and I80. In some embodiments, the mhFVIIIs of the present application comprise the amino acid substitutions T21I, L69V, and I80V (the 3M1 mutant).

In some embodiments, the mhFVIIIs of the present application comprise amino acid substitutions at positions T21, L69, I80, and L178. in some embodiments, the mhFVIIIs of the present application comprise the amino acid substitutions T21I, L69V, I80, and L178F (the 4M1 mutant).

In some embodiments, the mhFVIIIs of the present application comprise amino acid substitutions at positions T21, L69, I80 and I661. In some embodiments, the mhFVIIIs of the present application comprise the amino acid substitutions T21I, L69V, I80V and I661V (the 4M3 mutant).

In some embodiments, the mhFVIIIs of the present application comprise amino acid substitutions at positions T21, L69, I80, L178 and I661. In some embodiments, the mhFVIIIs of the present application comprise the amino acid substitutions T21I, L69V, I80V, L178F and I661V (the 5M4 mutant).

In some embodiments, the mhFVIIIs of the present application comprise amino acid substitutions at positions R199, H212, I215, R269, I310, L318 and S332. In some embodiments, the mhFVIIIs of the present application comprise the amino acid substitutions R199K, H212Q, I215V, R269K, I310V, L318F and S332P (the 7M2 mutant).

In some embodiments, the mhFVIIIs of the present application comprise amino acid substitutions at positions T21, L69, I80, L178, H212, I215, R269, L318 and I661. In some embodiments, the mhFVIIIs of the present application comprise the amino acid substitutions T21I, L69V, I80V, L178F, H212Q, I215V, R269K, L318F and I661V (the 9M1 mutant).

In some embodiments, the mhFVIIIs of the present application comprise amino acid substitutions at positions A20, T21, L69, I80, L178, H212, I215, R269, L318 and I661. In some embodiments, the mhFVIIIs of the present application comprise the amino acid substitutions A20K, T21V, L69V, I80V, L178F, H212Q, I215V, R269K, L318F and I661V (the 10M1 mutant).

In some embodiments, the mhFVIIIs of the present application comprise amino acid substitutions at positions T21, L69, I80, L178, R199, H212, I215, R269, I310, L318, S322 and I661. In some embodiments, the mhFVIIIs of the present application comprise the amino acid substitutions T21I, L69V, I80V, L178F, R199K, H212Q, I215V, R269K, I310V, L318F, S322P and I661V (the 12M1 mutant).

In some embodiments, the mhFVIIIs of the present application comprise amino acid substitutions at positions A20, T21, L69, I80, L178, R199, H212, I215, R269, I310, L318, S332 and I661. In some embodiments, the mhFVIIIs of the present application comprise the amino acid substitutions A20K, T21V, L69V, I80V, L178F, R199K, H212Q, I215V, R269K, I310V, L318F, S332P and I661V (the 13M1 mutant).

In some embodiments, the amino acid positions corresponding to the above-described amino acid substitutions may be substituted with other conservative substitutions. Table 1 provides a list of exemplary amino acid substitutions at the amino acid positions A20, T21, L69, I80, L178, R199, H212, I215, R269, I310, L318, S332 and I661.

TABLE 1

Exemplary amino substitutions.

| Position | Exemplary Substitutions | | | | | | |
|---|---|---|---|---|---|---|---|
| A20 | K | L | V | E | S | I | T |
| T21 | V | I | | | | | |
| F57 | L | Y | S | P | | | |
| L69 | V | I | | | | | |
| I80 | V | T | L | M | Q | E | R |
| L178 | F | M | S | | | | |
| R199 | K | | | | | | |
| H212 | Q | P | Y | N | R | | |
| I215 | V | | | | | | |
| R269 | K | Q | N | G | | | |
| I310 | V | A | M | | | | |
| L318 | F | S | V | H | L | T | M |
| S332 | P | L | | | | | |
| R378 | S | N | K | T | I | | |
| I610 | M | | | | | | |
| I661 | V | | | | | | |

In some embodiments, the above-described mhFVIIIs comprises a deletion in the B-domain ("B domainless"). Examples of hFVIII polypeptide comprising a deletion in the B-domain are described in U.S. Pat. Nos. 6,800,461, 6,780,614 U.S. U.S. and Patent Application Publication No. 2004/0197875, which are hereby incorporated by reference.

In some embodiments, the mhFVIIIs of the present application comprise a single chain polypeptide. In some embodiments, the mhFVIIIs of the present application comprise a single chain hFVIII polypeptide with a truncated or deleted B-domain. In some embodiments, the mhFVIIIs of the present application comprise a heterodimer of a heavy chain (HC) comprising the A1 domain and the A2 domain, and a light chain (LC) comprising the A3 domain, the C1 domain and the C2 domain. In some embodiments, the mhFVIIIs of the present application comprise a heterodimer of a heavy chain (HC) comprising the A1 domain, the A2 domain, and a full length or truncated B-domain, and a light chain (LC) comprising the A3 domain, the C1 domain and the C2 domain. In some embodiments, the mhFVIIIs of the present application comprise a heterotrimer of a polypeptide comprising the A1 domain, a polypeptide comprising the A2 domain, and a polypeptide comprising the A3 domain, the C1 domain and the C2 domain.

In some embodiments, the above-described mhFVIIIs are derived from a wild type hBDDF8 containing a deletion in the B domain with a native hFVIII signal peptide as set forth in SEQ ID NO:5. The secreted forms of the mhFVIIIs do not contain the signal peptide sequence shown in SEQ ID NO:2.

In some embodiments, the mhFVIIIs of the present application, when expressed in vitro or in vivo, result in increased FVIII activity of between 5% to 100 fold, 10% to 50 fold, 50% to 25 fold, 2 to 100 fold, 2 to 80 fold, 2 to 60 fold, 2 to 40 fold, 2 to 20 fold, 2 to 10 fold, 2 to 5 fold, at least 2 fold, at least 3 fold, at least 4 fold, at least 5 fold, at least 10 fold, at least 20 fold, at least 30 fold, at least 40 fold, at least 50 fold, at least 70 fold, at least 80 fold or at least 100 fold of the wild-type hFVIII or the reference polypeptide from which the derived. In vitro FVIII activity may be determined by analyzing the tissue culture media from cells expressing the mhFVIIIs. In vivo FVIII activities may be determined by analyzing the plasma collected from individuals receiving infusions of mhFVIIIs or expression vectors expressing the mhFVIIIs.

In some embodiments, the mhFVIIIs of the present application as described above may be further modified to additionally include, delete, or modify other FVIII sequences in order to confer other desirable properties, such as reduced antigenicity, increased stability, increased circulating half-life via binding to serum-binding proteins, increased protein secretion, increased affinity for factor IXa and/or factor X, decreased affinity for von Willebrand factor, increased glycosylation, altered inactivation cleavage, alteration of at least one calcium binding site, and/or increased shelf-life.

For example, in some embodiments, the mhFVIIIs of the present application may be modified to additionally include amino acid substitutions responsible for immunogenicity and/or antigenicity of human FVIII, as described in U.S. Pat. Nos. 5,859,204, 6,770,744, and U.S. Patent Application Publication No. 2003/0166536, such as R503A, R503G, P504A, L505S, Y506L, Y506A, S507A, S507L, R508A, R508S, R509G, L510S, P511L, P511A, K512A, G513S, V514A, K515M, H516L, L517S, K518M, D519A, F520A, P521L, I522M, L523M, P524A, G525A, E526G, I527M, I528A, M2218I, F2219L, V2242A, K2246E, L2271F or any combination thereof.

In other embodiments, the mhFVIIIs of the present application as described above may be modified to additionally include amino acid substitutions providing increased secretion as described in U.S. Patent Application No. 2016/102133, such as I105V, Y124F, A127S, D134E, Q136H, F148L, G151K, H153Q, M166T and L171P or any combination thereof.

In other embodiments, the mhFVIIIs of the present application as described above may be modified to additionally include amino acid substitutions to confer greater stability of activated FVIII by virtue of fused A2 and A3 domains. In particular, a FVIII can be modified by substituting cysteine residues at positions 683 and 1845, (i.e., Y683C, T1845C) resulting in a mutant FVIII forming a C683-C1845 disulfide bond covalently linking the A2 and A3 domains.

In other embodiments, the mhFVIIIs of the present application as described above may be further modified to additionally include amino acid substitutions conferring altered inactivation cleavage sites. For example, A355 or A581 may be substituted used to decrease the mutant FVIII's susceptibility to cleavage enzymes that normally inactivate the wild type FVIII In other embodiments, the mhFVIIIs of the present application as described above may be further modified to additionally include amino acid substitutions conferring enhanced affinity for factor IXa.

In other embodiments, the mhFVIIIs of the present application as described above may be further modified to additionally include amino acid substitutions conferring increased circulating half-life. This may be achieved through various approaches, including, without limitation, by reducing interactions with heparan sulfate In other embodiments, the mhFVIIIs of the present application as described above may be further modified to additionally include amino acid substitutions conferring recognition sequences for glycosylation at asparagine residues. Such modifications can be useful escaping detection by existing inhibitory antibodies (low antigenicity FVIII) and by decreasing the likelihood of developing inhibitory antibodies (low immunogenicity FVIII). In one representative embodiment, the modified FVIII is mutated to incorporate a consensus amino acid sequence for N-linked glycosylation, such as N—X—S/T.

In other embodiments, the mhFVIIIs of the present application as described above may be further modified to additionally include mutations to (i) delete the von Willebrand factor binding site, (ii) add a mutation at A759, and/or (iii) add an amino acid sequence spacer between the A2- and A3-domains, where the amino acid spacer is of a sufficient length so that upon activation, the procoagulant-active FVIII protein becomes a heterodimer in some embodiments, the mhFVIIIs of the present application are hybrid FVIII comprising a human FVIII heavy chain and a FVIII light chain from a different species, such as a light chain from canine FVIII. In some embodiments, the human FVIII heavy chain further comprises one or more amino acid substitutions described in the present application. In some embodiments, the hybrid FVIII comprises a truncated B-domain. In some embodiments, the hybrid FVIII consists of a single polypeptide comprising (1) a wild-type human FVIII heavy chain sequence or a modified human FVIII heavy chain sequence, and (B) a FVIII light chain sequence from a different species, such as a light chain from canine FVIII. In some embodiments, the modified human FVIII heavy chain sequence comprises one or more of the amino acid substitutions described in this application. In some embodiments, the modified human FVIII heavy chain sequence comprises the hBDDF8 sequence or a modified hBDDF8 sequence with one or more of the amino acid substitutions described in this application.

III. mhFVIII-Encoding Polynucleotides, Expression Cassettes and Expression Vectors Another aspect of the present application relates to isolated polynucleotide encoding the mhFVIIIs of the present application, including all possible nucleic acids encoding the breadth of substitutions and/or other mutations described herein. The isolated nucleic acid can be an RNA or DNA.

In certain embodiments, the polynucleotide encodes a mhFVIII polypeptide which is codon optimized for expression in various human, primate or mammalian cells, such as HuH7, HEK293T or CHO cells. Polynucleotides encoding the mhFVIII of the present application may be codon optimized to improve the activity, stability or expression in host cells without changing the encoded amino acid sequence.

A codon consists of a set of three nucleotides and encodes a specific amino acid or results in the termination of translation (i.e. stop codons). The genetic code is redundant in that multiple codons specify the same amino acid, i.e., there are a total of 61 codons encoding 20 amino acids. Codon optimization replaces codons present in a polynucleotide sequence with preferred codons encoding the same amino acid, for example, codons preferred for mammalian expression. Thus, the amino acid sequence is not altered during the process. Codon optimization can be performed using gene optimization software. The codon optimized nucleotide sequence is translated and aligned to the original protein sequence to ensure that no changes were made to the amino acid sequence. Methods of codon optimization are known in the art and are described, for example, in U.S. Application Publication No. 2008/0194511 and U.S. Pat. No. 6,114,148.

In some embodiments, the mhFVIII protein is expressed in the form of a single chain B-domainless mhFVIII. In some embodiments, the mhFVIII protein is expressed from one or more nucleic acids in the form of a dual-chain (DC) protein comprising a heavy chain (HC) and a light chain (LC) of hFVIII. In some embodiments, the mhFVIII protein is expressed from one or more nucleic acids in the form of heterotrimer of a polypeptide comprising the A1 domain, a polypeptide comprising the A2 domain, and a polypeptide comprising the A3, C1 and C2 domains.

In some embodiments, the mhFVIII-coding polynucleotides of the present application include a coding sequence for expressing a wild type hFVIII amino terminal signal peptide (SEQ ID NO:2), which is removed from the mature protein, in some embodiments, the mhFVIIIs of the present application are derived from the hBDDF8 protein having an amino acid sequence of SEQ ID NO:5 (with signal peptide) or SEQ ID NO:6 (without signal peptide). Since signal peptide sequences can affect the levels of expression, the mhFVIII-encoded polynucleotides may be engineered for expressing mhFVIIIs carrying any of a variety of heterologous N-terminal signal peptides known in the art.

In some embodiments, the mhFVIII-coding polynucleotide of the present application as described above may he modified to additionally include, delete, or modify other FVIII sequences conferring other desirable properties, such reduced antigenicity, increased stability, increased circulating half-life via binding to serum-binding proteins, increased protein secretion, increased affinity for factor IXa and/or factor X, decreased affinity for von Willebrand factor, increased glycosylation, altered inactivation cleavage, alteration of one or more calcium binding site(s), and/or increased shelf-life as further described above.

A further aspect of the present application relates to an expression cassette for expressing the mhFVIIIs described herein. In some embodiments, the expression cassette comprises a nucleotide sequence encoding a mhFVIII of the present application and a regulatory sequence operably linked to the nucleotide sequence. In some embodiments, the regulatory sequence comprises a promoter.

A further aspect of the present application relates to an expression vector capable of expressing the mhFVIIIs of the present application in vitro and/or in vivo. In some embodiments, the expression vector is a non-viral vector, such as a plasmid. In some embodiments, the expression vector is a viral vector, such as an AAV vector or lentiviral vector.

Expression vectors for expressing the mhFVIIIs of the present application typically include one or more regulatory sequences operably linked to the polynucleotide sequence to be expressed. It will be appreciated by those skilled in the art that the design of the expression vector can depend on such factors as the choice of the host cell to be transformed, the level of expression of protein desired, and the like. The expression vectors of the application can be introduced into host cells to thereby produce the mhFVIIIs described herein.

Suitable expression vectors for directing expression in mammalian cells generally include a promoter, as well as other transcription and translation control sequences known in the art. In certain embodiments, the mammalian expression vector is capable of directing expression of the polynucleotide preferentially in a particular cell type (e.g., tissue-specific regulatory elements are used to express the polynucleotide). Tissue-specific regulatory elements are known in the art and may include, for example, liver cell-specific promoters and/or enhancers (e.g., albumin promoter, a-1 antitrypsin promoter, apoE enhancer). Alternatively, a constitutive promoter (e.g., HCMV) active in virtually any cell type may be used.

In certain preferred embodiments, the expression vectors are viral vectors. Viral vectors typically have one or more viral genes removed and include a gene/promotor cassette inserted into a viral genome insertion site for insertion of exogenous transgenes, including the mutant FVIII genes described herein. The necessary functions of the removed gene(s) may be supplied by cell lines which have been engineered to express the gene products of the early genes in trans. Exemplary viral vectors include, but are not limited to, adeno-associated viral (AAV) vectors, retroviral vectors, including lentiviral vectors, adenoviral vectors, herpes viral vectors, and alphavirus vectors. Other viral vectors include astrovirus, coronavirus, orthomyxovirus, papovavirus, paramyxovirus, parvovirus, picornavirus, poxvirus, togavirus viral vectors and the like. The viral vector may comprise any suitable nucleic acid construct, such as a DNA or RNA construct and may be single stranded, double stranded, or duplexed.

Once a DNA construct of the present application has been prepared, it is ready to be incorporated into a host cell. Accordingly, another aspect of the present application relates to a method of making a recombinant cell comprising a mhFVIII nucleic acid. Basically, this entails introducing the DNA construct into cells via transformation, transduction, electroporation, calcium phosphate precipitation, liposomes and the like and selecting for cells that have incorporated the DNA episomally or integrated into the host genome. In some embodiments, the mhFVIII expressing cells are transplanted into a subject for the treatment of hemophilia.

In some embodiments, the mhFVIII protein is expressed from a viral vector for administration to a patient with hemophilia. In some embodiments, the viral vector is an AAV vector. In some embodiments, the viral vector is a lentiviral vector. In some embodiments, the viral vector is an adenoviral vector. In some embodiments, the viral vector is a retroviral vector. In some embodiments, the viral vector is herpes virus vector. In some embodiments, methods are provided for the administration of one or more AAV vectors encoding a mhFVIII.

Recombinant AAV and lentiviral vectors have found broad utility for a variety of gene therapy applications. Their utility for such applications is due largely to the high efficiency of in vivo gene transfer achieved in a variety of organ contexts. AAV and lentiviral particles may be used to advantage as vehicles for effective gene delivery. Such virions possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vitro and in vivo by receptor-mediated endocytosis or by transcytosis. These vector systems have been tested in humans targeting retinal epithelium, liver, skeletal muscle, airways, brain, joints and hematopoietic stem cells. It is likely that non-viral vectors based on plasmid DNA or minicircles will be also suitable gene transfer vectors for a large gene as that encoding FVIII.

In some embodiments, the mhFVIII coding sequence is provided as a component of a viral vector packaged in a capsid. In some embodiments, an AAV vector is used for in vivo delivery of the mhFVIIIs of the present application. In this case, the AAV vector includes at least one mhFVIII and associated expression control sequences for controlling expression of the mhFVIII sequence. Exemplary AAV vectors for expressing mhFVIII sequences may include promoter-enhancer regulatory regions for FVIII expression and cis-acting ITRs functioning to enable promote replication and packaging of the mhFVIII nucleic acids into AAV capsids and integration of the mhFVIII nucleic acid into the genome of a target cell. Preferably, the AAV vector has its rep and cap genes deleted and replaced by the mhFVIII sequence and its associated expression control sequences. The mhFVIII sequence is typically inserted adjacent to one or two (i.e., flanked by) AAV TRs or TR elements adequate for viral replication. Most preferably, only the essential parts of the vector e.g., the ITR and LTR elements, respectively are included. In some embodiments, two or more AAV vectors are used for in vivo delivery of a mhFVIII of the present application. In this case, each AAV vector is constructed as described above and carry a portion of the mhFVIII coding sequence (e.g., one vector carries the coding sequence for the mhFVIII heavy chain and another vector carries the coding sequence for the mhFVIII light chain).

Regulatory sequences suitable for facilitating tissue-specific expression of the mutant hFVIII sequence in the target cell are utilized for in expression of the mhFVIIIs in vitro or in vivo. The incorporation of tissue specific regulatory elements in the expression constructs of the present application provides for at least partial tissue tropism for the expression of the mhFVIIIs or functional fragments thereof. For example, nucleic acid sequences encoding a mutant FVIII under the control of a cytomegalovirus (CMV) promoter or a CAG promoter can be employed for skeletal muscle expression or the hAAT-ApoE and others for liver specific expression. Hematopoietic specific promoters in AAV and lentiviral vectors may also be utilized to drive expression of the mhFVIIIs in vivo.

The viral capsid component of the packaged viral vectors may be a parvovirus capsid. AAV Cap and chimeric capsids are preferred. Examples of suitable parvovirus viral capsid components are capsid components from the parvoviridae family, such as an autonomous parvovirus or a dependovirus. For example, the viral capsid may be an AAV capsid (e.g., AAV1, AAV2, AAV3, AAV4, AAV5, AAV6, AAV7, AAV8, AAV9, AAV10, AAV11 or AAV12 capsid; one skilled in the art would know there are likely other variants not yet identified that perform the same or similar function), or may include components from two or more AAV capsids. A fun complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

One or more of the AAV Cap proteins may be a chimeric protein, including amino acid sequences AAV Caps from two or more viruses, preferably two or more AAVs, as described in Rabinowitz et al., U.S. Pat. No. 6,491,907. For example, the chimeric virus capsid can include an AAV1 Cap protein or subunit and at least one AAV2 Cap or subunit. The chimeric capsid can, for example, include an AAV capsid with one or more B19 Cap subunits, e.g., an AAV Cap protein or subunit can be replaced by a B19 Cap protein or subunit. For example, the Vp3 subunit of the AAV capsid can be replaced by the Vp2 subunit of B19.

Packaging cells may be cultured to produce packaged viral vectors of the application, The packaging cells may include (1) viral vector function(s), (2) packaging function(s), and (3) helper function(s). The viral vector functions typically include a portion of a parvovirus genome, such as an AAV genome, with rep and cap deleted and replaced by the mutant FVIII sequence and its associated expression control sequences as described above.

In certain embodiments, the viral vector functions may suitably be provided as duplexed vector templates, as described in U.S. Patent Publication No. 2004/0029106 to Samulski et al. Duplexed vectors are dimeric self-complementary (sc) polynucleotides (typically, DNA). For example, the DNA of the duplexed vectors can be selected so as to form a double-stranded hairpin structure due to intrastrand base pairing. Both strands of the duplexed DNA vectors may be packaged within a viral capsid. The duplexed vector provides a function comparable to double-stranded DNA virus vectors and can alleviate the need of the target cell to synthesize complementary DNA to the single-stranded. genome normally encapsidated by the virus.

The TR(s) (resolvable and non-resolvable) selected for use in the viral vectors are preferably AAV sequences (from any AAV serotype). Resolvable AAV ITRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al. Typically, but not necessarily, the TRs are from the same parvovirus, e.g., both TR sequences are from AAV2.

The packaging functions include capsid components. The capsid components are preferably from a parvoviral capsid, such as an AAV capsid or a chimeric AAV capsid function. Examples of suitable parvovirus viral capsid components are capsid components from the family parvoviridae, such as an autonomous parvovirus or a dependovirus. For example, the capsid components may be selected from AAV capsids, AAV1-AAV12 and other novel capsids as yet unidentified or from non-human primate sources. Capsid components may include components from two or more AAV capsids.

In certain embodiments, one or more of the VP capsid proteins may comprise chimeric proteins, comprising amino acid sequences from two or more viruses, preferably two or more AAVs. For example, the chimeric virus capsid can include a capsid region from an adeno-associated virus (AAV) and at least one capsid region from a B19 virus. The chimeric capsid can, for example, include an AAV capsid with one or more B19 capsid subunits, e.g., an AAV capsid subunit can be replaced by a B19 capsid subunit. For example, the VP1, VP2 or VP3 subunit of the AAV capsid can be replaced by the VP1, VP2 or VP3 subunit of B19. As another example, the chimeric capsid may include an AAV type 2 capsid in which the type 2 VP1 subunit has been replaced by the VP1 subunit from an AAV type 1, 3, 4, 5, or 6 capsid, preferably a type 3, 4, or 5 capsid. Alternatively, the chimeric parvovirus has an AAV type 2 capsid in which the type 2 VP2 subunit has been replaced by the VP2 subunit from an AAV type 1, 3, 4, 5, or 6 capsid, preferably a type 3, 4, or 5 capsid. Likewise, chimeric parvoviruses in which the VP3 subunit from an AAV type 1, 3, 4, 5 or 6 (more preferably, type 3, 4 or 5) is substituted for the VP3 subunit of an AAV type 2 capsid are preferred. As a further alternative, chimeric parvoviruses in which two of the AAV type 2 subunits are replaced by the subunits from an AAV of a different serotype AAV type 1, 3, 4, 5 or 6) are preferred. In exemplary chimeric parvoviruses according to this embodiment, the VP1 and VP2, or VP1 and VP3, or VP2 and VP3 subunits of an AAV type 2 capsid are replaced by the corresponding subunits of an AAV of a different serotype (e.g., AAV type 1, 3, 4, 5 or 6). Likewise, in other preferred embodiments, the chimeric parvovirus has an AAV type 1, 3, 4, 5 or 6 capsid (preferably the type 2, 3 or 5 capsid) in which one or two subunits have been replaced with those from an AAV of a different serotype, as described above for AAV type 2.

The packaged viral vector generally includes the mutant FVIII sequence and expression control sequences flanked by TR elements sufficient to result in packaging of the vector DNA and subsequent expression of the mutant FVIII sequence in the transduced cell. The viral vector functions may, for example, be supplied to the cell as a component of a plasmid or an amplicon. The viral vector functions may exist extrachromosomally within the cell line and/or may be integrated into the cells' chromosomal DNA.

IV. Methods and Cell Lines for mhFVIII Protein Production

Another aspect of the present application relates to a method of making a mhFVIII of the present application. This entails growing a host cell of the present application under conditions, whereby the host cell is transformed by an expression vector to express the mhFVIII. The expressed mhFVIII is then isolated.

A further aspect of the present application relates to a host cell including an isolated nucleic acid molecule encoding the mhFVIII of the present application. The host cell can contain the isolated nucleic acid molecule as a DNA molecule in the form of an episomal plasmid or it can be stably integrated into the host cell genome. Further, the host cell can constitute an expression system for producing the mhFVIII protein. Suitable host cells can be, without limitation, animal cells (e.g., human HuH7 and HEK293 cells, Chinese hamster ovary cells ("CHO"), baby hamster kidney ("BHK") cells), bacterial cells (e.g., *E. coli*), insect cells (e.g., Sf9 cells), fungal cells, yeast cells (e.g., *Saccharomyces* or *Schizosaccharomyces*), plant cells (e.g., *Arabidopsis* or tobacco cells), algal cells and the like. Mammalian cells suitable for carrying out the present application include, among others: COS (e.g., ATCC No. CRL 1650 or 1651), BHK (e.g., ATCC No. CRL 6281), CHO (ATCC No. CCL 61), HeLa (e.g. ATCC No. CCL 2), 293 (ATCC No. 1573), CHOP, HuH7, HEK293 and NS-1 cells.

Another aspect of the present application relates to a method for producing a mhFVIII from culture cells. In some embodiments, the method comprises the steps of: (a) introducing into host cells an expression vector comprising: a polynucleotide comprising a nucleotide sequence encoding a signal peptide and a nucleotide sequence encoding the mhFVIII, wherein the mhFVIII comprises one or more amino acid substitutions at positions selected from the group consisting of A20K, T21I, T21V, F57L, L69V, I80V, L178F, R199K, H212Q, I215V, R269K, I310V, I318F, S332P, R378S, I610M and I661V; and a regulatory sequence operatively linked to the polynucleotides; (b) growing the host cells harboring the expression vector under conditions suitable for expression and. secretion of the mhFVIII; and (c) harvesting culture medium of the host cells and/or the host cell, and (d) purifying the mhFVIII from the harvested culture medium and/or the host cell.

In one embodiment, the host cell is grown in vitro in a growth medium. Suitable growth media may include, without limitation, a growth medium containing a von Willebrand Factor (referred to herein as "VWF"). In this embodiment, the host cell can contain a transgene encoding a VWF or the VWF can be introduced to the growth medium as a supplement. VWF in the growth medium will allow for greater expression levels of the mhFVIII. Once the recombinant FVIII is secreted into the growth medium, it can then be isolated from the growth medium using techniques well-known by those of ordinary skill in the relevant recombinant DNA and protein arts (including those described herein). In another embodiment, the method of making the mhFVIII of the present application further involves disrupting the host cell prior to isolation of the mhFVIII. In this embodiment, the mhFVIII is isolated from cellular debris.

The mhFVIII is preferably produced in a substantially pure form. In a particular embodiment, the substantially pure recombinant FVIII is at least about 80% pure, more preferably at least 90% pure, most preferably at least 95% pure, 98% pure, 99% pure or 99.9% pure. A substantially pure recombinant FVIII can be obtained by conventional techniques well known in the art. Typically, the substantially pure mhFVIII is secreted into the growth medium of recombinant host cells. Alternatively, the substantially pure mhFVIII is produced but not secreted into growth medium. In such cases, to isolate the substantially pure mhFVIII, the host cell carrying the recombinant plasmid is propagated, lysed by sonication, heat, or chemical treatment, and the homogenate is centrifuged to remove cell debris. The supernatant is then subjected to sequential ammonium sulfate precipitation. The fraction containing the substantially pure mhFVIII is subjected to gel filtration in an appropriately sized dextran or polyacrylamide column to separate the mhFVIII. If necessary, a protein fraction (containing the substantially pure mhFVIII) may be further purified by high performance liquid chromatography ("HPLC").

V. Methods of Treatment

Another aspect of the present application relates to a method for treating a patient with a FVIII deficiency.

In some embodiments, the method comprises the step of administering to a patient in need thereof an effective amount of a mhFVIII of the present application. In some embodiments, the mhFVIII is administered intravenously in a purified form.

In other embodiments, the method comprises the step of administering to a patient in need thereof an effective amount of an expression vector comprising a coding sequence of a mhFVIII of the present application, wherein the expression vector is capable of expressing the mhFVIII in the patient.

In other embodiments, the method comprises the step of administering to a patient in need thereof an effective amount of cells comprising a coding sequence of a mhFVIII of the present application, wherein the cells are capable of expressing the mhFVIII in the patient after transplantation. In some embodiments, the cells are dermal fibroblasts. In some embodiments, the cells are autologous cells. In some embodiments, the method comprises the steps of introducing a coding sequence into a population of target cells, wherein the target cells are isolated from a subject in need of such treatment, expressing the mhFVIII in the target cells, and infusing an effective amount of the mhFVIII-expressing cells into the subject.

In same embodiments, the FVIII deficiency is hemophilia A. In this case, expression of the mhFVIII of the present application can enhance clotting in the patient who is otherwise vulnerable to uncontrolled bleeding due to FVIII deficiency (e.g., intraarticular, intracranial, or gastrointestinal hemorrhage), including hemophiliacs who have developed antibodies to human FVIII. The target cells of the vectors are cells capable of expressing polypeptides with FVIII activity, such as those of the hepatic system of a mammal, endothelial cells and other cells with the proper cellular machinery to process the precursor to yield protein with FVIII activity.

Administration of the mhFVIII proteins or mhFVIII-encoding expression vectors or mhFVIII-expressing cells to FVIII deficient patients can functionally reconstitute the coagulation cascade. The mhFVIII proteins or mhFVIII-encoding expression vectors or mhFVIII-expressing cells may be administered alone or in combination with other therapeutic agents in a pharmaceutically acceptable or biologically compatible composition.

In some embodiment, the method comprises administering a pharmaceutical composition comprising a mhFVIII protein into the patient intravenously according to the same procedure that is used for infusion of human or animal FVIII. A suitable effective amount of the mhFVIII can include, without limitation, between about 10 to about 500 units/kg body weight of the patient.

Treatment dosages of the mhFVIII-encoding expression vectors or mhFVIII proteins or mhFVIII expressing cells will vary depending on the severity of the FVIII deficiency. Generally, dosage level is adjusted in frequency, duration, and units in keeping with the severity and duration of each patient's bleeding episode. Accordingly, mhFVIII-encoding expression vectors or mhFVIII proteins or mhFVIII expressing cells is included in a pharmaceutically acceptable carrier, delivery vehicle, or stabilizer in an amount sufficient to deliver to a patient a therapeutically effective amount of the protein to stop bleeding, as measured by standard clotting assays.

FVIII is classically defined as that substance present in normal blood plasma that corrects the clotting defect in plasma derived from individuals with hemophilia A. The coagulant activity in vitro of purified and partially-purified forms of FVIII is used to calculate the dose of mhFVIII for infusions in human patients and is a reliable indicator of activity recovered from patient plasma and of correction of the in vivo bleeding defect. There are no reported discrepancies between standard assay of novel FVIII molecules in vitro and their behavior in the dog infusion model or in human patients.

Usually, the desired plasma FVIII activity level to be achieved in the patient through administration of the mhFVIII is in the range of 30-200% of normal. In one embodiment, administration of the therapeutic mhFVIII is given intravenously at a preferred dosage in the range from about 5 to 500 units/kg body weight, and particularly in a range of 10-100 units/kg body weight, and further particularly at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. Patients with inhibitors may require a different amount of mhFVIII than their previous form of FVIII. For example, patients may require less mhFVIII because of its higher specific activity than the wild-type VIII and its decreased antibody reactivity. As in treatment with human or plasma-derived FVIII, the amount of therapeutic mhFVIII infused is defined by the one-stage FVIII coagulation assay and, in selected instances, in vivo recovery is determined by measuring the FVIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed mhFVIII.

Treatment can take the form of a single intravenous administration of the mhFVIII or periodic or continuous administration over an extended period of time, as required. Alternatively, therapeutic mhFVIII can be administered subcutaneously or orally with liposomes in one or several doses at varying intervals of time Administration of an expression vector to a human subject or an animal in need can he by any means known in the art for administering virus vectors. Exemplary modes of administration include rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

In certain preferred embodiments, the expression vector is administered intramuscularly, more preferably by intramuscular injection or by local administration. The vectors disclosed herein may be administered to the lungs of a subject by any suitable means, but are preferably administered by administering an aerosol suspension of respirable particles comprised of the inventive parvovirus vectors, which the subject inhales. The respirable particles may be liquid or solid. Aerosols of liquid particles comprising the inventive parvovirus vectors (e.g., AAV) may be produced by any suitable means, such as with a pressure-driven aerosol nebulizer or an ultrasonic nebulizer, as is known to those of skill in the art. See, e.g., U.S. Pat. No. 4,501,729.

Dosages of viral vectors expressing mhFVIII will depend upon the mode of administration, the disease or condition to be treated, the individual subject's condition, the particular viral vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units.

Polynucleotides encoding a mtFVIII of the present application may be administered as components of a DNA molecule having regulatory elements appropriate for expression in the target cells. The polynucleotides encoding a mtFVIII of the present application may be administered as components of viral plasmids or viral particles, such as AAV particles. Viral particles may be administered as viral particles alone by direct in vivo direct delivery to the portal vasculature of a subject in need thereof or as an ex vivo treatment comprising transduction of cells with the viral particles ex vivo followed by introduction of the transduced cells back into the subject in vivo.

The mtFVIII-encoding polynucleotides can be employed as a single chain molecule containing both heavy and light chain portions or split into two or multiple molecules (e.g., heavy and light chain) in multiple independent viral or non-viral vectors for delivery into host cells of the patient.

In some embodiments, the expression vector is a viral vector. Viral vectors which may be used in the present application include, but are not limited to, adeno-associated virus (AAV) vectors of multiple serotypes (e.g., AAV-1 to AAV-12, and pseudo-typed vectors thereof), hybrid AAV vectors, retroviral vectors, including lentivirus vectors and pseudo-typed lentivirus vectors (e.g., human immunodeficiency virus (HIV) and feline immunodeficiency virus (FIV)); adenoviral vectors, herpes simplex virus vectors, vaccinia virus vectors, non-viral vectors and others. In addition, any of the viral vectors may be modified to include tissue specific promoters/enhancers etc.

VI. Pharmaceutical Compositions

Another aspect of the present application relates to a pharmaceutical composition comprising (1) a mhFVIII polypeptide, a mhFVIII-encoding expression vector, or mhFVIII-expressing cells of the present application, and (2) a pharmaceutically-acceptable carrier.

Exemplary pharmaceutically acceptable carriers include sterile, pyrogen-free water and sterile, pyrogen-free, phosphate buffered saline. Physiologically-acceptable carriers include pharmaceutically-acceptable carriers. Pharmaceutically acceptable carriers are those which are that is not biologically or otherwise undesirable, i.e., the material may be administered to a subject without causing undesirable biological effects which outweigh the advantageous biological effects of the material. In some embodiments, the pharmaceutical composition is formulated for injection.

For injection, the carrier will typically be a liquid. As an injection medium, it is preferred to use water that contains the additives usual for injection solutions, such as stabilizing agents, salts or saline, and/or buffers. For other methods of administration, the carrier may be either solid or liquid. For inhalation administration, the carrier will be respirable, and will preferably be in solid or liquid particulate form.

The present application is further illustrated by the following examples which should not be construed as limiting. The contents of all references, patents, and published patent applications cited throughout this application are incorporated herein by reference.

EXAMPLES

Example 1: Construction, Expression and Characterization of Factor VIII Mutants

Figure 3:
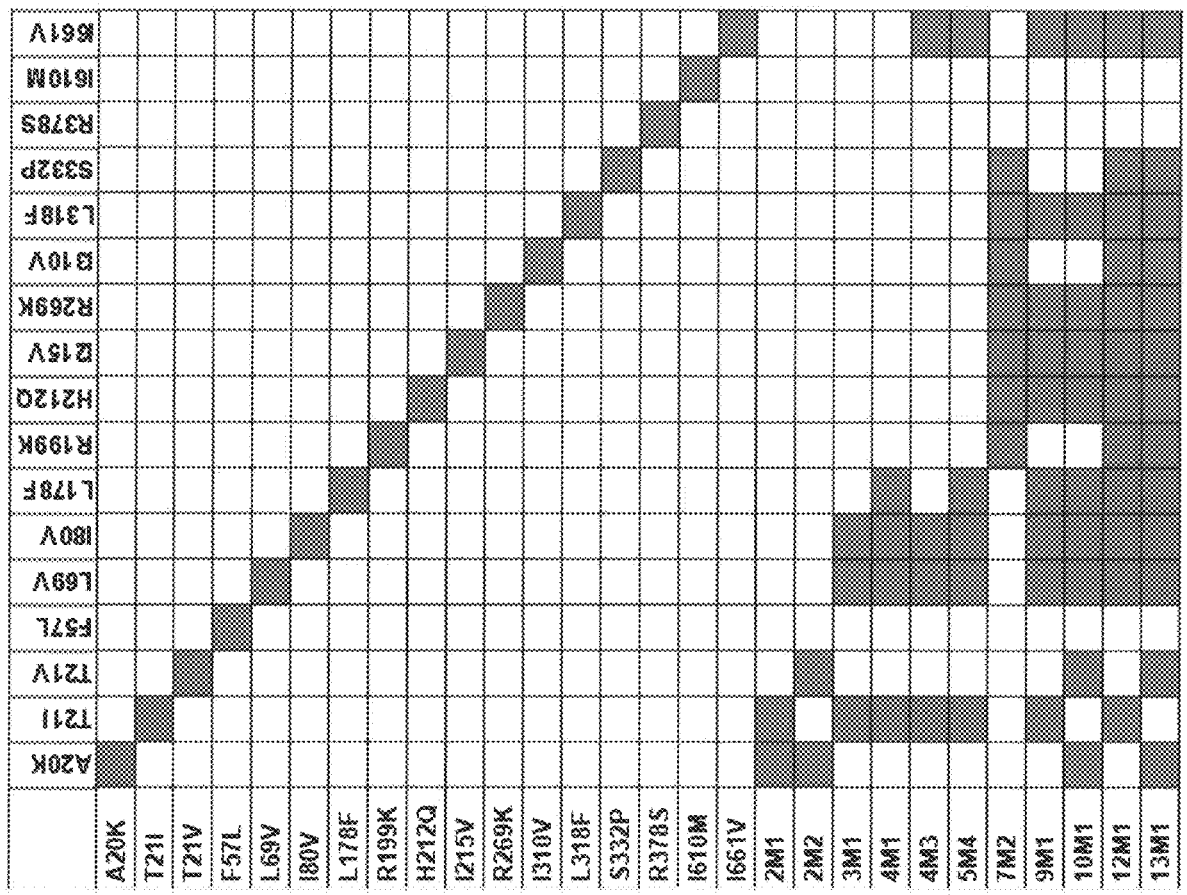

Template: Plasmid pANG-CAG-hBDDF8 was used as a template for introducing multiple hFVIII mutations into the coding region of the hFVIII heavy chain. As shown in FIG. 1, pANG-CAG-hBDDF8 (SEQ ID NO:15) contains a human factor VIII (hBDDF8) cDNA is under the control of a GAG promoter. In addition, pANG-CAG-hBDDF8 carries a deletion in the B-domain resulting in a functionally deficient B-domain. FIG. 2 identities hFVIII mutations that were constructed in pANG-CAG-hBDDF8. FIG. 3 shows both hFVIII mutations analyzed in the present study, including both single amino acid substitutions and combinations thereof.

Single mutations: The GIBSON ASSEMBLY® method was used to introduce individual mutations corresponding to A20K, T21I, T21V, F57L, L69V, I80V, L178F, R199K, H212Q, I215V, R269K, I310V, L318F, S332P, R378S, I610M, and I661V of human factor VIII into the pANG-CAG-hBDDF8 plasmid. The resulting plasmids include pANG-CAG-hBDDP8-A20K, pANG-CAG-hBDDF8, pANG-CAG-hBDDF8-T21I, pANG-CAG-hBDDF8-T21V, pANG-CAG-hBDDF8-F57L, pANG-CAG-hBDDF8-L69V, pANG-CAG-hBDDF8-I80V, pANG-CAG-hBDDF8-L178F, pANG-CAG-hBDDF8-R199K, pANG-CAG-hBDDF8-H212Q, pANG-CAG-hBDDF8-I215V, pANG-CAG-hBDDF8-R269K, pANG-CAG-hBDDF8-I310V, pANG-CAG-hBDDF8-L318F, pANG-CAG-hBDDF8-S332P, pANG-CAG-hBDDF8-R378S, pANG-CAG-hBDDF8-I610M, pANG-CAG-hBDDF8-I661V.

T21 mutants: An AvrII restriction site was introduced in pANG-CAG-hBDDF8 by replacing T21 with P. The resulting plasmid, pANG-CAG-hBDDF8-T21P was used as a template to create multiple point mutations in amino acid position 21. pANG-CAG-hBDDF8-T21P was digested by AvrII and used as a template for the mutant constructions described herein. 19 oligonucleotides with NNN corresponding to T21 position were recombined into pANG-CAG-hBDDF8 by HIFI assembly. Mutant plasmids include pANG-CAG-hBDDF8 T21V, pANG-CAG-hBDDF8-T21I . . . pANG-CAG-hBDDF8-T21G, etc. The last letter indicates the amino acid substitution at that particular position. A similar strategy can be used to generate other substitutions in accordance with the present invention.

A20 mutations with T21I: 19 oligonucleotides with T21I and NNN corresponding to Alanine 20 were recombined into pANG-CAG-hBDDF8-T21P digested by AvrII by HIFI assembly. The resulting mutant plasmids include pANG-CAG-hBDDF8-A20K/T21I(2M1), pANG-CAG-hBDDF8-A20E/T21I . . . pANG-CAG-hBDDF8-A20V/T21I, etc. A similar strategy can be used to generate other substitutions in accordance with the present invention, such as pANG-CAG-hBDDF8-A20K/T21V (2M2)

Combinations of mutations. hFVIII mutants with multiple HC mutations (as shown in FIG. 3) were constructed in pANG-CAG-hBDDF8. In one embodiment, a DNA fragment encoding the substitution mutations A20K, T21V, L69V, I80V, L178F, R199K, H212Q, I215V, R269K, I310V, L318F, S332P and I661V was chemically synthesized and used to replace the corresponding region in pANG-CAG-hBDDF8. The resulting plasmid, pANG-CAG-BDDF8-13M1, expresses a mutant factor VIII protein with the above 13 mutations (13M1).

In another embodiment, a DNA fragment encoding the substitution mutations T21I, L69V, I80V, L178F, R199K, H212Q, I215V, R269K, I310V, L318F, S332P and I661V was chemically synthesized and used to replace the corresponding region of pANG-CAG-hBDDF8. The resulting plasmid, pANG-CAG-BDDF8-12M1, expresses a mutant factor VIII protein with the above 12 mutations (12M1).

In another embodiment, a DNA fragment encoding the substitution mutations A20K, T21V, L69V, I80V, L178F, H212Q, I215V, R269K, L318F, and I661V was chemically synthesized and used to replace the corresponding region of pANG-CAG-hBDDF8. The resulting plasmid, pANG-CAG-BDDF8-10M1, expresses a mutant factor VIII protein with the above 10 mutations (10M1).

In another embodiment, a DNA fragment encoding the substitution mutations T21I, L69V, I80V, L178F, H212Q, I215V, R269K, I318F, and I661V was chemically synthesized and used to replace the corresponding region of pANG-CAG-hBDDF8. The resulting plasmid, pANG-CAG-BDDF8-9M1, expresses a mutant factor VIII protein with the above 9 mutations (9M1).

In another embodiment, a DNA fragment encoding the substitution mutations R199K, H212Q, I215V, R269K, I310V, L318F, and S332P was chemically synthesized and used to replace the corresponding region of pANG-CAG-hBDDF8. The resulting plasmid, pANG-CAG-BDDF8-7M2, expresses a mutant factor VIII protein with the above 7 mutations (7M2).

In another embodiment, a DNA fragment encoding the substitution mutations T21I, L69V, I80V, L178F, and I661V was chemically synthesized and used to replace the corresponding region of pANG-CAG-hBDDF8. The resulting plasmid, pANG-CAG-BDDF8-5M4, expresses a mutant factor VIII protein with the above 5 mutations (5M4).

In another embodiment, a DNA fragment encoding the substitution mutations T21V, L69V, I80V and I661V was synthesized chemically and used to replace the corresponding region of pANG-CAG-hBDDF8. The resulting plasmid, pANG-CAG-BDDF8-4M3, expresses a mutant factor VIII protein with the above 4 mutations (4M3).

In another embodiment, a DNA fragment encoding the substitution mutations T21I, L69V, I80V and L178F was synthesized chemically and used to replace the corresponding region of pANG-CAG-hBDDF8. The resulting plasmid, pANG-CAG-BDDF8-4M1, expresses a mutant factor VIII protein with the above 4 mutations (4M1).

In another embodiment, a DNA fragment encoding the substitution mutations T21I, L69V and I80V was synthesized chemically and used to replace the corresponding region of pANG-CAG-hBDDF8. The resulting plasmid, pANG-CAG-BDDF8-3M1, expresses a mutant factor VIII protein with the above 3 mutations (3M1).

To test the functional activity of the mutant constructions, HEK 293T, HuH7 and CHO cells were cultured in DMEM with 10% fetal bovine serum, penicillin (100 U/ml) and streptomycin (100 μg/ml) at 37° C. in a moist environment supplied with 5% $CO_2$. HEK 293T, HuH7 and CHO cells were transfected with wild-type and mutant expression constructs in pANG-CAG-hDDF8. Following transfection, the cells were maintained in RPMI-1640 media with 2% inactivated fetal bovine serum. Cell culture media were collected at different times (24 h, 48 h, 72 h) post transfection. Secreted FVIII activities were analyzed using the activated partial thromboplastin time (APTT) assay. Normal human plasma was used as a standard.

Figure 4:
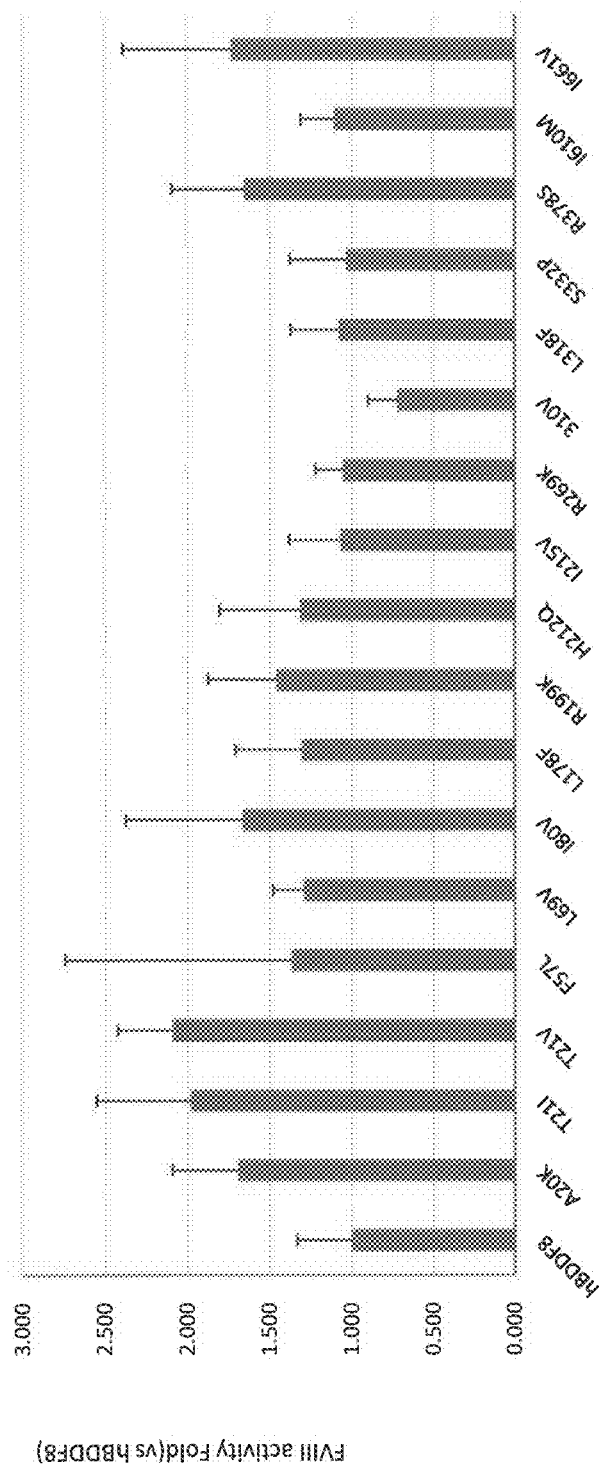
Figure 5:
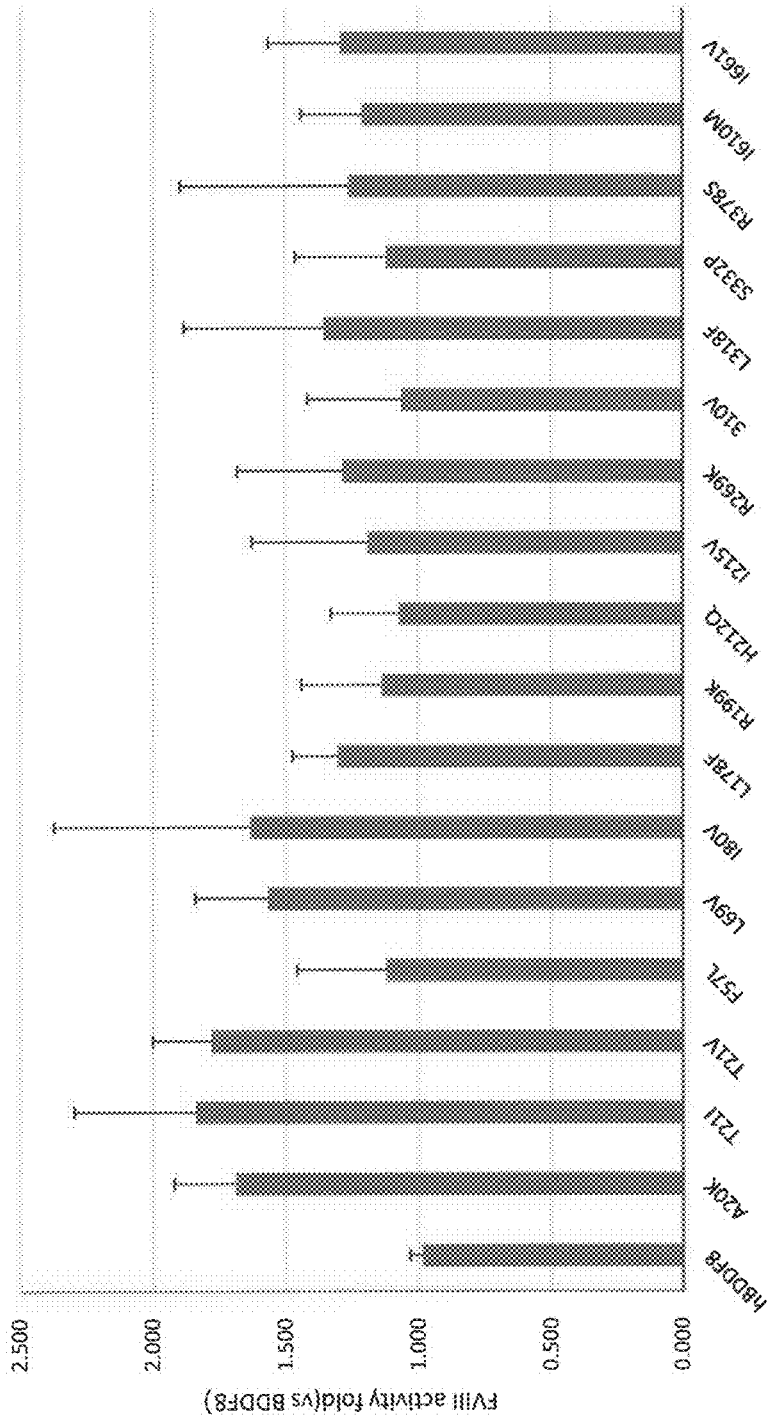
Figure 6:
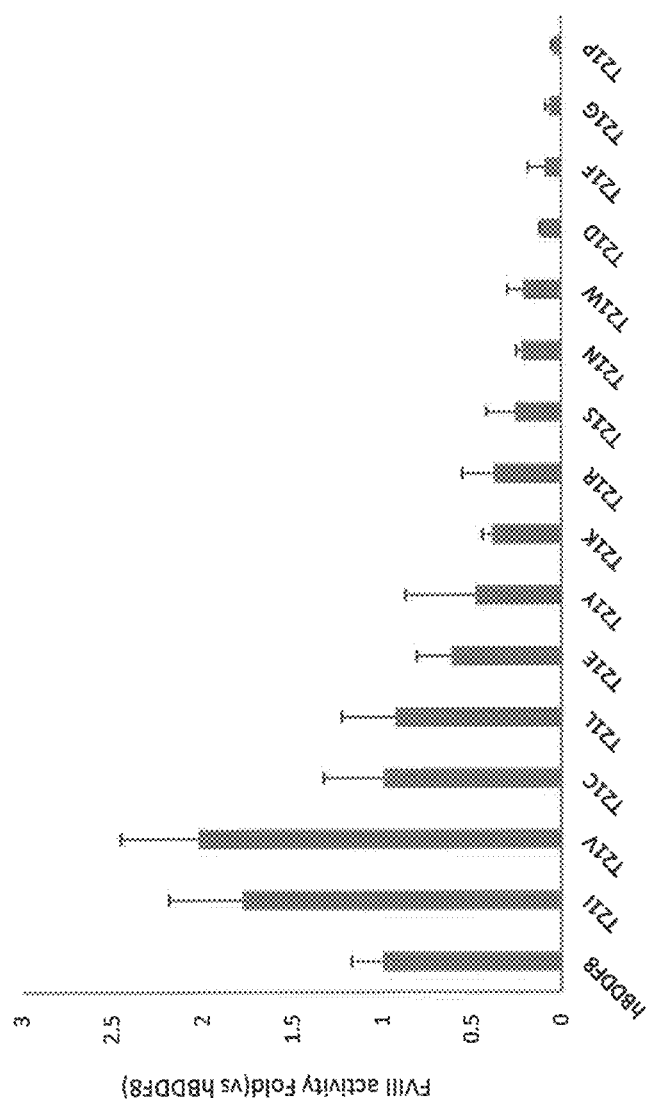
Figure 7:
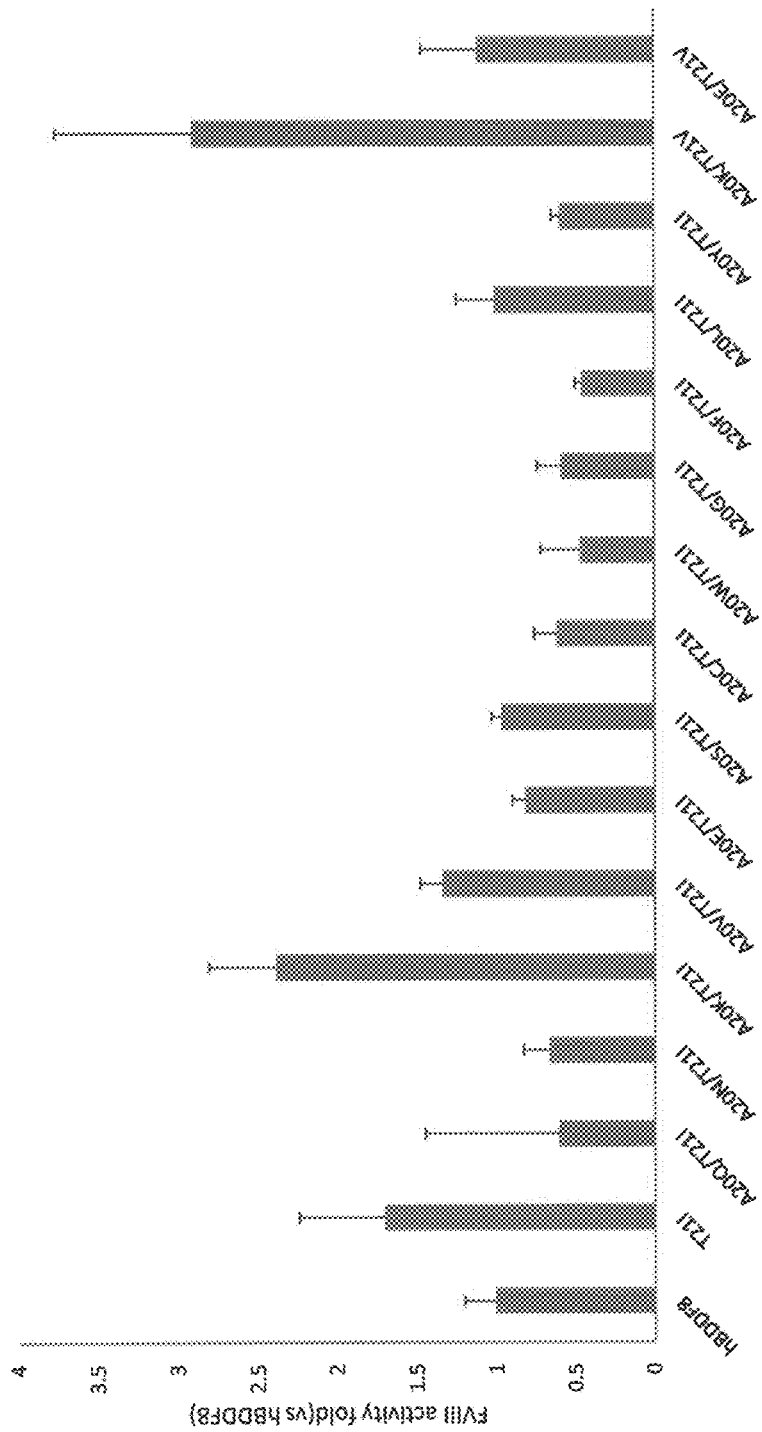
Figure 8:
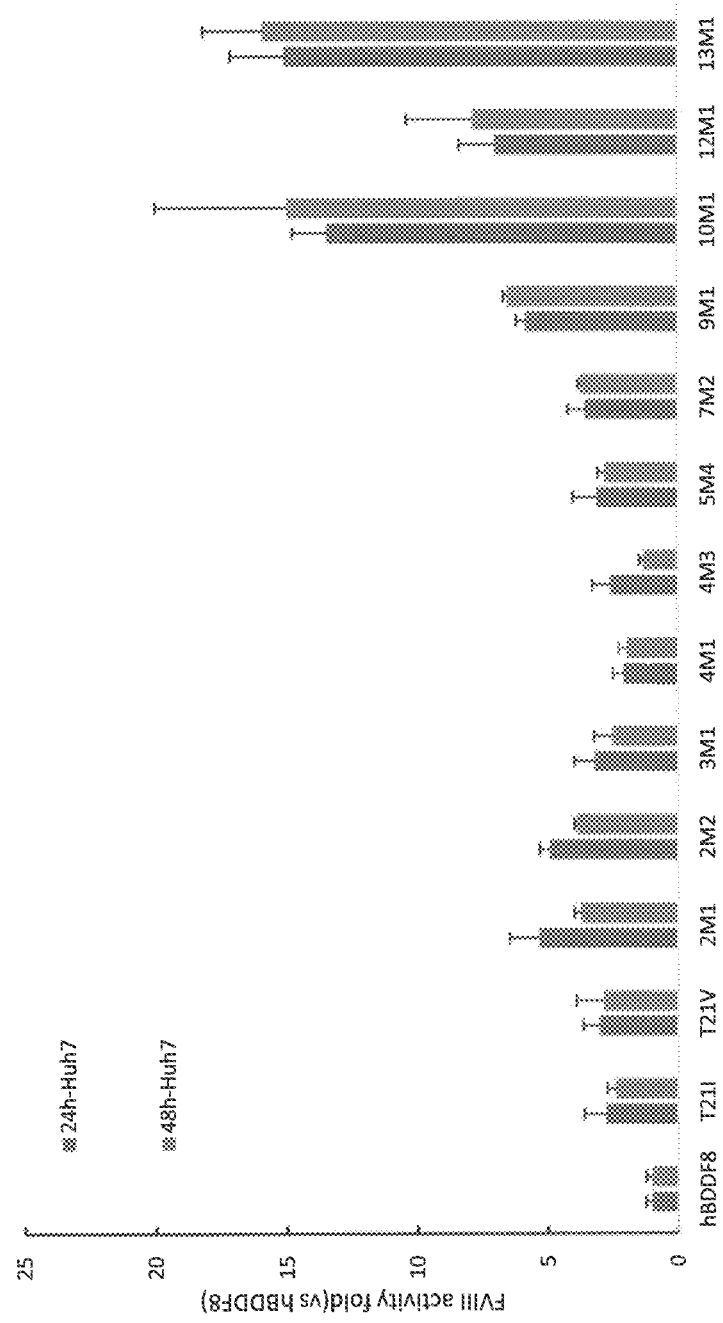
Figure 9:
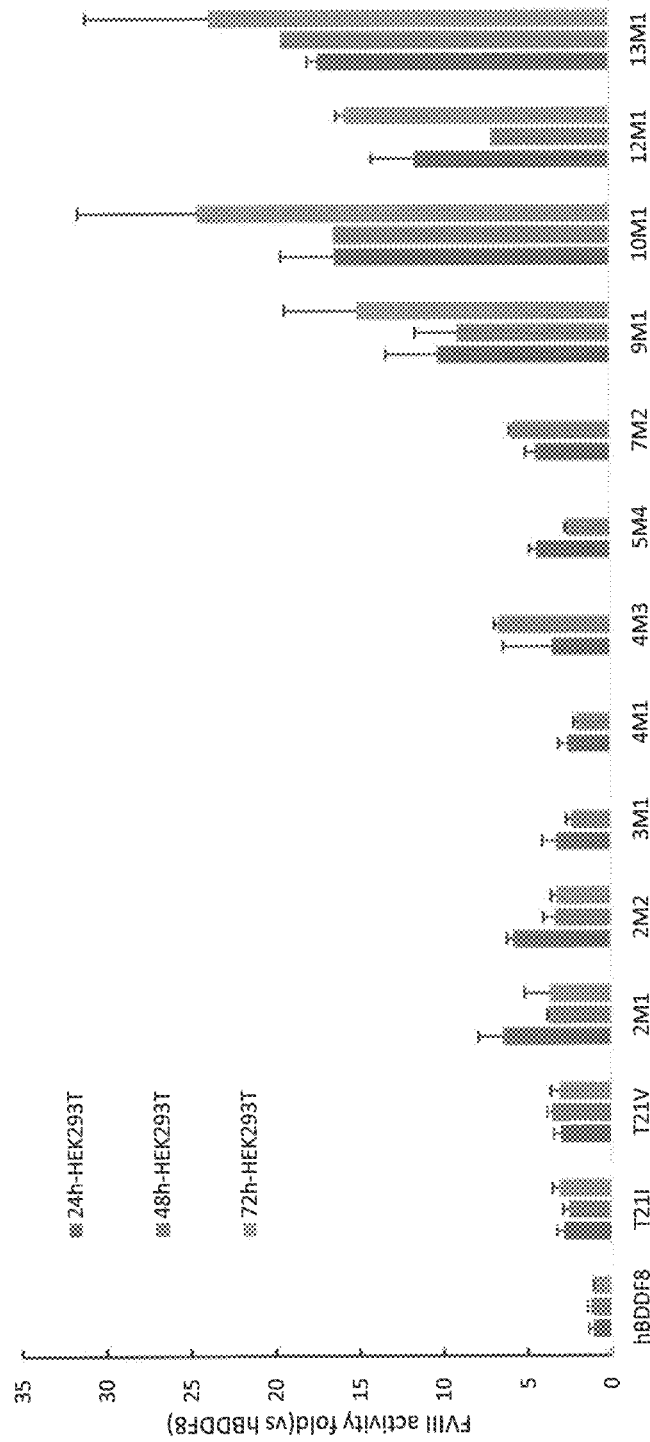
Figure 10:
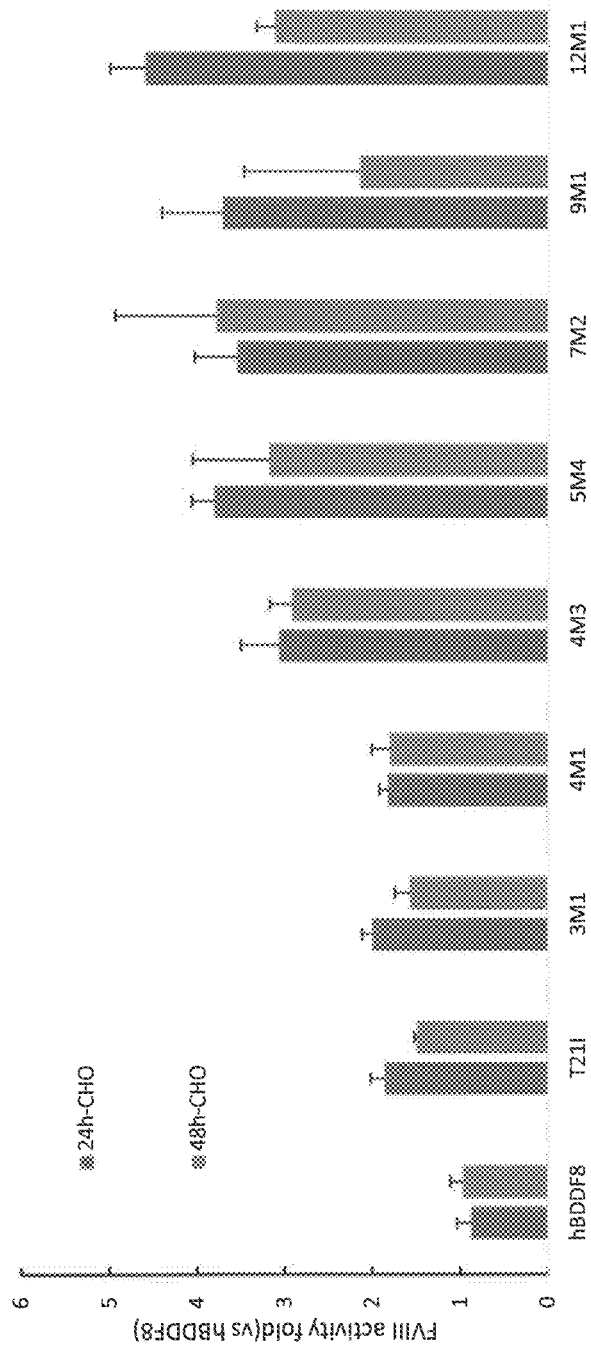

Representative results of these assays are shown in FIGS. 4-10, 11B and 13. Briefly, FIGS. 4-6 show increased functional activities of specific single amino acid substitution mutants in HuH7 cells (FIG. 4) and HEK 293T cells (FIGS. 5, 6) compared to wild-type hFVIII at 48 hr post-transfection. FIG. 6 shows that T21I and T21V mutants significantly increased FVIII activity in HEK 293T cells at 48 hr post-transfection. FIG. 7 shows that A20K-bearing double mutants (A20K/T21I and A20K/T21V) further increased FVIII activity in HEK 293T cells relative to the T21 and T21V single substitution counterparts at 48 hr post-transfection. FIGS. 8-10 show that combinations of multiple mutations can greatly increase FVIII functional activity compared to wild-type, single substitution and double substitution mutants in HuH7, HEK 293T, and CHO cells, respectively at 24 hr and 48 hr post-transfection.

Example 2: Construction, Expression and Functional Activities of Hybrid Human/Canine Factor VIII Mutants To evaluate the functional activities of mutant hVIIIs of the present application compared to mutant hybrid human/canine FVIII consisting of a mutant hVIII heavy chain (hHC) and a canine FVIII light chain (cLC), a series of B-domainless FVIII constructs were prepared and expressed in HEK 293T cells as shown in FIGS. 11A and 11B.

Briefly, mutant FVIIIs were constructed that contain a mutant human FVIII heavy chain and a canine FVIII light chain. Briefly, pANG-CAG-hBDDF8 was digested with CspCI and XhoI. A DNA fragment encoding a canine light chain (cLC) was chemically synthesized and used to replace the corresponding human light (hLC) region in pANG-CAG-hBDDF8 by Gibson assembly. The resulting plasmid, pANG-CAG-hHC-cLC, expresses a B-domainless hybrid human/canine factor VIII polypeptide composed of an hHC and a cLC (i.e., hHC-cLC). SEQ ID NO:10 shows the amino acid sequence of the hHC-cLC protein with a native hFVIII signal peptide. SEQ ID NO:11 shows a cDNA sequence encoding the protein in SEQ ID NO:10. SEQ ID NO:12 shows the amino acid sequence of the hHC-cLC protein without the hFVIII signal peptide. SEQ ID NO:13 shows the amino acid sequence of the truncated B-domain in the hHC-cLC protein and SEQ ID NO:14 shows the amino acid sequence of the canine FVIII light chain (cLC).

Figure 11A:
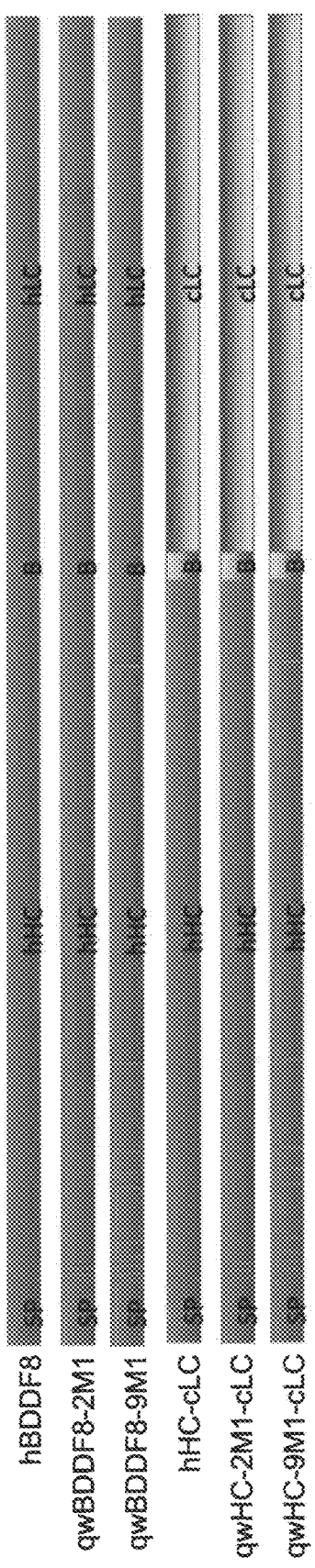
Figure 11B:
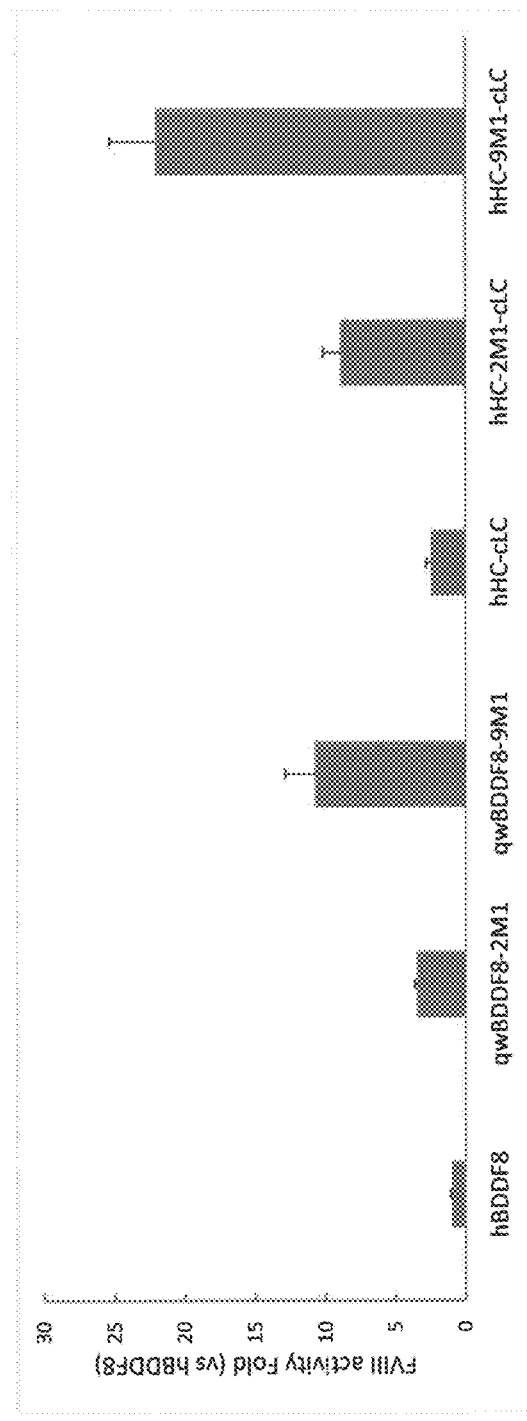

A similar strategy was used to generate pANG-GAG-qwHC-2M1-cLC (2M1 mutant) and pANG-CAG-qwHC-9M1-cLC (9M1 mutant) plasmids as shown (and abbreviated) in FIG. 11A. Secreted FVIII activities were analyzed using the activated partial thromboplastin time (APTT) assay. FIG. 11B shows the functional activities of various human/canine hybrid FVIII mutants in HEK 293T cells, compared to the functional activity of hFVIII (i.e., unmodified hBDDF8 protein) at 48 hr post-transfection. As shown in FIG. 11B, substitution of the hLC with cLC in this system resulted in increased FVIII activity compared to the hFVIIIs expressed from the parent plasmid, hBDDF8.

In another aspect, the functional activities of rAAV vectors expressing mutant hVIIIs of the present application compared to rAAV vectors expressing parent hBDDF8. In this case, a series of rAAVs expressing hBDDF8 protein and modified hBDDF8 proteins and were constructed and produced. The resulting rAAVs were used to infect Huh7 cells and the hVIII activities in the infected cells were analyzed.

In this case, a first series of rAAVs expressing mutant hVIIIs of the present application were constructed in which the CAG promoter in hBDDF8 was substituted with a human TTR promoter. Briefly, pANG-CAG-hBDDF8 was digested with SnaBI and MluI. A DNA fragment encoding TTR promoter and intron was chemically synthesized and used to replace the GAG promoter region in pANG-CAG-hBDDF8 by Gibson assembly.

Figure 12:
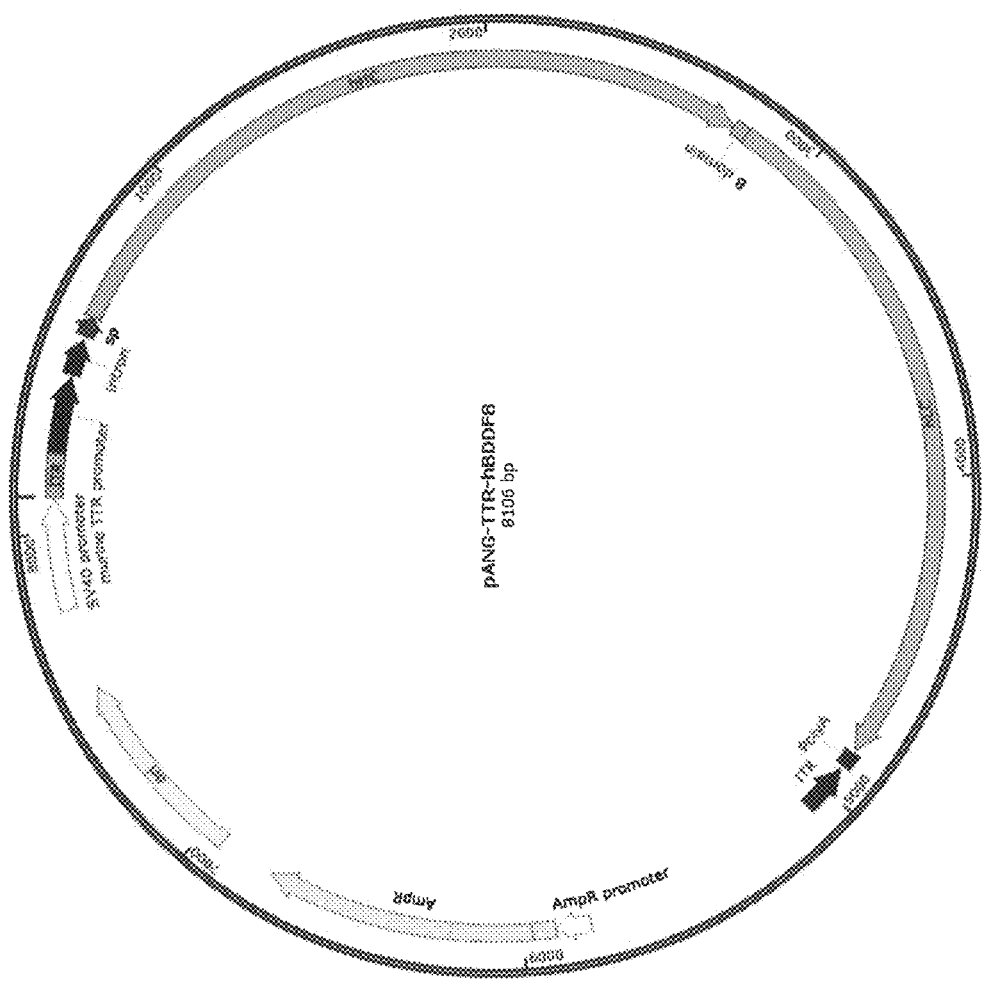

As shown in FIG. 12, the resulting plasmid, pANG-TTR-hBDDF8 (SEQ ID NO:18), expresses hBDDF8 protein under the control of the TTR promoter. A similar strategy was used to generate pANG-TTR-qwBDDF8-2M1, pANG- TTR-qwBDDF8-2M2, pANG-TTR-qwBDDF8-9M1, pANG-TTR-qwBDDF8-10M1, pANG-TTR-qwBDDF8-12M1, pANG-TTR-qwBDDF8-13M1 plasmids.

The pANG-TTR-hBDDF8 and the modified variant plasmids thereof were packaging with an AAV2 capsid to produce rAAVs therefrom. Briefly, pAAV-Rep&Cap (serotype 2), pAd helper, and the transgene plasmids were co-transfected into HEK 293T cells cultured in roller bottles at a ratio of 1:1:1. rAAVs from the transfected cell media were harvested at 72 hrs post transfection and purified by two rounds of CsCl gradient ultracentrifuge. Each of the rAAVs was collected and extensively exchanged against PBS with 5% D-sorbitol.

HuH7 cells were grown in DMEM (Invitrogen, Carlsbad, Calif.) with 10% FBS, penicillin (100 U/ml), and streptomycin (100 µg/ml) at 37° C. in a moisturized environment supplied with 5% $CO_2$. For each transduction experiment, 50,000 viable cells were seeded in a 24 well plate 24 hrs before transduction, rAAVs were added directly to each well with 100,000 vg/cell. Secreted FVIII activities were analyzed at 72 hrs post-transfection using the activated partial thromboplastin time (APTT) assay.

Figure 13:
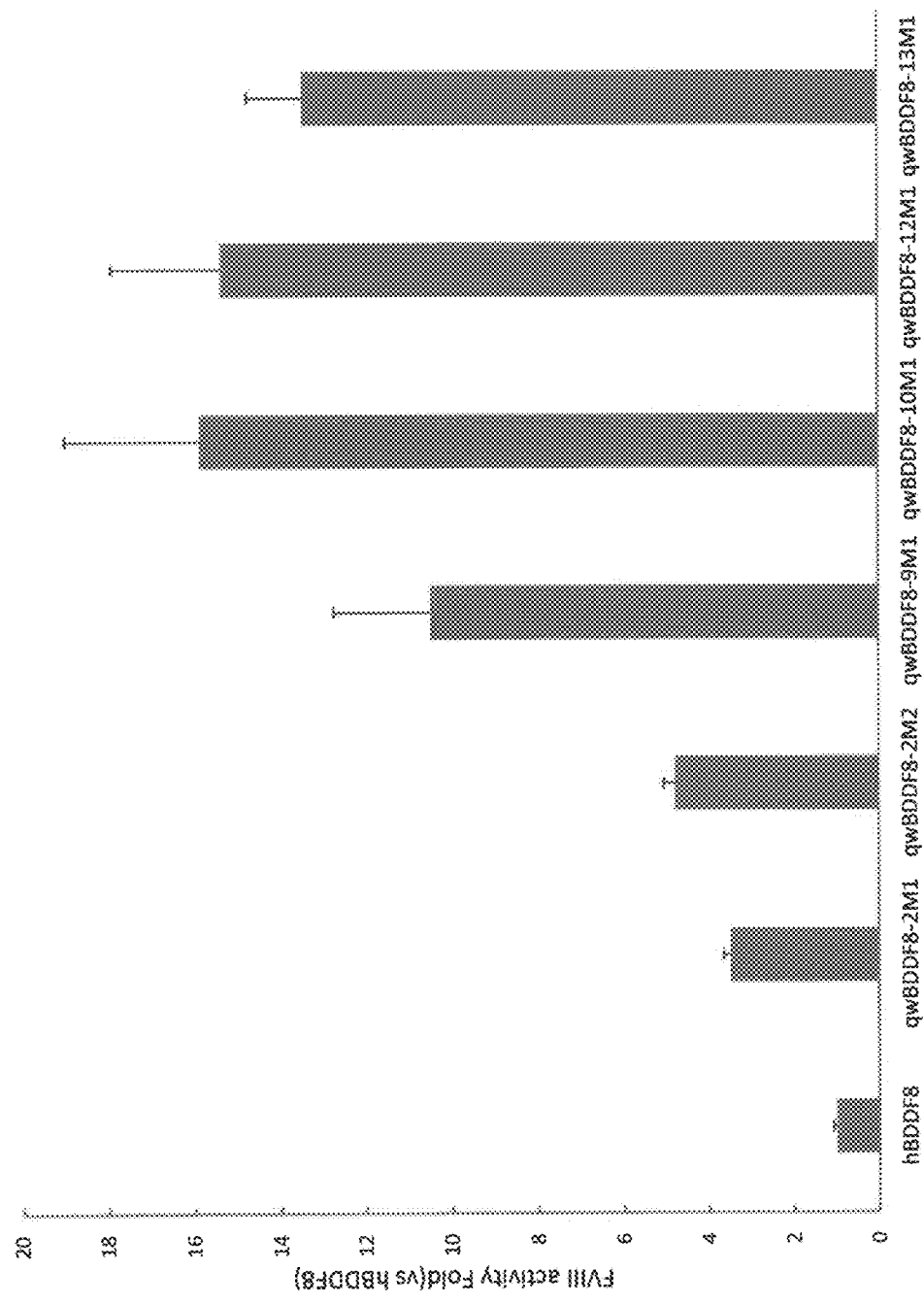

As shown in FIG. 13, modified hBDDF8 exhibited increased activity compared to unmodified hBDDF8, when expressed by rAAV vectors in Huh7 cells.

The above Examples show that the mutant factor VIII products of the present application exhibit increased functional activity compared to wild type factor VIII. Therefore, use of the mutants described herein can decrease the production cost and the levels of FVIII expression needed relative to existing constructions. They can also allow lower vector doses to be administered by providing higher activity FVIII products.

The above description is for the purpose of teaching a person of ordinary skill in the art how to practice the present application. It is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the claimed components and steps in any sequence effective to meet the objectives there intended, unless the context specifically indicates the contrary.

What is claimed is:

1. A modified human factor VIII (mhFVIII), comprising:
   (1) the amino acid sequence of SEQ ID NO:4 that comprises four or more amino acid substitutions, wherein the four or more amino acid substitutions comprise amino acid substitutions T21I, L69V, I80V, and L178F;
   (2) the amino acid sequence of SEQ ID NO:6 that comprises four or more amino acid substitutions, wherein the four or more amino acid substitutions comprise amino acid substitutions T21I, L69V, I80V, and L178F,
   wherein the positions of the substitutions in (1) or (2) refer to the amino acid residue positions in SEQ ID NO:3.

2. The mhFVIII of claim 1, further comprising the amino acid substitutions I661V.

3. The mhFVIII of claim 1, further comprising the amino acid substitutions H212Q, I215V, R269K, L318F and I661V.

4. The mhFVIII of claim 1, further comprising the amino acid substitutions A20K, H212Q, I215V, R269K, L318F and I661V.

5. The mhFVIII of claim 1, further comprising the amino acid substitutions R199K, H212Q, I215V, R269K, I310V, L318F, S332P and I661V.

6. The mhFVIII of claim 1, further comprising the amino acid substitutions A20K, R199K, H212Q, I215V, R269K, I310V, L318F, S332P and I661V.

7. The mhFVIII of claim 1, comprising the amino acid sequence of SEQ ID NO:4 with the amino acid substitutions T21I, L69V, I80V, and L178F.

8. The mhFVIII of claim 1, comprising the amino acid sequence of SEQ ID NO:4 with the amino acid substitutions T21I, L69V, I80V, L178F and I661V.

9. The mhFVIII of claim 1, comprising the amino acid sequence of SEQ ID NO:4 with the amino acid substitutions T21I, L69V, I80V, L178F, H212Q, I215V, R269K, L318F and I661V.

10. The mhFVIII of claim 1, comprising the amino acid sequence of SEQ ID NO:4 with the amino acid substitutions A20K, T21I, L69V, I80V, L178F, H212Q, I215V, R269K, L318F and I661V.

11. The mhFVIII of claim 1, comprising the amino acid sequence of SEQ ID NO:4 with the amino acid substitutions T21I, L69V, I80V, L178F, R199K, H212Q, I215V, R269K, I310V, L318F, S332P and I661V.

12. The mhFVIII of claim 1, comprising the amino acid sequence of SEQ ID NO:4 with the amino acid substitutions A20K, T21, L69V, I80V, L178F, R199K, H212Q, I215V, R269K, I310V, L318F, S332P and I661V.

13. A pharmaceutical composition, comprising:
the mhFVIII of claim 1; and
a pharmaceutically acceptable carrier.

14. A method. for treating a subject with a factor VIII deficiency, comprising:
administering to the subject an effective amount of the pharmaceutical composition of claim 13.

15. An isolated polynucleotide encoding the mhFVIII of claim 1, optionally containing a regulatory sequence operably linked to the polynucleotide.

16. An expression vector comprising the polynucleotide of claim 15.

17. The expression vector of claim 16, wherein the expression vector is a viral vector.

18. A host cell comprising the expression vector of claim 17.

19. A pharmaceutical composition, comprising:
the expression vector of claim 16; and
a pharmaceutically acceptable carrier.

20. A method for treating a subject with a factor VIII deficiency, comprising:
administering to the subject an effective amount of the pharmaceutical composition of claim 19.

21. A method for treating a subject with a factor VIII deficiency, comprising:
administering to the subject an effective amount of the host cell of claim 18, wherein the host cell expresses a mhFVIII.

22. The expression vector of claim 17 wherein the viral vector is an AAV vector.

23. The method for treating a subject with a factor VIII deficiency, comprising:
administering to the subject an effective amount of the expression vector of claim 22.

24. A recombinant AAV vector comprising a nucleotide sequence encoding a modified human factor VIII (mhFVIII), wherein the mhFVIII comprises:
(1) the amino acid sequence of SEQ ID NO:4 that comprises four or more amino acid substitutions, wherein the four or more amino acid substitutions comprise amino acid substitutions T21I, L69V, I80V, and L178F; or
(2) the amino acid se uence of SEQ ID NO:6 that comprises four or more amino acid substitutions. wherein the four or more amino acid substitutions comprise amino acid substitutions T21I, L69V, I80V, and L178F,
wherein the positions of the substitutions in (1) or (2) refer to the amino acids residue positions in SEQ ID NO:3 and
wherein the AAV vector is capable of expressing in a host cell the mhFVIII.

25. A method for treating a subject with a factor VIII deficiency, comprising:
administering to the subject an effective amount of the recombinant AAV vector of claim 24.

26. A method for expressing a modified human factor VIII (mhFVIII), comprising the steps of:
(a) introducing into host cells an expression vector comprising:
a polynucleotide comprising a nucleotide sequence encoding a signal peptide and a nucleotide sequence encoding the mhFVIII,
wherein the mhFVIII comprises:
(1) the amino acid sequence of SEQ ID NO:4 that comprises four or more amino acid substitutions, wherein the four or more amino acid substitutions comprise amino acid substitutions T21I, L69V, I80V, and L178F, or
(2) the amino acid sequence of SEQ ID N0:6 that comprises four or more amino acid substitutions, wherein the four or more amino acid substitutions comprise amino acid substitutions T21I, L69V, I80V, and L178F; wherein the positions of the substitutions in (1) or (2) refer to amino acids residue positions in SEQ ID NO:3; and
a regulatory sequence operatively linked to the polynucleotides;
(b) growing the host cells under conditions suitable for expression and secretion of the mhFVIII;
(c) harvesting culture medium from the host cells, and
(d) purifying the mhFVIII from the harvested culture medium.

* * * * *